(12) United States Patent
Roquet et al.

(10) Patent No.: US 12,002,547 B2
(45) Date of Patent: Jun. 4, 2024

(54) DATA STRUCTURES AND OPERATIONS FOR SEARCHING, COMPUTING, AND INDEXING IN DNA-BASED DATA STORAGE

(71) Applicant: CATALOG TECHNOLOGIES, INC., Charlestown, MA (US)

(72) Inventors: Nathaniel Roquet, Charlestown, MA (US); Swapnil P. Bhatia, Charlestown, MA (US); Paolo Ferragina, Pisa (IT)

(73) Assignee: CATALOG TECHNOLOGIES, INC., Boston, MA (US)

( * ) Notice: Subject to any disclaimer, the term of this patent is extended or adjusted under 35 U.S.C. 154(b) by 0 days.

(21) Appl. No.: 18/107,851

(22) Filed: Feb. 9, 2023

(65) Prior Publication Data
US 2024/0055075 A1    Feb. 15, 2024

Related U.S. Application Data

(63) Continuation of application No. 16/872,129, filed on May 11, 2020, now Pat. No. 11,610,651.
(Continued)

(51) Int. Cl.
*G16B 30/00* (2019.01)
*G16B 50/00* (2019.01)
(Continued)

(52) U.S. Cl.
CPC ............. *G16B 30/00* (2019.02); *G16B 50/00* (2019.02)

(58) Field of Classification Search
None
See application file for complete search history.

(56) References Cited

U.S. PATENT DOCUMENTS 5,821,886 A    10/1998  Son
6,187,537 B1    2/2001  Zinn et al.
(Continued)

FOREIGN PATENT DOCUMENTS

| EP | 1512749 | 3/2005 |
|---|---|---|
| EP | 2329425 | 7/2013 |

(Continued)

OTHER PUBLICATIONS

Heng Li, Richard Durbin, Fast and accurate short read alignment with Burrows-Wheeler transform, Bioinformatics, vol. 25, Issue 14, Jul. 2009, pp. 1754-1760, https://doi.org/10.1093/bioinformatics/btp324 (Year: 2009).*

(Continued)

*Primary Examiner* — Hung Q Dang
(74) *Attorney, Agent, or Firm* — McDermott Will & Emery LLP

(57) ABSTRACT

The present disclosure is directed to enabling search and extraction of data stored in DNA with optimized data structures and functions. Accordingly, systems and methods are provided herein for performing certain functions on data stored in nucleic acid molecules. The present disclosure covers at least the following areas of interest: (1) data structures to provide efficient access and search of information stored in nucleic acid molecules, (2) accurate and quick reading of information stored in nucleic acid molecules, (3) targeted approaches to accessing subsets of information stored in nucleic acid molecules, (4) a rank function that determines a count of particular bit or symbol value in a set of information stored in nucleic acid molecules, (5) functions including counting, locating, and extracting occurrences of a specific pattern in a message of information stored in nucleic acid molecules, and (6) an if-then-else operation to sort data stored in nucleic acid molecules.

21 Claims, 31 Drawing Sheets

Related U.S. Application Data

(60) Provisional application No. 62/890,243, filed on Aug. 22, 2019, provisional application No. 62/860,117, filed on Jun. 11, 2019, provisional application No. 62/845,638, filed on May 9, 2019.

(51) Int. Cl.
  *G16B 50/50* (2019.01)
  *G16H 50/30* (2018.01)

(56) References Cited

U.S. PATENT DOCUMENTS

| | | |
|---|---|---|
| 6,221,653 B1 | 4/2001 | Caren et al. |
| 6,309,828 B1 | 10/2001 | Schleifer et al. |
| 6,384,210 B1 | 5/2002 | Blanchard |
| 6,419,883 B1 | 7/2002 | Blanchard |
| 6,446,642 B1 | 9/2002 | Caren et al. |
| 6,458,583 B1 | 10/2002 | Bruhn et al. |
| 6,537,747 B1 | 3/2003 | Mills et al. |
| 6,796,634 B2 | 9/2004 | Caren et al. |
| 7,176,297 B2 | 2/2007 | Li et al. |
| 7,306,316 B2 | 12/2007 | Doak |
| 7,491,422 B2 | 2/2009 | Zhang et al. |
| 7,600,840 B2 | 10/2009 | Kim et al. |
| 7,802,517 B2 | 9/2010 | Wessels et al. |
| 7,833,701 B2 | 11/2010 | Oshima |
| 7,909,427 B2 | 3/2011 | Kim et al. |
| 7,951,334 B2 | 5/2011 | Mirkin et al. |
| 8,071,168 B2 | 12/2011 | Cruchon-Dupeyrat |
| 8,114,207 B2 | 2/2012 | Sylvain et al. |
| 8,136,936 B2 | 3/2012 | Josten |
| 8,496,326 B2 | 7/2013 | Hook et al. |
| 8,735,327 B2 | 5/2014 | Macula |
| 8,769,689 B2 | 7/2014 | Hoglund |
| 8,806,127 B2 | 8/2014 | Brownell et al. |
| 8,856,940 B2 | 10/2014 | Kencl et al. |
| 8,937,564 B2 | 1/2015 | Aloni et al. |
| 9,061,494 B2 | 6/2015 | Rogers et al. |
| 9,062,218 B2 | 6/2015 | Oshima et al. |
| 9,187,777 B2 | 11/2015 | Jacobson et al. |
| 9,266,370 B2 | 2/2016 | Jung et al. |
| 9,317,664 B2 | 4/2016 | Ahuja et al. |
| 9,384,320 B2 | 7/2016 | Church |
| 9,403,180 B2 | 8/2016 | Ha et al. |
| 9,487,002 B2 | 11/2016 | Rogers et al. |
| 9,616,661 B2 | 4/2017 | Pierik et al. |
| 9,679,030 B2 | 6/2017 | Hatami-Hanza |
| 9,684,678 B2 | 6/2017 | Hatami-Hanza |
| 9,774,351 B2 | 9/2017 | Huetter et al. |
| 9,830,553 B2 | 11/2017 | Chen et al. |
| 9,904,734 B2 | 2/2018 | Murrah et al. |
| 9,928,869 B2 | 3/2018 | Church |
| 9,996,778 B2 | 6/2018 | Church |
| 10,020,826 B2 | 7/2018 | Gladwin et al. |
| 10,027,347 B2 | 7/2018 | Le et al. |
| 10,047,235 B2 | 8/2018 | Wilsher et al. |
| 10,050,959 B2 | 8/2018 | Soon-Shong et al. |
| 10,287,573 B2 | 5/2019 | Macula |
| 10,289,801 B2 | 5/2019 | Church |
| 10,370,246 B1 | 8/2019 | Milenkovic et al. |
| 10,387,301 B2 | 8/2019 | Goldman et al. |
| 10,417,457 B2 | 9/2019 | Peck |
| 10,423,341 B1 | 9/2019 | Kermani |
| 10,438,662 B2 | 10/2019 | Predki |
| 10,460,220 B2 | 10/2019 | Church |
| 10,566,077 B1 | 2/2020 | Milenkovic et al. |
| 10,640,822 B2 | 5/2020 | Predki et al. |
| 10,650,312 B2 | 5/2020 | Roquet et al. |
| 10,669,558 B2 | 6/2020 | Ganjam |
| 10,742,233 B2 | 8/2020 | Erlich |
| 10,754,994 B2 | 8/2020 | Peck |
| 10,774,379 B2 | 9/2020 | Chen et al. |
| 10,787,699 B2 | 9/2020 | Chen et al. |
| 10,793,897 B2 | 10/2020 | Chen et al. |
| 10,818,378 B2 | 10/2020 | Hutchison, III et al. |
| 10,838,939 B2 | 11/2020 | Walder et al. |
| 10,839,295 B2 | 11/2020 | Shen et al. |
| 10,853,244 B2 | 12/2020 | Petti et al. |
| 10,860,562 B1 | 12/2020 | Gupta et al. |
| 10,883,140 B2 | 1/2021 | Church et al. |
| 10,902,939 B2 | 1/2021 | Merriman et al. |
| 10,917,109 B1 | 2/2021 | Dimopoulou et al. |
| 10,929,039 B2 | 2/2021 | Kwon et al. |
| 10,936,953 B2 | 3/2021 | Peck et al. |
| 10,956,806 B2 | 3/2021 | Masuda et al. |
| 10,982,276 B2 | 3/2021 | Efcavitch et al. |
| 11,066,661 B2 | 7/2021 | Rausch et al. |
| 11,093,547 B2 | 8/2021 | Su et al. |
| 11,100,404 B2 | 8/2021 | Merriman et al. |
| 11,162,950 B2 | 11/2021 | Pfeiffer et al. |
| 11,164,190 B2 | 11/2021 | Pfeiffer et al. |
| 11,174,512 B2 | 11/2021 | Efcavitch et al. |
| 11,263,354 B2 | 3/2022 | Peck |
| 11,308,055 B2 | 4/2022 | Walder et al. |
| 11,326,161 B2 | 4/2022 | Church et al. |
| 11,339,423 B2 | 5/2022 | Bishop et al. |
| 11,435,905 B1 | 9/2022 | Kermani |
| 11,495,324 B2 | 11/2022 | Yekhanin et al. |
| 11,507,135 B2 | 11/2022 | Cheung et al. |
| 11,538,554 B1 * | 12/2022 | Milenkovic ............ G16B 50/50 |
| 2003/0116630 A1 | 6/2003 | Carey et al. |
| 2004/0244623 A1 | 12/2004 | Hayashizaki |
| 2005/0019760 A1 | 1/2005 | Southern |
| 2005/0166782 A2 | 8/2005 | Hayashizaki |
| 2005/0243618 A1 | 11/2005 | Boland |
| 2006/0263534 A1 | 11/2006 | Laurent et al. |
| 2008/0252679 A1 | 10/2008 | Pierik et al. |
| 2008/0269152 A1 | 10/2008 | Verdine et al. |
| 2008/0303870 A1 | 12/2008 | Verbeek et al. |
| 2008/0309701 A1 | 12/2008 | Pierik et al. |
| 2009/0023607 A1 | 1/2009 | Rozhok et al. |
| 2009/0033690 A1 | 2/2009 | Pierik et al. |
| 2009/0062129 A1 | 3/2009 | McKernan |
| 2009/0253141 A1 | 10/2009 | Quake |
| 2010/0029490 A1 | 2/2010 | Pierik et al. |
| 2010/0056381 A1 | 3/2010 | Kurt et al. |
| 2011/0195850 A1 | 8/2011 | Rozhok et al. |
| 2011/0312779 A1 | 12/2011 | Silverbrook et al. |
| 2011/0312782 A1 | 12/2011 | Azimi et al. |
| 2011/0312847 A1 | 12/2011 | Silverbrook et al. |
| 2011/0312851 A1 | 12/2011 | Silverbrook et al. |
| 2011/0312853 A1 | 12/2011 | Azimi et al. |
| 2011/0312855 A1 | 12/2011 | Silverbrook et al. |
| 2011/0312856 A1 | 12/2011 | Silverbrook et al. |
| 2012/0164396 A1 | 6/2012 | Mirkin et al. |
| 2012/0329561 A1 | 12/2012 | Evans et al. |
| 2013/0231254 A1 | 9/2013 | Kawashima et al. |
| 2013/0233709 A1 | 9/2013 | Dunbar |
| 2013/0253839 A1 | 9/2013 | Friedlander |
| 2014/0065609 A1 | 3/2014 | Hicks et al. |
| 2014/0296087 A1 | 10/2014 | Verdine et al. |
| 2014/0371100 A1 | 12/2014 | Kawashima et al. |
| 2015/0083797 A1 | 3/2015 | Tran et al. |
| 2015/0261664 A1 | 9/2015 | Goldman et al. |
| 2015/0269313 A1 | 9/2015 | Church |
| 2015/0312212 A1 | 10/2015 | Holmes et al. |
| 2015/0363550 A1 | 12/2015 | Green et al. |
| 2016/0007893 A1 | 1/2016 | Roberts |
| 2016/0051985 A1 | 2/2016 | Knight et al. |
| 2016/0168579 A1 | 6/2016 | Hutchinson et al. |
| 2016/0258939 A1 | 9/2016 | Morin |
| 2016/0304948 A1 | 10/2016 | Lee |
| 2016/0371434 A1 | 12/2016 | Strauss |
| 2017/0017436 A1 | 1/2017 | Church |
| 2017/0021611 A1 | 1/2017 | Jung et al. |
| 2017/0060924 A1 | 3/2017 | Fitzhardinge |
| 2017/0081716 A1 | 3/2017 | Peck |
| 2017/0093851 A1 | 3/2017 | Allen |
| 2017/0109229 A1 | 4/2017 | Huetter |
| 2017/0136452 A1 | 5/2017 | Niles et al. |
| 2017/0140095 A1 | 5/2017 | Kim |
| 2017/0218228 A1 | 8/2017 | Jose et al. |
| 2017/0363953 A1 | 12/2017 | Steinhart et al. |

(56) References Cited

U.S. PATENT DOCUMENTS

| | | |
|---|---|---|
| 2018/0068060 A1 | 3/2018 | Ceze et al. |
| 2018/0086781 A1 | 3/2018 | Liss |
| 2018/0101487 A1 | 4/2018 | Peck |
| 2018/0121478 A1 | 5/2018 | Walder et al. |
| 2018/0137418 A1 | 5/2018 | Roquet et al. |
| 2018/0173710 A1 | 6/2018 | Maftuleac et al. |
| 2018/0173738 A1 | 6/2018 | Lopez-Ortiz et al. |
| 2018/0253563 A1 | 9/2018 | Peck et al. |
| 2019/0020651 A1 | 1/2019 | Soon-Shiong et al. |
| 2019/0136307 A1 | 5/2019 | Predki |
| 2019/0138909 A1 | 5/2019 | Shen et al. |
| 2019/0142882 A1 | 5/2019 | Shepherd |
| 2019/0271032 A1 | 9/2019 | Owen |
| 2019/0325040 A1 | 10/2019 | Sagi |
| 2019/0344239 A1 | 11/2019 | Efcavitch et al. |
| 2019/0351673 A1 | 11/2019 | Roquet et al. |
| 2019/0355442 A1 | 11/2019 | Merriman |
| 2019/0383788 A1* | 12/2019 | Predki .................. C12Q 1/6869 |
| 2020/0076798 A1 | 3/2020 | Lidsky |
| 2020/0185057 A1 | 6/2020 | Leake et al. |
| 2020/0193301 A1 | 6/2020 | Roquet et al. |
| 2020/0242482 A1 | 7/2020 | Merriman et al. |
| 2020/0357483 A1 | 11/2020 | Roquet et al. |
| 2021/0010065 A1 | 1/2021 | Salk |
| 2021/0074380 A1 | 3/2021 | Yekhanin |
| 2021/0348214 A1 | 11/2021 | Roquet et al. |
| 2022/0364991 A1 | 11/2022 | Wanunu et al. |

FOREIGN PATENT DOCUMENTS

| | | |
|---|---|---|
| EP | 3067809 | 9/2016 |
| EP | 2856375 | 7/2018 |
| EP | 3346404 | 7/2018 |
| EP | 3542295 | 9/2020 |
| JP | 2009244996 | 10/2009 |
| WO | WO-03025123 | 3/2003 |
| WO | WO-2004009844 | 1/2004 |
| WO | WO-2012058638 | 5/2012 |
| WO | WO-2014014991 | 1/2014 |
| WO | WO-2015144858 | 10/2015 |
| WO | WO-2016015701 | 2/2016 |
| WO | WO-2016059610 | 4/2016 |
| WO | WO-2016081834 | 8/2016 |
| WO | WO-2016164779 | 10/2016 |
| WO | WO-2016182814 | 11/2016 |
| WO | WO-2017151195 | 9/2017 |
| WO | WO-2017189914 | 11/2017 |
| WO | WO-2017190297 | 11/2017 |
| WO | WO-2017192633 | 11/2017 |
| WO | WO-2018017131 | 1/2018 |
| WO | WO-2018049272 | 3/2018 |
| WO | WO-2018094108 | 5/2018 |
| WO | WO-2018094115 | 5/2018 |
| WO | WO-2018132457 | 7/2018 |
| WO | WO-2018148260 | 8/2018 |
| WO | WO-2018148458 | 8/2018 |
| WO | WO-2018213856 | 11/2018 |
| WO | WO-2019046768 | 3/2019 |
| WO | WO-2019081145 | 5/2019 |
| WO | WO-2019178551 | 9/2019 |
| WO | WO-2019195479 | 10/2019 |
| WO | WO-2019222561 | 11/2019 |
| WO | WO-2019246434 | 12/2019 |
| WO | WO-2020014478 | 1/2020 |
| WO | WO-2020028912 | 6/2020 |
| WO | WO-2020128517 | 6/2020 |
| WO | WO-2020132935 | 7/2020 |
| WO | WO-2022055885 | 3/2022 |

OTHER PUBLICATIONS

Design & Analysis of Algorithms, Lecture #25: Burrows-Wheeler Transform, pp. 1-8. (Year: 2018).*

Ben Langmead, Introduction to the Burrows-Wheeler Transform and FM Index, Department of Computer Science, JHU, pp. 1-12, Nov. 24, 2013. (Year: 2013).*

Boneh, D., et al., "Breaking DES Using a Molecular Computer," in DIMACS Workshop on DNA Computing, 1995.

Bonnet et al., "Rewritable digital data storage in live cells via engineered control of recombination directionality," Proceeding of the National Academy of Sciences, vol. 109(23): 8884-8889 (2012).

Bornholt et al., "A DNA-Based Archival Storage System," International Conference on Architectural Support for Programming Languages and Operating Systems (ASPLOS), Apr. 2-6, 2016, Atlanta, GA, 637-649.

Braich RS,et al., "Solution of a 20-variable 3-SAT problem on a DNA computer". Science. Apr. 19, 2002;296(5567):499-502. doi: 10.1126/science.1069528. Epub Mar. 14, 2002. PMID: 11896237.

Burks et al., "The GenBank Nucleic Acid Sequence Database," Cabios Review, vol. 1(4): 225-233 (1985).

Buschmann, et al., "Levenshtein Error-Correcting Barcodes for Multiplexed DNA Sequencing", BMC Bioinformatics, vol. 14, No. 1., pp. 1-10 (2013).

Bystrykh, et al., "Generalized DNA Barcode Design Based on Hamming Codes", PLOS ONE, vol. 7, No. 5, pp. 1-8, (May 2012).

Casini, A. "Advanced DNA assembly strategies and standards for synthetic biology," Thesis, Department of Life Sciences, Imperial College London: 1-178 (2014).

Clarke, et al., "Continuous base identification for single-molecule nanopore DNA sequencing" Nature Nanotechnology, vol. 4, pp. 265-270, (2009).

Craig, et al., "Ordering of Cosmid Clones covering the Herpes Simplex Virus Type 1 (HSV-1) genome: a test case for fingerprinting by hybridisation", Nucleic Acids Research, vol. 18, pp. 2653-2660 (1990).

De Silva, et al., "New Trends of Digital Data Storage in DNA", BioMed Research International, vol. 2016, Article ID 8072463, 14 pages (Sep. 5, 2016) ps. 14.

Deorowicz et al., "Data compression for sequencing data," Algorithms for Molecular Biology, vol. 8(25): 1-13 (2013).

Engler et al., "A One Pot, One Step, Precision Cloning Method with High Throughput Capability," PLoS ONE, vol. 3(11): E3647 (2008) printed as pp. 1-7.

Engler et al., "Chapter 12: Combinatorial DNA Assembly Using Golden Gate Cloning," Karen M. Polizzi and Cleo Kontoravadi (eds.), Synthetic Biology, Methods in Molecular Biology, vol. 1073, Springer Science+Business Media, New York: 141-156 (2013).

Erciyes, K., Distributed and Sequential Algorithms for Bioinformatics, Computational Biology, 2015, 23, Springer, Ed. A. Dress, 1-133. (Year: 2015).

Extended European Search Report for EP Application No. 17872172.6 dated Oct. 27, 2020.

Supplementary European Search Report for EP Application No. 17872574.3 dated Sep. 14, 2020.

Fogg et al., "New Applications for Phage Integrases," Journal of Molecular Biology, vol. 426(15): 2703-2716 (2014).

Goldman et al., "Towards practical, high-capacity, low-maintenance information storage in synthesized DNA," Nature, vol. 494: 77-80 (2013).

Kivioja et al., "Counting absolute numbers of molecules using unique molecular identifiers," Nature Methods, vol. 9(1): 72-74 (2011), including pp. 1-2 of Online Methods, and pp. 1-14 of Supplementary Information.

Lee, et al., "Enzymatic DNA synthesis for digital information storage", bioRxiv, XP055603868, DOI: 10.1101/348987 Retrieved from the Internet: URL:https://www.biorxiv.org/content/biorxiv/early/2018/06/16/348,987.full.pdf [retrieved on Nov. 20, 2019] abstract, pp. 31 pages (2018).

Lee et al., "DNA detection using commercial mobile phones", Biosensors and Bioelectronics, 2011, 26, 4349-4354 (Year: 2011).

Leier et al., "Cryptography with DNA binary strands," Biosystems, vol. 57: 13-22 (2000).

Lipton RJ., "DNA solution of hard computational problems", Science. Apr. 28, 1995;268(5210):542-5. doi: 10.1126/science.7725098. PMID: 7725098.

(56) References Cited

OTHER PUBLICATIONS

Navarro, et al., "Compressed Full-Text Indexes", ACM Computing Surveys, ACM, New York, NY, vol. 39, No. 1 Apr. 12, 2007.
Organick, et al., "Random access in large-scale DNA data storage", Nature Biotechnology, 36(3): 242-248, (2018).
Patrick, et al., DNA Assembly in 3D Printed Fluidics, PLOS One, 10(12): e014636 18 pages (2015).
PCT/US2017/062098 International Search Report and Written Opinion dated, Mar. 14, 2018 (20 pgs).
PCT/US2017/062106 International Search Report and Written Opinion dated, Feb. 22, 2018 (8 pgs).
PCT/US2019/022596 International Search Report and Written Opinion dated, Jun. 28, 2019 (14 pgs).
PCT/US2019/032756 International Search Report and Written Opinion dated, Sep. 4, 2019 (23 pgs).
PCT/US2019/045160 International Search Report and Written Opinion dated, Jan. 30, 2020 (19 pgs).
PCT/US2020/032384 International Search Report and Written Opinion dated, Jul. 30, 2020 (20 pgs).
PCT/US2020/055351 International Search Report and Written Opinion dated, Mar. 31, 2021 (20 pgs).
PCT/US2021/031865 International Search Report and Written Opinion dated, Aug. 13, 2021 (21 pgs).
PCT/US2021/049289 International Search Report and Written Opinion dated, Nov. 18, 2021 (13 pgs).
PCT/US2022/020949 International Search Report and Written Opinion dated, Jun. 23, 2022 (10 pgs).
PCT/US2022/050435 International Search Report and Written Opinion dated, May 11, 2023 (18 pgs).
PCT/US2023/15495 International Search Report and Written Opinion dated, May 23, 2023 (13 pgs).
Quetier et al., "The CRISPR-Cas9 technology: Closer to the ultimate toolkit for targeted genome editing," Plant Science, vol. 242: 65-76 (2015).
Roquet et al., "Synthetic recombinase-based state machines in living cells," Science, vol. 353(6297): 363, aad8559-1-aad8559-13 (2016).
Sands, et al., "Overview of Post Cohen-Boyer Methods for Single Segment Cloning and for Multisegment DNA Assembly," Current Protocols in Molecular Biology, vol. 113: 3.26.1-3.26-20 (2016).
Sorek et al., "CRISPR-Mediated Adaptive Immune Systems in Bacteria and Archaea," Annual Review of Biochemistry, vol. 82: 237-266 (2013).
Staden, R., "Nucleic Acids Research—Sequence Data Handling by Computer," vol. 4(11): 4037-4052 (1977).
Sun et al., "Recent advances in targeted genome engineering in mammalian systems," Biotechnology Journal, vol. 7: 1074-1087 (2012).
Tulpan, et al., "HyDEn: A Hybrid Steganocryptographic Approach for Data Encryption Using Randomized Error Correcting DNA Codes,", Biomed Research International, vol. 32, No. 4839, pp. 1-11, (2013).
Yang et al., "Permanent genetic memory with >1-byte capacity," Nature Methods, vol. 11(12): 1261-1266 (2014) including pp. 1-3 of Online Methods, and pp. 1-30 of Supplementary Figures and Text.
Yazdi et al., "A Rewritable, Random-Access DNA-Based Storage System," Scientific Reports, vol. 5(14138): 1-10 (2015), including pp. 1-19 of Supplementary Information.
Yazdi et al., "DNA-based storage: Trends and Methods," IEEE Transactions on Molecular, Biological, and Multi-Scale Communications, vol. 1(3): 230-248 (Sep. 1, 2015).
Yazdi, et al., "Portable and Error-Free DNA-Based Data Storage", bioRxiv preprint doi: https://doi.org/10.1101/079442 (2016).
Yim et al., "The essential component in DNA-based information storage system: robust error-tolerating module," Frontiers in Bioengineering and Biotechnology, vol. 2, Article 49: 1-5 (2014).
Zhu et al., "High-throughput DNA sequence data compression," Briefings in Bioinformatics, 16(1): 1-15 (2015).

* cited by examiner $C_{xy}$ is the yth component in layer x. For a starting library with M layers, each with N components, the identifiers would have the following architecture:

where a, b, c represent elements in the set {1, 2, ..., N}

| suffix | Suffix Position | sorted suffix | Suffix Position | M' | L |
|---|---|---|---|---|---|
| abracadabra$ | 0 | $ | 11 | $abracadabra | a |
| bracadabra$ | 1 | a$ | 10 | a$abracadabr | r |
| racadabra$ | 2 | abra$ | 7 | abra$abracad | d |
| acadabra$ | 3 | abracadabra$ | 0 | abracadabra$ | $ |
| cadabra$ | 4 | acadabra$ | 3 | acadabra$abr | r |
| adabra$ | 5 | adabra$ | 5 | adabra$abrc | c |
| dabra$ | 6 | bra$ | 8 | bra$abracada | a |
| abra$ | 7 | bracadabra$ | 1 | bracadabra$a | a |
| bra$ | 8 | cadabra$ | 4 | cadabra$abra | a |
| ra$ | 9 | dabra$ | 6 | dabra$abraca | a |
| a$ | 10 | ra$ | 9 | ra$abracadab | b |
| $ | 11 | racadabra$ | 2 | racadabra$ab | b |

FIG. 17

DATA STRUCTURES AND OPERATIONS FOR SEARCHING, COMPUTING, AND INDEXING IN DNA-BASED DATA STORAGE

CROSS-REFERENCE TO RELATED APPLICATIONS

This application is a continuation of U.S. application Ser. No. 16/872,129 filed May 11, 2020 know U.S. Pat. No. 11,610,651), which claims priority to and the benefit of U.S. Provisional Patent Application No. 62/845,638, filed May 9, 2019 now expired), and entitled "NUCLEIC ACID-BASED DATA STORAGE: SEARCH AND COMPUTE"; U.S. Provisional Patent Application No. 62/860,117, filed Jun. 11, 2019 (now expired), and entitled "DATA STRUCTURES FOR DNA STORAGE"; and U.S. Provisional Patent Application No. 62/890,243, filed on Aug. 22, 2019 (now expired), and entitled "INDEX AND SEARCH OF INFORMATION STORED IN DNA". The entire contents of the above-referenced applications are incorporated herein by reference.

BACKGROUND

Nucleic acid digital data storage is a stable approach for encoding and storing information for long periods of time, with data stored at higher densities than magnetic tape or hard drive storage systems. Additionally, digital data stored in nucleic acid molecules that are stored in cold and dry conditions can be retrieved as long as 60,000 years later or longer.

One way to access the digital data stored in nucleic acid molecules, the nucleic acid molecules is to sequence them. As such, nucleic acid digital data storage may be an ideal method for storing data that is not frequently accessed but may have a high volume of information to be stored or archived for long periods of time.

Existing methods of storing data in nucleic acid molecules rely on encoding the digital information (e.g., binary code) into base-by-base nucleic acids sequences, such that the base-to-base relationship in the sequence directly translates into the digital information (e.g., binary code). However, such de novo base-by-base nucleic acid synthesis is error prone and expensive. Moreover, certain functions cannot be performed on data that is stored via these existing methods of nucleic acid digital data storage, when data is encoded at single base resolution, without first translating the entire set of molecules into the digital information. For example, such functions include basic tasks that are commonly performed when the data is stored on a disk, such as logic functions, addition, subtraction, and query search, including whether or not a specific query pattern occurs in a data set, the number of occurrences, and the location of each occurrence.

SUMMARY

The present disclosure is directed to enabling search and extraction of data stored in DNA with optimized data structures and functions. Accordingly, systems and methods are provided herein for performing certain functions on data stored in nucleic acid molecules. The present disclosure covers at least the following areas of interest: (1) data structures to provide efficient access and search of information stored in nucleic acid molecules, (2) accurate and quick reading of information stored in nucleic acid molecules, (3) targeted approaches to accessing subsets of information stored in nucleic acid molecules, (4) a rank function that determines a count of particular bit or symbol value in a set of information stored in nucleic acid molecules, (5) functions including counting, locating, and extracting occurrences of a specific pattern in a message of information stored in nucleic acid molecules, and (6) an if-then-else operation to sort data stored in nucleic acid molecules.

While the systems and methods described herein may be used to read any nucleic acid sequence, the present disclosure is particularly advantageous when reading, accessing, and searching information stored in nucleic acid sequences that were written using particular encoding methods in identifier nucleic acid molecules (also referred to herein as simply "identifiers" or "identifier molecules"). The nucleic acid sequence of each identifier molecule corresponds to a particular symbol value (e.g., bit or series of bits when only two symbol values, '0' and '1', are possible, or alternatively, more than two symbol values are possible), that symbol's position (e.g., rank or address), or both, in a string of symbols (e.g., a bit stream or a symbol stream). For example, the presence or absence of an identifier molecule could signal a bit value of one or zero, respectively (or vice versa). The identifier nucleic acid molecules include combinatorial arrangements of component nucleic acid molecules (also referred to herein as simply "components" or "component molecules"). The nucleic acid sequences of the components are separated into unique sets (also referred to as layers). Identifier molecules are assembled by ligating together (or otherwise assembling) multiple component molecules, each component molecule having a sequence that is selected from each layer. In some cases, the component molecules self-assemble to form the identifier molecules. The set of possible identifier sequences corresponds to the various possible combinatorial combinations of the component sequences. For example, for C component sequences separated into M layers, with $c_i$ representing the number of component sequences in each $i^{th}$ layer, the number of possible identifier sequences that can be formed can be represented by $c_1 \times c_2 \times \ldots \times c_M$. As an example, an encoding scheme of 12 layers, each containing 10 component sequences can result in $10^{12}$ different unique identifier sequences. If each identifier sequence corresponds to a bit in a bit stream, this encoding scheme can represent 1 TB of data.

One way to improve efficiency in reading information from DNA involves using a data structure to store and indicate the location of data blocks of data string. For example, a large data string may be separated and stored into two or more containers. To determine which container contains information a user wants to access, the system may access a B-tree or triple store structure that holds the location (e.g., container number or placement). This allows a user to access the information he or she is looking for in an expedient manner—rather than reading the information in each of the containers containing the data string.

Data structures may also store data in nucleic acid molecules in configurations that enable fast operations, such as ranking bit/symbol values and searching for specific patterns in the data. For example, the system may access a counter array that represents a running count of bit/symbol value occurrences in a data string. This allows the system to determine ranks at bit/symbol values without reading every single nucleic acid molecule in the system. Data may be transformed via a Burrows-Wheeler transform or into a suffix array to store the data in a format suitable for compression and that enables efficient searching for specific patterns in the data, without having to read each individual nucleic acid molecule or sequence.

In some aspects, provided herein are systems and methods for storing digital information into nucleic acid molecules by obtaining a plurality of blocks, each block comprising a string of symbols and associated with a block ID. Such a system and method offer an advantage in that the block ID's could be used to facilitate searching of stored data by storing or implying information that characterizes the stored data or associated nucleic acid molecules. In this system and method, a block is assigned to a container and mapped to a plurality of identifier nucleic acid sequences to be associated with the container, each identifier nucleic acid sequence comprising component nucleic acid sequences, at least a portion of which are configured to bind to one or more probes. The system and method further constructs individual identifier nucleic acid molecules of the plurality of identifier nucleic acid sequences, and storing the individual identifier molecules in the assigned container, wherein a physical address, comprising the identities of the container and the plurality of identifier nucleic acid sequences associated therewith, is configured to be determined using the associated block ID.

For example, a block ID is an integer, a string, a triple, a list of attributes, or a semantic annotation. In some implementations, the physical address is stored in a data structure designed to facilitate access of the physical address using the associated block ID. The data structure may be one of a B-tree, a trie, or an array. At least a portion of the data structure may be stored along with the digital information in an index, which may comprise a second plurality of identifier nucleic acid sequences associated with a second container. The index may be a B-tree or trie data structure having nodes, each of which corresponds to a distinct plurality of identifier nucleic acid sequences of the second plurality of identifier nucleic acid sequences. The distinct identifiers that comprise a first node may be accessed, followed by reading the value associated those identifiers; these steps may be repeated over subsequent nodes, using the block ID to determine the identity of the distinct plurality of identifiers that comprise the subsequent node in relation to the value of the first node. The first node may be a root node of the B-tree or trie, and the process may continue until the value of a leaf node is read, in order to indicate whether the block for the block ID exists and what the corresponding physical address is. The block ID may be a string of symbols, and each node of the B-tree or trie data structure corresponds to a possible prefix of the string of symbols. A leaf node itself may represent a physical address associated with the block ID, matching the string of symbols specified by the leaf node.

In some implementations, the data structure is an array, each element of which corresponds to a distinct plurality of identifier nucleic acid sequences of the second plurality of identifier nucleic acid sequences. Each element of the array may correspond to a block ID or store the physical address of the associated block ID. In some implementations, the physical address is natively configured to the block ID such that the block ID maps to the physical address without having to store the physical address in an additional data structure. The block ID may map to a plurality of component nucleic acid sequences that are shared by all identifier nucleic acid sequences of the plurality of identifier nucleic acid sequences associated with the physical address. In some implementations, a plurality of identifier nucleic acid sequences associated with a block comprises contiguously ordered identifier nucleic acid sequences, such that said plurality of identifier nucleic acid sequences is specified in a corresponding physical address by an identifier range comprising the identities of the first and last identifier nucleic acid molecules in said identifier range. The first and last identifier nucleic acid sequences in said identifier range may be represented by integers.

In some implementations, the block ID is a position in a string of symbols that is represented by the corresponding block of a parent string of symbols. The parent string of symbols may be represented by a data structure for counting or locating the occurrences of a pattern in another string of symbols. Appropriate data structures include a Burrows-Wheeler Transform, a suffix array, a suffix tree, and an inverted index. Where the data structure is an array, each element of the array may comprise a distinct plurality of identifiers, corresponding to a block ID. Each element of the array may store the physical address of the associated block ID.

In some implementations, a physical address is accessed using a series of probes, from a pool of identifiers comprising the second plurality of identifier sequences. Data structures may be stored in a magnetic storage device, an optical storage device, a flash memory device, or cloud storage. Identifiers associated with a block may be accessed using a series of probes. Probes may be PCR primers or affinity tagged oligonucleotides, using PCR or an affinity pull down assay, respectively, for access.

In some aspects, provided herein are systems and methods for obtaining a rank of a particular bit or symbol value at a particular position in a string of bits or symbols, each bit or symbol having a value and a position, from digital information stored in a pool of nucleic acid molecules. The systems and methods involve obtaining a first pool of identifier nucleic acid molecules representative of the string of bits or symbols, the pool having powder, liquid, or solid form, each identifier nucleic acid molecule in the first pool comprising component nucleic acid molecules, at least a portion of which are configured to bind to one or more probes; and obtaining a second pool of identifier nucleic acid molecules representative of a string of counter symbols that is derived from the string of bits or symbols, each counter symbol representing a running count of the particular bit or symbol value in every w bits or symbols of the string of bits or symbols. The systems and methods further involve obtaining a first count by accessing the second pool with a second series of probes to target at least the identifier nucleic acid molecules within the second pool that represent a corresponding counter symbol that indicates the running count of the particular bit symbol value for either (1) all blocks of w bits or symbols preceding the particular position, or (2) all blocks of w bits or symbols preceding the particular position and including the block of w bits or symbols that includes the particular position. A second count is obtained by accessing the first pool with a first series of probes to target one or more distinct identifier nucleic acid molecules within the first pool that either (1) represents bits or symbols not counted in the first count and preceding or including the particular position, or (2) represents bits or symbols that were counted in the first count but that do not precede or include the particular position. The rank of the particular bit or symbol value at the particular position in the string is obtained from the first count and the second count.

One advantage of the rank function described herein is that it is not necessary to read the entirety of the string. Instead, the rank function uses selective access operations to read a subset of nucleic acid molecules that provide specific counts. In this manner, the rank operation described herein is performed in a more time-efficient and cost-effective manner, compared to a brute force operation that requires a full read of all stored nucleic acid molecules.

Identifiers may be formed by physically assembling M selected component nucleic acid molecules, each of the M selected component nucleic acid molecules being selected from a set of distinct component nucleic acid molecules that are separated into M different layers.

In some implementations, when the first count represents all blocks of w bits preceding the particular bit, the first series of probes in the second count targets one or more distinct identifier nucleic acid molecules within the first pool that represents bits not counted in the first count and preceding or including the particular bit, and the rank of the particular bit in the string of bits is obtained by summing the first and second counts. In some implementations, when the first count in the first count represents all blocks of w bits preceding the particular bit and including the block of w bits that includes the particular bit, the first series of probes targets one or more distinct identifier nucleic acid molecules within the first pool that represents bits counted in the first count but that do not precede or include the particular bit, and the rank of the particular bit in the string of bits is obtained by subtracting the second count from the first count.

In some implementations, the first pool is the second pool, or the first pool and the second pool are separate. The first count and second count may be obtained by reading the targeted identifier molecules from the second pool and the first pool, respectively. For the first count, the counter symbol value corresponding to the targeted identifiers may be read or determined. Blocks of w bits or symbols in the string may be mapped to blocks of contiguously ordered identifier nucleic acid molecules in the first pool. For example, the presence or absence of identifier molecules in the first pool does not correlate directly with a particular value in the string. Fixed length substrings (words) of the string may be mapped to codewords that comprise a fixed number of unique identifier nucleic acid molecules out of a fixed number of possible unique identifier nucleic acid molecules. Additional information, stored in the identifiers, may be used to detect and correct errors in writing, accessing, and reading identifiers.

Each counter symbol may be represented by a string of b counter bits. In some implementations, the string has a length of n bits or symbols, and b is the ceiling of $\log_2(n+1)$. The string of counter symbols may include a ceiling of n divided by w counter symbols, and is represented by a string of counter bits having length corresponding to b multiplied by the ceiling of n divided by w. In some implementations, if the particular bit or symbol is within the first block of w bits or symbols, the running count preceding the first block of w bits is zero. The value of w may be set to the value of b or one. For example, the first count is obtained by targeting identifier nucleic acid molecules in the second pool that represent the counter symbol corresponding to the blocks of w bits or symbols including the particular bit or symbol, and wherein the rank is equivalent to the first count. In this example, the last second count need not be obtained.

In some implementations if the particular bit is not within the first block of w bits or symbols, the counter symbol of all blocks of w bits or symbols preceding the particular bit or symbol represents the number of bits or symbols in the string that have a particular value within positions ranging from 0 to $w*B(x)-1$, where 0 is the first position of the string, and where x corresponds to the particular bit or symbol's position in the string and $B(x)$ is the floor of x divided by w. For example, the targeted identifier nucleic acid molecules within the second pool for the first count are within the range defined by positions $b*B(x)$ and $b*(B(x)+1)-1$, where a position of 0 corresponds to the first position in the string. The second count may correspond to a number of bits or symbols in the string that have a particular value within the range of positions $w*B(x)$ to x, where x corresponds to the particular bit or symbol's position in the string where position 0 is the first position, and $B(x)$ is the floor of x divided by w.

In some implementations where the string is a string of bits, the identifier nucleic acid molecules in the first pool represent the string of bits such that the presence of an identifier represents the bit-value of '1' at a bit position. The string of bits may represent a string of symbols, and rank is obtained for a particular symbol in the string of symbols.

In some implementations where the string is a string of symbols, the presence of corresponding identifier nucleic acid molecules in the first pool indicates a first symbol value, and the absence of corresponding identifier nucleic acid molecules in the first pool indicates a second symbol value. Symbol values may be selected from a set of symbol values (e.g., an alphabet), and the string of counter symbols indicates a running count of a number of symbols that have a particular symbol value. The string of symbols may represent a string of bits. For example, each symbol in the string corresponds to a fixed number of bits. In some implementations, different second pools of identifier nucleic acid molecules represent different strings of counter symbols that count the number of instances of specific symbol values, each different string of counter symbols counting instances of a corresponding specific symbol value.

In some aspects, provided herein are systems and methods for fetching digital information from a pool of nucleic acid molecules. The systems and methods involve obtaining a first pool of identifier nucleic acid molecules, the pool having powder, liquid, or solid form, each identifier nucleic acid molecule in the first pool comprising component nucleic acid molecules, at least a portion of which are configured to bind to one or more probes, wherein the identifier nucleic acid molecules represent strings of symbols such that the symbol values are indicated by a presence or absence of the corresponding identifier nucleic acid molecules in said first pool. Said first pool is accessed with a first series of probes, each of which targets at least one of the component nucleic acid molecules, to create a second pool with a subset of identifier nucleic acid molecules from said first pool. The sequences of said subset of identifier nucleic acid molecules from said second pool are read, and said sequences are used to obtain at least a subset of symbols in the string of symbols.

Each identifier nucleic acid molecule comprises distinct component nucleic acid molecules having component nucleic acid sequences from each of M layers, wherein each layer comprises a set of the component nucleic acid sequences. The M layers may be logically ordered, and the component nucleic acid sequences of each layer may be logically ordered. In some implementations, the identifier nucleic acid molecules correspond to identifier nucleic acid sequences that are logically ordered by sorting the identifier nucleic acid sequences by the corresponding component nucleic acid sequences in the first layer, sub-sorting the identifier nucleic acid sequences by the corresponding component nucleic acid sequences in the second layer, and repeating the sub-sorting process for each of the remaining M−2 layers. Each identifier sequence may include a series of component nucleic acid sequences that are represented as paths in a query tree that start at a root node, diverge over M instances, one instance for each layer, and terminate at leaf nodes, each leaf node representing an identifier nucleic acid sequence. Accordingly, the first series of probes may correspond to a partial or full path from the root node in the query tree. The full path may correspond to a root-to-leaf path that includes M probes, such that the series of the probes targets a single identifier nucleic acid molecule, and the partial path corresponds to fewer than M probes, such that the series of the probes targets multiple populations of identifier nucleic acid molecules having different sequences. The multiple populations of identifier nucleic acid molecules having different sequences may correspond to different component nucleic acid molecules in at least the $M^{th}$ layer.

In some implementations, the first pool is accessed with a plurality of series of probes. For example, the systems and methods perform splitting the first pool into at least two duplicate pools and executing the steps of the approach on each of said duplicate pools with each of the series of probes. The first pool may be replicated (e.g., via PCR) prior to splitting into the at least two duplicate pools. In some implementations, a first pool of identifier nucleic acid molecules is accessed with a sub-series of probes to create an intermediate pool of identifier nucleic acid molecules. An intermediate pool may be accessed with a subsequent sub-series of probes to form a second intermediate pool of identifier nucleic acid molecules or a second pool of identifier nucleic acid molecules. At least two intermediate pools may be combined to form another intermediate pool or a second pool. Probes may be PCR primers (for access via PCR) or affinity tagged oligonucleotides (for access via an affinity pull down assay).

In some aspects, provided herein are systems and methods for obtaining a count of a particular bit pattern of length p in a message comprising a string of bits of length n. The systems and methods obtain a first pool of identifier nucleic acid molecules representative of a string of bits L, wherein the string of bits L is a last column of a Burrows-Wheeler Transform matrix of the message, the first pool having powder, liquid, or solid form, each identifier nucleic acid molecule in the first pool comprising component nucleic acid molecules, at least a portion of which are configured to bind to one or more probes. A second pool of identifier nucleic acid molecules is obtained, representative of a string of counter symbols that is derived from the string of bits L, each counter symbol represented by a string of b counter bits indicative of a running count of a number of bits, for every w bits in the string of bits L that have a specific bit value of '1'. A series of probes are used to access the identifier nucleic acid molecules from the second pool that represent the counter symbol for a total number of occurrences of bit value of '1' in the string of bits L. The accessed identifier nucleic acid molecules from the second pool are read to count the total number of occurrences of bit value of '1', in the string of bits L. The total number of occurrences of each bit value is to reconstruct a first column F of the Burrows-Wheeler Transform matrix of the message. First position h and a last position z are determined, that define a range of the $p^{th}$ bit value in the first column F, inclusive of h and z. Using a first series of probes, the identifier nucleic acid molecules from the first pool and the second pool are accessed to calculate the rank $r_{h-1}$ of the $(p-i)^{th}$ bit value of the pattern, at position h−1 in L, where i=1. Using a second series of probes, the identifier nucleic acid molecules from the first pool and second pool are accessed to calculate the rank $r_z$ of the $(p-i)^{th}$ bit value of the pattern, at position z in L.

If $r_{h-1}$ is equal to $r_z$, the count of occurrences of the pattern in the message is set as zero. Otherwise, if $r_{h-1}$ is not equal to $r_z$, h is set to the index of the $(r_{h-1}+1)^{th}$ instance of the $(p-i)^{th}$ bit value in F. z is set to the index of the $r_z^{th}$ instance of the $(p-i)^{th}$ bit value in F. The loop counter i is incremented by one, and the access and indexing steps are repeated a number of times until i=p−1. The count of occurrences of the pattern in the message is counted as z−h+1. At least one advantage provided by the present approach is that a search can be performed over a large dataset without reading every single bit in the dataset; instead, the present disclosure logically locates occurrences of the pattern via selective access and rank operations. Another advantage provided herein is that the access and rank operations can be performed in parallel on the first and second pools, in order to minimize execution time and increase throughput.

The first pool may be the same as the second pool or may be separate from the second pool. In some implementations, a third pool of identifier nucleic acid molecules is obtained, representative of a suffix array that is derived from the Burrows-Wheeler Transform of the message, each element of the suffix array represented by a bit string of at least $\log_2(n)$ bits indicative of the position of the corresponding element of L in the message. The systems and methods may further locate the occurrences of the pattern in the message, when the count is greater than zero, by accessing the identifier nucleic acid molecules in the third pool corresponding to the elements in the suffix array at positions between and including final values for h and z. In some implementations, a fourth pool of identifier nucleic acid molecules is obtained, representative of the message. The systems and methods may further extract the context of a first location of the pattern by accessing the identifier nucleic acid molecules in the fourth pool corresponding to said first location and the neighborhood of positions surrounding the first location.

In some implementations, the presence of corresponding identifier nucleic acid molecules in the first pool indicates the bit value of 1, and the absence of corresponding identifier nucleic acid molecules in the first pool indicates the bit value of 0. b may be equal to the ceiling of $\log_2(n+1)$. The string of counter symbols may include a ceiling of n divided by w counter symbols, and is represented by a string of counter bits having length corresponding to b multiplied by the ceiling of n divided by w. The running count of any bit value preceding the first block of w bits in L is zero. w may be set to the value of b or one. The system and method may map blocks of bits in the string of bits L to blocks of contiguously ordered identifier nucleic acid molecules in the first pool. Fixed-length substrings of the string of bits L may be mapped to codewords that are represented by a fixed number of unique identifier acid molecules selected from a fixed-size set of unique identifier nucleic acid molecules. Additional information is used to detect and correct errors in writing, accessing, and reading identifier nucleic acid molecules from the first and second pool, and the additional information may be stored in the identifiers.

In some aspects, provided herein are systems and methods for obtaining a count of a particular bit pattern of length p in a message. The systems and methods obtain a first pool of identifier nucleic acid molecules representative of a string of bits L, wherein the string of bits L is a last column of a Burrows-Wheeler Transform matrix of the message, the first pool having powder, liquid, or solid form, each identifier nucleic acid molecule in the first pool comprising component nucleic acid molecules, at least a portion of which are configured to bind to one or more probes. A second pool of identifier nucleic acid molecules is obtained, representative of a string of counter symbols that is derived from the string of bits L and represent a running count of a number of bits having a specific bit value. The count of the particular bit pattern in the message is obtained by selectively accessing identifier nucleic acid molecules from the first pool and the second pool. At least one advantage provided by this technique is that a search can be performed over a large dataset without reading every single bit in the dataset; instead, the technique involves logically locating occurrences of the pattern via selective access. Another advantage provided herein is that the access operations can be performed in parallel on the first and second pools, in order to minimize execution time and increase throughput.

In some aspects, provided herein are systems and methods for obtaining a count of a particular symbol pattern of length $p_s$ in a message comprising a string of symbols of length ns, each symbol being selected from a set of r symbol values. The systems and methods obtain a first pool of identifier nucleic acid molecules representative of a string of symbols L that is the last column of a Burrows-Wheeler Transform matrix of the message, the first pool having powder, liquid, or solid form, and each identifier nucleic acid molecule in the first pool comprising component nucleic acid molecules, at least a portion of which are configured to bind to one or more probes. The systems and methods further obtain r second pools of identifier nucleic acid molecules, each of which corresponds to a string of counter symbols, $C_v$ for $v=1, 2, \ldots, r$, that is derived from L and represents a running count of a number of symbols in L with a corresponding symbol value $R_v$. The systems and methods obtain the count of a particular symbol pattern of length $p_s$ in the message, by selectively accessing identifier nucleic acid molecules from the first pool and the r second pools. At least one advantage provided by this approach is a search can be performed over a large dataset without reading every single bit in the dataset; instead, the present approach logically locates occurrences of the pattern via selective access. Another advantage provided herein is that the access operations can be performed in parallel on the first and second pools, in order to minimize execution time and increase throughput.

In some implementations, the present approach includes reconstructing a first column F of the Burrows-Wheeler Transform matrix. Using a series of probes, the identifier nucleic acid molecules may be accessed from the last counter symbol in each of the r second pools that represent the total number of occurrences of each corresponding symbol value $R_v$ in L; and using said total number of occurrence of each corresponding symbol value $R_v$ to reconstruct F. A range of positions in F that have the p-th symbol value in the pattern may be determined. In some implementations, the present approach includes determining a first rank of the corresponding symbol value in L at a position immediately preceding the range and a second rank of the corresponding symbol value in L at a position at the end of the range, using a series of probes to access the identifier nucleic acid molecules from the first pool and the corresponding second pool; and using the first rank and the second rank to update the range to the range of positions in F that have instances of the corresponding symbol that precede the subsequent symbol in the pattern.

In some implementations, the first rank $r_{h-1}$ is of the respective preceding symbol value in the pattern, at position h−1 in L, and the second rank $r_z$ is of the respective preceding symbol value in the pattern, at position z in L. The count of occurrences of the pattern in the message may be determined based on the final values of the first and second ranks. For example, the count is a difference between the final values of the first and second ranks. The count may be set to zero if the first and second ranks are determined to be equal.

In some implementations, the present approach includes obtaining a pool of identifier nucleic acid molecules, the SA pool, representative of a suffix array, SA, that is derived from the Burrows-Wheeler Transform of the message, each element of SA represented by a bit string of at least $\log_2(n)$ bits indicative of the position of the corresponding element of L in the message. The method and system may locate the occurrences of the pattern in the message, given that the count is greater than zero, by accessing identifier nucleic acid molecules in the SA pool that correspond to elements of the SA at positions given by the final range of positions in F. The present approach may include obtaining a message pool of identifiers representative of the message, allowing for extraction of the context of a first location of the pattern by accessing the identifier nucleic acid molecules in the message pool corresponding to said first location and the neighborhood of positions surrounding the first location.

In some implementations, the first pool of identifier nucleic acid molecules is one of r first pools, each corresponding to a string of bits $L_v$ for $v=1, 2, \ldots, r$, such that elements of $L_v$ have a bit-value of '1' for elements of L that match the symbol value $R_v$ and a bit-value of '0' otherwise, or vice versa. For example, the first pool corresponding to $L_v$ is used to determine the first and second rank of a symbol value $R_v$ in the pattern.

In some aspects, provided herein are systems and methods for operating on digital information stored in nucleic acid molecules. The systems and methods obtain a first pool of identifier nucleic acid molecules, the pool having powder, liquid, or solid form, each identifier nucleic acid molecule in the first pool comprising component nucleic acid molecules, at least a portion of which are configured to bind to one or more probes, wherein the identifier nucleic acid molecules represent input strings of symbols. An if-then-else operation is performed on the identifier nucleic acid molecules in the first pool, wherein the if-then-else operation targets at least one of the component nucleic acid molecules with a probe, to create an intermediate pool with a subset of identifier nucleic acid molecules from said first pool. The if-then-else operation is repeated, wherein the intermediate pool replaces the first pool at every subsequent step until a final pool of identifier nucleic acid molecules is created that represents at least a portion of an output string of symbols.

Using this approach allows for conditional programs to be written. For example, each "if" operation tests the presence or absence of one or more identifiers, and, depending on its presence or absence, continues to either "then" or "else" branches. The operation may comprise multiple conditions and corresponding branches. An output may be produced from all the branches of the operation. This approach allows for all of the identifiers in a plurality of identifier libraries (e.g., of terabit scale) to be operated upon in parallel. For example, if a library encodes billions data objects, then complex functions that examine each object and produce an output can be designed as DNA-based programs and executed on the libraries in parallel.

The present disclosure includes strategies to shift, copy, and move bits that rearrange an identifier library into multiple input identifier libraries for the execution of a desired program. Physically, each if-then-else operation may take place in a reaction that transforms an input library into two output libraries, and may be multiplexed across all identifiers in those libraries. The output library of one operation may be channeled to the input of another, e.g., through a fluidic transfer. Unlike conventional hardware that is limited by RAM and processing power, the DNA platform described herein is capable of executing a program across a massive amount of input data objects simultaneously and with low power.

The identifiers may comprise a distinct component from each of M layers, each layer comprising a set of components. Probes may be PCR primers or affinity tagged oligonucleotides, whereby accessing is performed via PCR or an affinity pull down assay, respectively. In some implementations, an if-then-else operation comprises accessing identifier nucleic acid molecules in a pool that includes a specific component nucleic acid molecule. The operation may include splitting or replicating (e.g., via PCR) at least one of the first pool, the intermediate pool, or the final pool into at least two duplicate pools, combining at least two intermediate pools to form a new intermediate pool or a second pool, or both. Two or more if-then-else operations may be executed on one or more pools in parallel.

In some aspects, provided herein is a system configured to perform any of the methods described herein. The system may be a printer-finisher system configured to dispense DNA components at discrete locations (e.g., reaction compartments) on a substrate, dispense reagents provide optimal conditions for the ligation reaction, and pool all of the DNA identifiers that comprise a library. The system may store and manipulate nucleic acid molecules in containers (e.g., via automated liquid handling). The system may dispense probes into compartments or containers to access subsets of nucleic acid molecules. The system may be configured to aliquot and replicate pools of nucleic acid molecules.

In some aspects, provided herein is a composition including nucleic acid molecules representing digital information according to any of the methods described herein. The composition includes identifier nucleic acid molecules comprising component nucleic acid molecules. Identifier nucleic acid molecules may be collected in a pool and mapped to digital information. For example, the presence of an identifier indicates a particular bit or symbol value in a string of symbols, and the absence of an identifier indicates another bit or symbol value in the string of symbols.

BRIEF DESCRIPTION

The above and other features of the present disclosure, including its nature and its various advantages, will be more apparent upon consideration of the following detailed description, taken in conjunction with the accompanying drawings in which:

FIG. 1 schematically illustrates an overview of a process for encoding, writing, accessing, querying, reading, and decoding digital information stored in nucleic acid sequences;

FIGS. 2A and 2B schematically illustrate an example method of encoding digital data, referred to as "data at address", using objects or identifiers (e.g., nucleic acid molecules); FIG. 2A illustrates combining a rank object (or address object) with a byte-value object (or data object) to create an identifier; FIG. 2B illustrates an implementation of the data at address method wherein the rank objects and byte-value objects are themselves combinatorial concatenations of other objects;

FIGS. 3A and 3B schematically illustrate an example method of encoding digital information using objects or identifiers (e.g., nucleic acid sequences); FIG. 3A illustrates encoding digital information using a rank object as an identifier; FIG. 3B illustrates an implementation of the encoding method wherein the address objects are themselves combinatorial concatenations of other objects;

FIG. 4 shows a contour plot, in log space, of a relationship between the combinatorial space of possible identifiers (C, x-axis) and the average number of identifiers (k, y-axis) that may be constructed to store information of a given size (contour lines);

FIG. 5 schematically illustrates an overview of a method for writing information to nucleic acid sequences (e.g., deoxyribonucleic acid);

FIGS. 6A and 6B illustrate an example method, referred to as the "product scheme", for constructing identifiers (e.g., nucleic acid molecules) by combinatorially assembling distinct components (e.g., nucleic acid sequences); FIG. 6A illustrates the architecture of identifiers constructed using the product scheme; FIG. 6B illustrates an example of the combinatorial space of identifiers that may be constructed using the product scheme;

FIG. 7 schematically illustrates the use of overlap extension polymerase chain reaction to construct identifiers (e.g., nucleic acid molecules) from components (e.g., nucleic acid sequences);

FIG. 8 schematically illustrates the use of sticky end ligation to construct identifiers (e.g., nucleic acid molecules) from components (e.g., nucleic acid sequences);

FIG. 9 schematically illustrates the use of recombinase assembly to construct identifiers (e.g., nucleic acid molecules) from components (e.g., nucleic acid sequences);

FIGS. 10A and 10B demonstrates template directed ligation; FIG. 10A schematically illustrates the use of template directed ligation to construct identifiers (e.g., nucleic acid molecules) from components (e.g., nucleic acid sequences); FIG. 10B shows a histogram of the copy numbers (abundances) of 256 distinct nucleic acid sequences that were each combinatorially assembled from six nucleic acid sequences (e.g., components) in one pooled template directed ligation reaction;

FIG. 17 shows a suffix array relative to a Burrows-Wheeler matrix;

DETAILED DESCRIPTION

Figure 1:
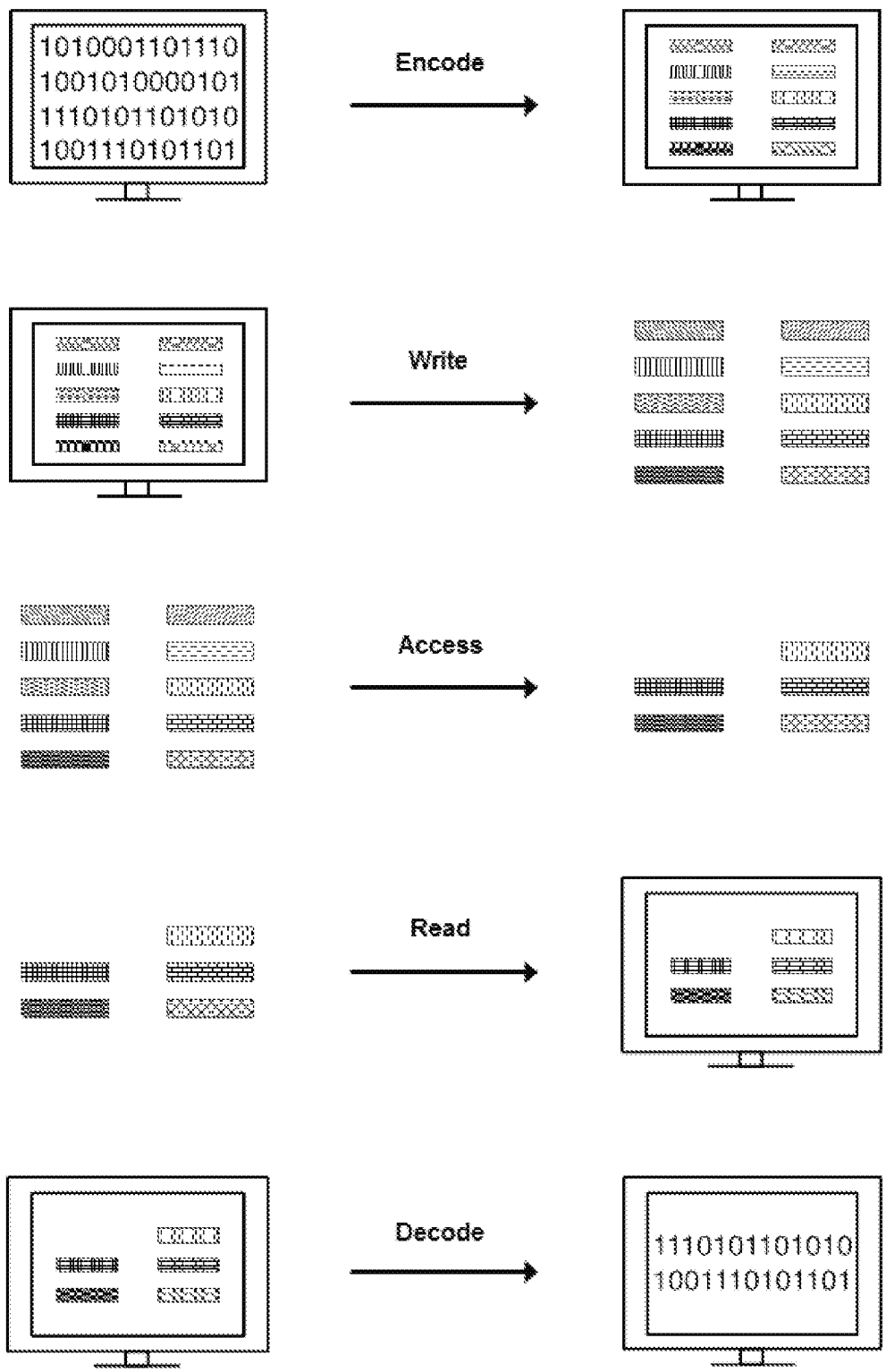

To provide an overall understanding of the assemblies and methods described herein, certain illustrative implementations will be described. Although the implementations and features described herein are specifically described for data storage in identifier nucleic acid molecules made up of component nucleic acid molecules, it will be understood that all the aspects and other features outlined below may be combined with one another in any suitable manner and may be adapted and applied to other forms of DNA-based data storage.

Base-by-base synthesis of nucleic acids for encoding digital information can be costly and time consuming, because it generally requires a de novo base-by-base synthesis of distinct nucleic acid sequences (e.g., phosphoramidite synthesis) for every new information storage request. The present disclosure relates to systems and methods that do not rely on base-by-base or de novo synthesis, and instead encode the digital information in a plurality of identifiers, or nucleic acid sequences, that include combinatorial arrangements of components (or component nucleic acid sequences). In this manner, the systems and methods of the present disclosure improve the efficiency and commercial viability of digital information storage.

The present disclosure describes methods that produce a first set of distinct nucleic acid sequences (or components) for the first request of information storage, and can thereafter reuse the same nucleic acid sequences (or components) for subsequent information storage requests. These approaches significantly reduce the cost of DNA-based information storage by reducing the role of de novo synthesis of nucleic acid sequences in the information-to-DNA encoding and writing process.

Moreover, unlike implementations of base-by-base synthesis, such as phosphoramidite chemistry-based or template-free polymerase-based nucleic acid elongation, which use cyclical delivery of each base to each elongating nucleic acid, the systems and methods of the present disclosure relate to information-to-DNA writing using identifier construction from components are highly parallelizable processes that do not necessarily use cyclical nucleic acid elongation. Thus, the present disclosure increases the speed of writing digital information to DNA compared to other methods. Various systems and methods of writing digital information into nucleic acid molecules are described in U.S. Pat. No. 10,650,312 entitled "NUCLEIC ACID-BASED DATA STORAGE", filed Dec. 21, 2017 (describing encoding digital information in DNA); U.S. application Ser. No. 16/461,774 entitled "SYSTEMS FOR NUCLEIC ACID-BASED DATA STORAGE", filed May 16, 2019 and published as U.S. Publication No. 2019/0362814 (describing encoding schemes for DNA-based data storage); U.S. application Ser. No. 16/414,758 entitled "COMPOSITIONS AND METHODS FOR NUCLEIC ACID-BASED DATA STORAGE", filed May 16, 2019; and U.S. application Ser. No. 16/532,077 entitled "SYSTEMS AND METHODS FOR STORING AND READING NUCLEIC ACID-BASED DATA WITH ERROR PROTECTION", filed Aug. 5, 2019 (describing data structures and error protection and correction for DNA encoding), each of which is hereby incorporated by reference in its entirety.

The following description begins with an overview of various systems and methods for encoding data in nucleic acid molecules, and describes various writing and archival systems configured to print and store nucleic acid molecules that encode digital data, as described in relation to FIGS. 1-10. The present disclosure then describes various encoding methods in relation to FIGS. 11-14. The present disclosure relates to improvements on the methods of writing and reading digital information in nucleic acid molecules, described in the above-referenced patent applications. Specifically, using a data structure to represent the digital information can improve efficiency in reading information from DNA, by defining specific characteristics of the digital information and organizing them in a manner that makes them easy to access in DNA.

As one example, a large data string is separated into two or more substrings, and each substring is stored in a separate pool of nucleic acid molecules that is placed into its own container. One way to determine which container contains the desired information is to access a data structure (such as a B-tree or trie structure, for example), that identifies the location (e.g., container number or placement). By using the data structure to reference which container is relevant, the user can access just the container(s) that contain the desired information, rather than reading the information in each container one-by-one before determining whether the information is relevant. This improves the efficiency of accessing relevant information in a data string in nucleic acid molecules.

As an extension of the above example, the relevant information that the user wishes to access may be represented in or calculable from only a subset of the nucleic acid molecules in a container's pool. In this case, the present disclosure provides a way to access only the specific subset of molecules that are relevant, without having to access all of the information stored in the entire pool of nucleic acid molecules. Doing so would increase efficiency and reduce cost. One way to access only a desirable subset of nucleic acid molecules in a pool is to refer to a data structure (such as a B-tree of trie structure, for example), which stores information that can be used to target specific subsets of nucleic acid molecules in the pool. Examples of specific data structures that can be used to access and search specific subsets of nucleic acid molecules in a pool (or across different pools in different containers) are described in relation to FIGS. 15-19. Moreover, the present disclosure relates to systems and methods that rely on data structures to efficiently perform certain operations on data that is stored in nucleic acid molecules, such as searching, location, and extraction functions. Specifically, example systems and methods that rely on one or more data structures to access specific data portions stored in nucleic acid molecules, for performing operations such as reading, accessing, and ranking, are described in relation to FIGS. 20-25, while systems and methods that rely on one or more data structures to access specific data portions stored in nucleic acid molecules, for performing operations such as searching, locating, and extracting specific patterns or queries from data stored in nucleic acid molecules, are described in relation to FIGS. 26-32. Lastly, a logical if-then-else operation is described in relation to FIG. 33.

Generally, the present disclosure encodes data (which is represented by a string of one- or zero-bits, or by a string of symbols, where each symbol is selected from a set of more than two symbol values) into a set of identifier nucleic acid sequences (or identifier sequence), where each unique identifier sequence has a corresponding bit or symbol in the string. The identifier sequence encodes the bit or symbol's position in the string, its value, or both the position and value. One way to implement the systems and methods of the present disclosure is to create each identifier nucleic acid molecule (or identifier molecule), which is represented by an identifier sequence, by ligating premade DNA component molecules (represented by component sequences) in an ordered manner that is based on defined layers, as is discussed in relation to FIGS. 1-11. Specifically, the component sequences in the different layers are combinatorially combined across the layers (one component sequence is selected per layer, for example) and concatenated (e.g., ligated) to form identifier sequences that are mapped one-to-one to each symbol or bit in the string.

Generally, a component nucleic acid sequence is configured to bind one or more probes that can be used to select for all identifiers comprising said sequence. For example, a component may comprise a target sequence of 20 bases and a probe may comprise a complementary 20 base oligonucleotide for binding the target sequence. As described in the present disclosure, the composition of identifier nucleic acid sequences from components, each of which are capable of binding a unique probe, offers beneficial features when it comes to accessing and operating on the stored data. Though the methods of generating identifiers presented herein are especially configured to generate identifiers comprising components, it should be understood that such identifier nucleic acid molecules may be formed through a number of alternative methods. For example, de novo synthesis that generates nucleic acid sequences of length 100 bases can be used to create identifier nucleic acid sequences wherein each identifier comprises five components of 20 bases each. If all combinations of bases are available for synthesis, there may be up to $4^{20}$ possible sequences for each component.

The term "symbol," as used herein, generally refers to a representation of a unit of digital information. Digital information may be divided or translated into a string of symbols. In an example, a symbol may be a bit and the bit may have a value of '0' or '1'.

The term "distinct," or "unique," as used herein, generally refers to an object that is distinguishable from other objects in a group. For example, a distinct, or unique, nucleic acid sequence may be a nucleic acid sequence that does not have the same sequence as any other nucleic acid sequence. A distinct, or unique, nucleic acid molecule may not have the same sequence as any other nucleic acid molecule. The distinct, or unique, nucleic acid sequence or molecule may share regions of similarity with another nucleic acid sequence or molecule.

The term "component," as used herein, generally refers to a nucleic acid sequence or nucleic acid molecule. A component may comprise a distinct nucleic acid sequence. A component may be concatenated or assembled with one or more other components to generate other nucleic acid sequence or molecules.

The term "layer," as used herein, generally refers to group or pool of components. Each layer may comprise a set of distinct components such that the components in one layer are different from the components in another layer. Components from one or more layers may be assembled to generate one or more identifiers.

The term "identifier," as used herein, generally refers to a nucleic acid molecule or a nucleic acid sequence that represents the position and value of a bit-string within a larger bit-string. More generally, an identifier may refer to any object that represents or corresponds to a symbol in a string of symbols. In some implementations, identifiers may comprise one or multiple concatenated components.

The term "combinatorial space," as used herein generally refers to the set of all possible distinct identifiers that may be generated from a starting set of objects, such as components, and a permissible set of rules for how to modify those objects to form identifiers. The size of a combinatorial space of identifiers made by assembling or concatenating components may depend on the number of layers of components, the number of components in each layer, and the particular assembly method used to generate the identifiers.

The term "identifier rank," as used herein generally refers to a relation that defines the order of identifiers in a set.

The term "identifier library," as used herein generally refers to a collection of identifiers corresponding to the symbols in a symbol string representing digital information. In some implementations, the absence of a given identifier in the identifier library may indicate a symbol value at a particular position. One or more identifier libraries may be combined in a pool, group, or set of identifiers. Each identifier library may include a unique barcode that identifies the identifier library.

The term "probe," as used herein generally refers to an agent that binds a target sequence on an identifier nucleic acid molecule. The target sequence can be a portion of a component. The probe may comprise a sequence that matches or is the complement of its target sequence. The probe may be further used to isolate all identifier nucleic acid molecules comprising said target sequence. For example, the probe may be a primer in a PCR reaction that enriches all identifier nucleic acid molecules comprising a target sequence. Alternatively, the probe may contain be an affinity tagged oligonucleotide molecule that can be used to select all identifier nucleic acid molecules with a sequence that corresponds to said oligonucleotide.

The term "nucleic acid," as used herein, general refers to deoxyribonucleic acid (DNA), ribonucleic acid (RNA), or a variant thereof. A nucleic acid may include one or more subunits selected from adenosine (A), cytosine (C), guanine (G), thymine (T), and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that may be specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid is circular.

The terms "nucleic acid molecule" or "nucleic acid sequence," as used herein, generally refer to a polymeric form of nucleotides, or polynucleotide, that may have various lengths, either deoxyribonucleotides (DNA) or ribonucleotides (RNA), or analogs thereof. The term "nucleic acid sequence" refers to the alphabetical representation of a polynucleotide that defines the order of nucleotides; the term "nucleic acid molecule" refers to physical instance of the polynucleotide itself. This alphabetical representation can be input into databases in a computer having a central processing unit and used for mapping nucleic acid sequences or nucleic acid molecules to symbols, or bits, encoding digital information. Nucleic acid sequences or oligonucleotides may include one or more non-standard nucleotide(s), nucleotide analog(s) and/or modified nucleotides.

An "oligonucleotide", as used herein, generally refers to a single-stranded nucleic acid sequence, and is typically composed of a specific sequence of four nucleotide bases: adenine (A); cytosine (C); guanine (G), and thymine (T) or uracil (U) when the polynucleotide is RNA.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerase" or "polymerase enzyme," as used herein, generally refers to any enzyme capable of catalyzing a polymerase reaction. Examples of polymerases include, without limitation, a nucleic acid polymerase. The polymerase can be naturally occurring or synthesized. An example polymerase is a Φ29 polymerase or derivative thereof. In some cases, a transcriptase or a ligase is used (i.e., enzymes which catalyze the formation of a bond) in conjunction with polymerases or as an alternative to polymerases to construct new nucleic acid sequences. Examples of polymerases include a DNA polymerase, a RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof.

Digital information, such as computer data, in the form of binary code can comprise a sequence or string of symbols. A binary code may encode or represent text or computer processor instructions using, for example, a binary number system having two binary symbols, typically 0 and 1, referred to as bits. Digital information may be represented in the form of non-binary code which can comprise a sequence of non-binary symbols. Each encoded symbol can be re-assigned to a unique bit string (or "byte"), and the unique bit string or byte can be arranged into strings of bytes or byte streams. A bit value for a given bit can be one of two symbols (e.g., 0 or 1). A byte, which can comprise a string of N bits, can have a total of $2^N$ unique byte-values. For example, a byte comprising 8 bits can produce a total of $2^8$ or 256 possible unique byte-values, and each of the 256 bytes can correspond to one of 256 possible distinct symbols, letters, or instructions which can be encoded with the bytes. Raw data (e.g., text files and computer instructions) can be represented as strings of bytes or byte streams. Zip files, or compressed data files comprising raw data can also be stored in byte streams, these files can be stored as byte streams in a compressed form, and then decompressed into raw data before being read by the computer.

It is to be understood that the terms "index" and "position" are used interchangeably in the present disclosure, and it is to be understood that both terms are used to refer to a specific element or entity of an ordered collection, such as a list or a string. For example, an index or position may be used to specify an element in an array, vector, string, or data structure. Index/position notation uses a numbering scheme to assign nominal numbers to each entry/entity. The examples in the present disclosure often use a first index/position of 0, known in the art as zero-based numbering. The first position (also referred to as the zero-th position) of an array/string is denoted by 0 for purposes of computation involving the specific position). A set of length n would have a numbering scheme of 0, 1, . . . , n−1. It is to be understood that other numbering schemes may be used in the systems and methods described herein. For example, a numbering scheme may start at 1 and continue to n for a set of length n.

The present disclosure describes methods in relation to the figures of the application. It is to be understood that these methods, including computational steps, are configured to be performed in DNA. Methods and systems of the present disclosure may be used to encode computer data or information in a plurality of identifiers, each of which may represent one or more bits of the original information. In some examples, methods and systems of the present disclosure encode data or information using identifiers that each represents two bits of the original information.

Encoding and Writing Information to Nucleic Acid Sequences

The following description, in relation to FIGS. 1-10, provides an overview of various systems and methods for encoding data in nucleic acid molecules, and describes various writing and archival systems configured to print and store encoded nucleic acid molecules.

FIG. 1 illustrates an overview process for encoding information into nucleic acid sequences, writing information to the nucleic acid sequences, reading information written to nucleic acid sequences, and decoding the read information, according to an illustrative implementation. Digital information, or data, is represented as one or more strings of symbols. In an example, the symbols are bits, and each bit has a value of either '0' or '1'. Each symbol may be mapped, or encoded, to an object (e.g., identifier) representing that symbol, so that each symbol is represented by a distinct identifier. The distinct identifier may be one or more nucleic acid molecules having a specific nucleic acid sequence made up of component nucleic acid sequences (which may be referred to herein as components). To write the digital information into nucleic acid sequences, the process generates an "identifier library," which may be physically generated by physically constructing the identifiers that correspond to each symbol of the digital information. To read the digital information from the identifier library, the process accesses all or a subset of the identifiers in the identifier library, by sequencing and identifying the identifiers. Then, the identifiers that are identified are associated with their corresponding symbols, to decode the original digital data. In general, the present approach allows for all or any portion of the digital information to be accessed at a time.

In one example, a method for encoding and reading information using the approach of FIG. 1 includes receiving a bit stream and mapping each one-bit (bit with bit-value of '1') in the bit stream to a distinct nucleic acid identifier using an identifier rank or a nucleic acid index. Then, the process constructs the identifier library as pool of nucleic acid molecules that include copies of the identifiers that correspond to bit values of 1 (and excluding identifiers for bit values of 0). In other words, the identifier library includes multiple copies of each identifier that represents a one-bit at a specific position or rank in the bit stream, where each identifier is associated with multiple instances of identifier molecules in the pool, that share a specific sequence that represents the specific position or rank in the bit stream, while identifiers that represent zero-bits in the bit stream are excluded from the pool. In order to read the digital data from the pool of nucleic acid molecules, molecular biology methods (e.g., sequencing, hybridization, PCR, etc) may be used to determine which identifiers are represented in the identifier library. For the identifiers that are present in the identifier library, the corresponding identifier rank (and thus bit-position in the bit stream) is determined, and a bit-value of '1' is assigned to that location. For any identifiers that are absent from the identifier library, the corresponding identifier rank (and thus bit-position in the bit stream) is determined, and a bit-value of '0' is assigned to that location. In this manner, the pool of nucleic acid molecules can be decoded to determine the original encoded bit stream.

The approach described above involves encoding a string of N distinct bits, with an equivalent number N of unique nucleic acid sequences as possible identifiers. This approach to information encoding may use de novo synthesis of identifiers (e.g., nucleic acid molecules) for each new item of information (another string of N bits) to store. In other instances, the cost of newly synthesizing identifiers (equivalent in number to or less than N) for each new item of information to store can be reduced to the one-time de-novo synthesis and subsequent maintenance of all possible N identifiers. In this way, encoding new items of information (e.g., bit strings of length N or less) involves mechanically selecting and mixing together pre-synthesized (or pre-fabricated) identifiers to form an identifier library. In other instances, the cost of (1) de-novo synthesis of up to N identifiers for each new item of information to store or (2) maintaining and selecting from N possible identifiers for each new item of information to store, or both, may be reduced by synthesizing and maintaining a number (less than N, and in some cases much less than N) of nucleic acid sequences and then modifying these sequences through enzymatic reactions to generate up to N identifiers for each new item of information to store. For example, the nucleic acid sequences that are synthesized and maintained may correspond to specific portions that make up the N identifiers, such as components.

The identifiers may be rationally designed and selected for ease of read, write, access, copy, and deletion operations. The identifiers may be designed and selected to minimize write errors, mutations, degradation, and read errors.

As a specific example, the set of available identifier sequences may include 15 layers, 14 layers of which each contain six unique DNA component sequences. The $15^{th}$ layer may be a multiplex layer comprising 28 DNA component sequences (rather than six) which will also be incorporated. Thus, each identifier may contain 15 components (one component in each layer) in the full-length identifier nucleic acid molecule. During the writing process, the component molecules are assembled together in reaction compartments to form identifier molecules. In some implementations, multiple components from only the "multiplex layer" will be combined into the same reaction compartment.

As another example, to write one terabyte in 86,400 seconds (24 hours), approximately $8 \times 10^{11}$ identifier molecules may need to be assembled (assuming 10 bits of information encoded per identifier), or approximately $5 \times 10^{10}$ droplet reaction compartments. Each reaction may assemble fourteen identifiers from a possible set of 28 identifiers. Fourteen components (one from each of the 14 layers each with six possible components) specify and assemble the "base" of the identifiers. A remaining fourteen components out of 28 possible components from the multiplex layer specify which fourteen identifiers (out of 28 possibilities) will be assembled. Thus, each reaction compartment may need 28 DNA components, plus ligase or other reaction mix.

The methods described herein may be implemented using a writing system, as described below. The writing system may be a printer-finisher system such as that described in U.S. application Ser. No. 16/414,752 filed May 16, 2019, entitled Printer-Finisher System for Data Storage in DNA, which is hereby incorporated by reference. The writer system may dispense DNA components at discrete locations (e.g., reaction compartments) on a substrate, dispense ligation master mix, provide optimal conditions for the ligation reaction, and pool all of the DNA identifiers that comprise a library.

The writing systems described herein are capable of executing high-throughput, parallelized printing of ligation reactions for constructing identifiers. Reactions may be carried out in picoliter (pL)-scale droplets printed onto flexible sheets (also referred to as webbing or substrates) moving over rollers. As described in the above-referenced application, the writing systems may incorporate technologies such as digital inkjet printing and web handling, using suitable off-the-shelf print heads, drivers, and machine infrastructure. In some implementations, the systems and methods described herein include optimization of factors such as web speed, print head dispense speed, droplet size, and ligation chemistry to achieve storage capacity and write throughput. To this end, and to ensure data tolerance to potential chemistry and hardware errors, the systems and methods described herein include configurations to encode the data and develop printing instructions, including specifications for how to partition DNA component sequences into layers and how many identifier molecules to construct in each printed reaction. For example, such configurations may include computer systems that communicate with the writing system and track its performance.

Figure 2A:
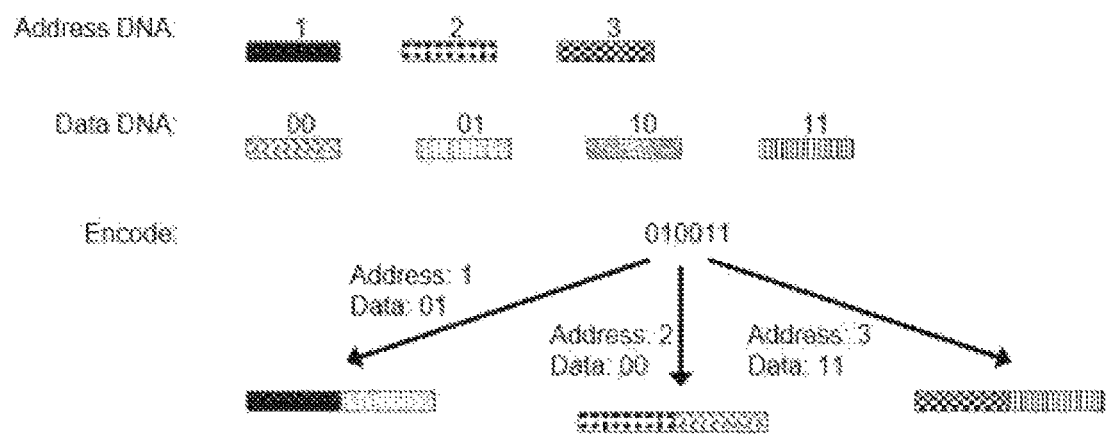
Figure 2B:
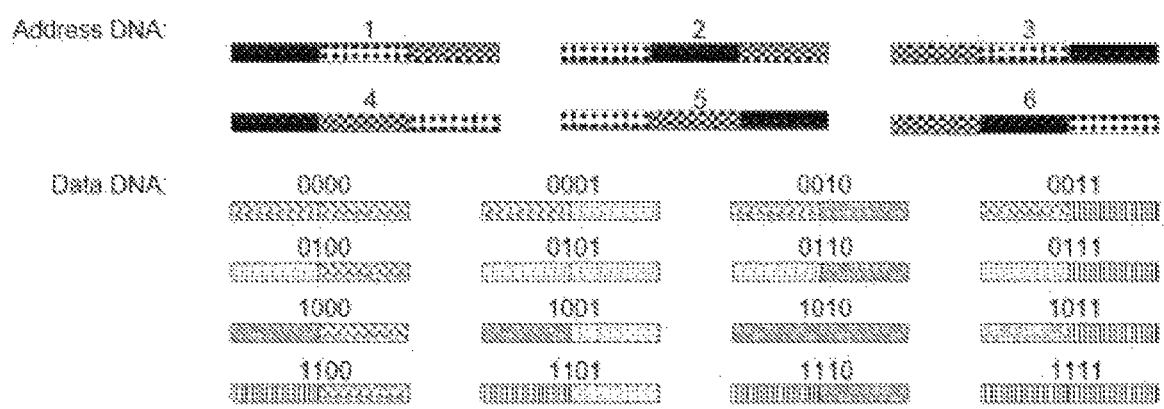

FIGS. 2A and 2B schematically illustrate an example method, referred to as "data at address", of encoding digital data in objects or identifiers (e.g., nucleic acid molecules), according to an illustrative implementation. FIG. 2A illustrates encoding a bit stream into an identifier library wherein the individual identifiers are constructed by concatenating or assembling a single component that specifies an identifier rank with a single component that specifies a byte-value. In general, the data at address method uses identifiers that encode information modularly by comprising two objects: one object, the "byte-value object" (or "data object"), that identifies a byte-value and one object, the "rank object" (or "address object"), that identifies the identifier rank (or the relative position of the byte in the original bit-stream). FIG. 2B illustrates an example of the data at address method wherein each rank object may be combinatorially constructed from a set of components and each byte-value object may be combinatorially constructed from a set of components. Such combinatorial construction of rank and byte-value objects enables more information to be written into identifiers than if the objects where made from the single components alone (e.g., FIG. 2A).

Figure 3A:
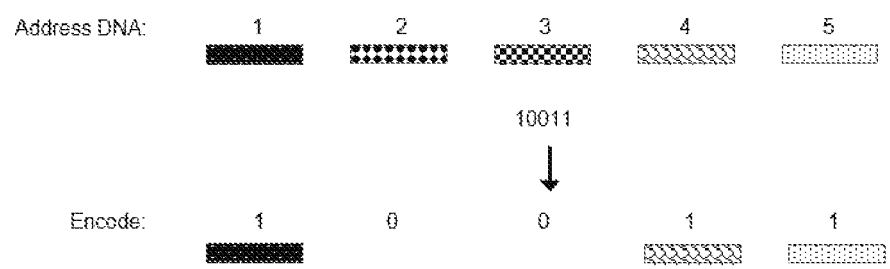
Figure 3B:
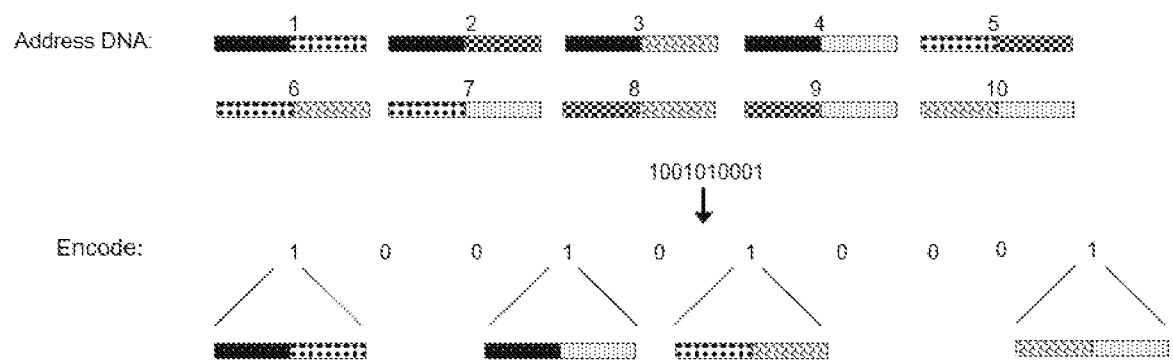

FIGS. 3A and 3B schematically illustrate another example method of encoding digital information in objects or identifiers (e.g., nucleic acid sequences), according to an illustrative implementation. FIG. 3A illustrates encoding a bit stream into an identifier library wherein identifiers are constructed from single components that specify identifier rank, corresponding to a position in the bit stream. The presence of an identifier at a particular rank (or address) specifies a bit-value of '1' and the absence of an identifier at a particular rank (or address) specifies a bit-value of '0'. This type of encoding may use identifiers that solely encode rank (the relative position of a bit in the original bit stream) and use the presence or absence of those identifiers in an identifier library to encode a bit-value of '1' or '0', respectively. Reading and decoding the information may include identifying the identifiers present in the identifier library, assigning bit-values of '1' to their corresponding ranks and assigning bit-values of '0' elsewhere. While the presence of an identifier encodes a one-bit and an absence of an identifier encodes a zero-bit in the example, it will be understood that the presence of an identifier could encode a zero-bit while an absence of an identifier encodes a one-bit, without departing from the scope of the present disclosure.

FIG. 3B is similar to FIG. 3A, but in the example encoding method of FIG. 3B, each identifier is combinatorially constructed from a set of components such that each possible combinatorial construction specifies a rank. Such combinatorial construction enables more information to be written into identifiers than if the identifiers where made from the single components alone (e.g., FIG. 3A). For example, as depicted in FIG. 3B, the ten addresses, corresponding to a bit string of length N=10, are represented using a component set of five distinct components. The five distinct components are assembled in a combinatorial manner to generate ten distinct identifiers, each comprising two of the five components. The ten distinct identifiers each have a rank (or address) that corresponds to the position of a bit in a bit stream. An identifier library may include the subset of those ten possible identifiers that corresponds to the positions of bit-value '1', and exclude the subset of those ten possible identifiers that corresponds to the positions of the bit-value '0' within a bit stream of length ten.

Figure 4:
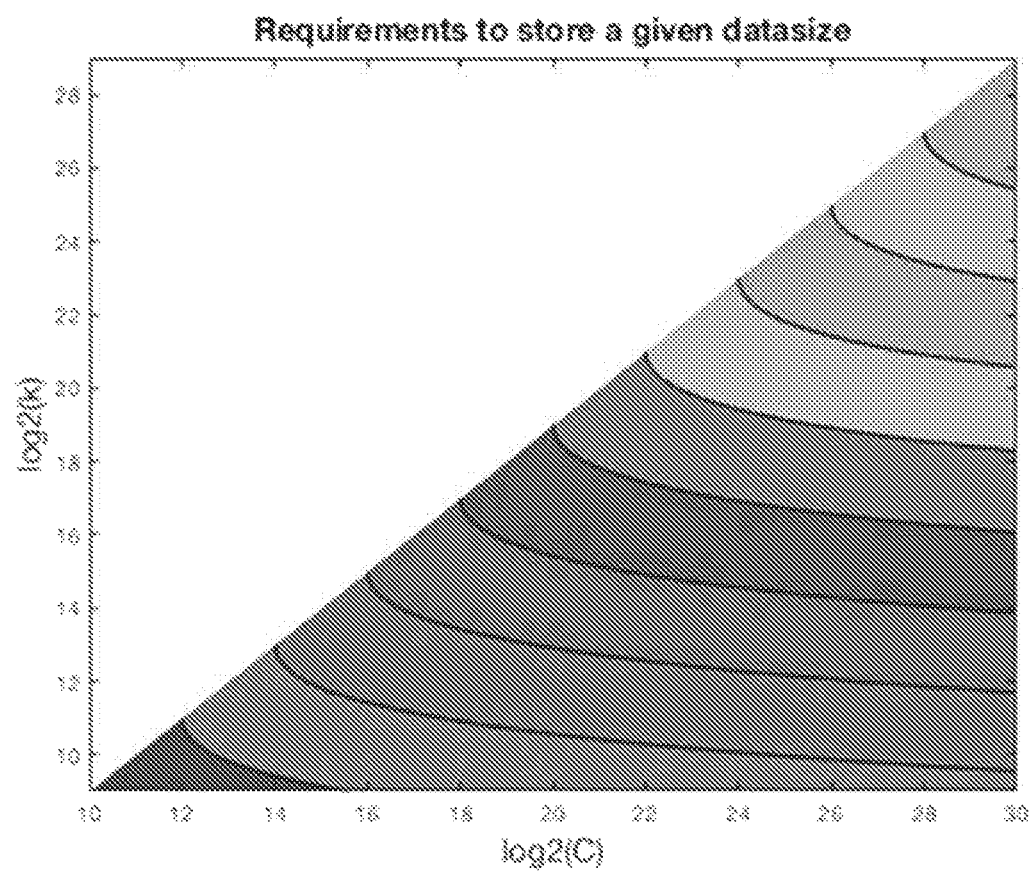

FIG. 4 shows a contour plot, according to an illustrative implementation, in log space, of a relationship between the combinatorial space of possible identifiers (C, x-axis) and the average number of identifiers (k, y-axis) to be physically constructed in order to store information of a given original size in bits (D, contour lines) using the encoding method shown in FIGS. 3A and 3B. This plot assumes that the original information of size D is re-coded into a string of C bits (where C may be greater than D) where a specified number of bits, k, have a bit-value of '1'. Moreover, the plot assumes that information-to-nucleic-acid encoding is performed on the re-coded bit string and that identifiers for positions where the bit-value is '1' are constructed and identifiers for positions where the bit-value is '0' are not constructed. Following the assumptions, the combinatorial space of possible identifiers has size C to identify every position in the re-coded bit string, and the number of identifiers used to encode the bit string of size D is such that D=log 2(Cchoosek), where Cchoosek is the number of ways to pick k unordered outcomes from C possibilities. Thus, as the combinatorial space of possible identifiers increases beyond the size (in bits) of a given item of information, a decreasing number of physically constructed identifiers are necessary to store the given information.

Figure 5:
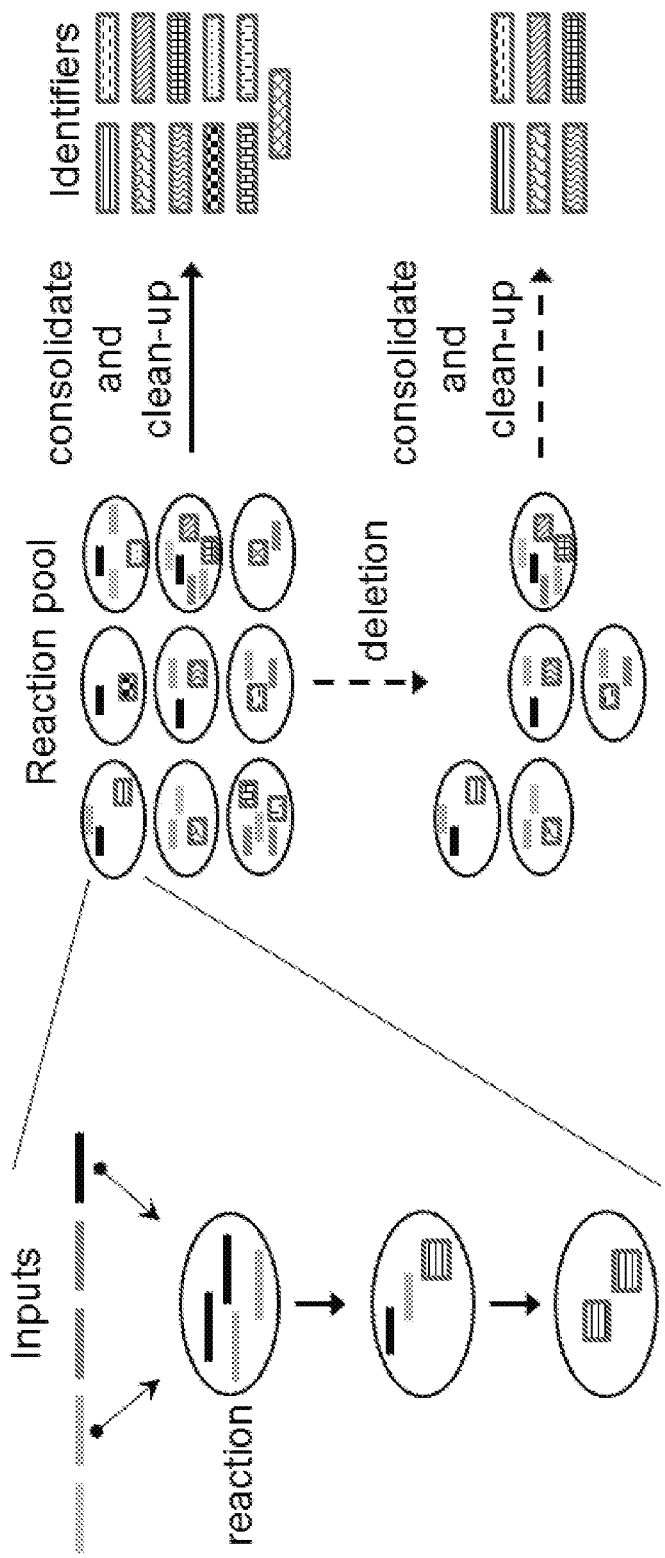

FIG. 5 shows an overview method for writing information into nucleic acid sequences, according to an illustrative implementation. Prior to being written into nucleic acid molecules, the information is translated into a string of symbols and encoded into a plurality of identifier sequences, according to an illustrative implementation. In an example, writing the information into nucleic acid molecules includes setting up various chemical reactions to produce identifier molecules for combining in a pool. Specifically, a reaction is set up by depositing inputs (such as nucleic acids, components, templates, enzymes, or chemical reagents, for example) into a compartment (also referred to as a container herein, such as a well, a tube, a position on a surface, a chamber in a microfluidic device, or a droplet within an emulsion, for example). Reactions may be set up in a single compartment at a time, or may be set up in multiple compartments for parallel processing. The reactions may include specific process steps, such as programmed temperature incubation or cycling, may be selectively or ubiquitously removed (e.g., deleted), may be selectively or ubiquitously interrupted, consolidated, and purified to collect the resulting identifier molecules in one pool, or any suitable combination thereof. Identifiers from multiple identifier libraries may be collected in the same pool, or different identifier libraries may each be collected in separate individual pools. In some examples, an individual identifier includes a unique barcode or a tag to identify the corresponding identifier library to which it belongs. In some examples, that barcode includes metadata representative of the encoded information. In addition to the identifier molecules that represent the encoded information itself, supplemental nucleic acids or additional identifiers may also be included in an identifier pool together with an identifier library. For example, the supplemental nucleic acids or additional identifiers may represent metadata for the encoded information or serve to obfuscate or conceal the encoded information.

An identifier rank (e.g., nucleic acid index) is based on an ordering of identifiers. The method can comprise a look-up table with all identifiers and their corresponding rank. The method can also comprise a look up table with the rank of all components that constitute identifiers and a function for determining the ordering of any identifier comprising a combination of those components. Such a method may be referred to as lexicographical ordering and may be analogous to the manner in which words in a dictionary are alphabetically ordered. For example, Each identifier in a combinatorial space can comprise a fixed number of N components where each component comes from a distinct layer in a set of N layers, and is one of a number of a set of possible components in said layer. Each component can be specified by a coordinate $(j, X_j)$ where j is the label of the layer and $X_j$ is the label of the component within the layer. For said scheme with N layers, j is an element of the set $\{1, 2, \ldots, N\}$ and $X_j$ is an element of the set $\{1, 2, \ldots, M_j\}$ where $M_j$ is the number of components in layer j. We can define a logical order to the layers. We can also define a logical order to each component within each layer. We can use this labeling to define a logical ordering to all possible identifiers in the combinatorial space through a function or algorithm. For example, we can first sort the identifiers according to the order of the components in layer 1, and then subsequently according to the order of the components in layer 2, and so on.

In the data-at-address encoding method, the identifier rank (encoded by the rank object of the identifier) may be used to determine the position of a byte (encoded by the byte-value object of the identifier) within a bit stream. In an alternative method, the identifier rank (encoded by the entire identifier itself) for a present identifier may be used to determine the position of bit-value of '1' within a bit stream. Systems and methods that describe various ways to determine the specific rank or use the rank of one or more identifiers are described in relation to FIGS. 23-29.

A key may assign distinct bytes or portions of information to unique subsets of identifiers (e.g., nucleic acid molecules) within a sample. For example, in a simple form, a key may assign each bit in a byte to a unique nucleic acid sequence that specifies the position of the bit, and then the presence or absence of that nucleic acid sequence within a sample may specify the bit-value of 1 or 0, respectively. Other types of keys may also be used, without departing from the scope of the present disclosure. Reading the encoded information from the nucleic acid sample can comprise any number of molecular biology techniques including sequencing, hybridization, or PCR. In some implementations, reading the encoded dataset may comprise reconstructing a portion of the dataset or reconstructing the entire encoded dataset from each nucleic acid sample. When the sequence is read, the nucleic acid index is determined, along with the presence or absence of a unique nucleic acid sequence and the nucleic acid sample can be decoded into a bit stream (e.g., each string of bits, byte, bytes, or string of bytes).

In some implementations, identifiers are constructed by combinatorially assembling component nucleic acid sequences. For example, information may be encoded by taking a set of nucleic acid molecules (e.g., identifiers) from a defined group of molecules (e.g., combinatorial space). Each possible identifier of the defined group of molecules may be an assembly of nucleic acid sequences (e.g., components) from a prefabricated set of components that may be divided into layers. Each individual identifier may be constructed by concatenating one component from every layer in a fixed order. For example, if there are M layers and each layer may have n components, then up to $C=n^M$ unique identifiers may be constructed and up to 2c different items of information, or C bits, may be encoded and stored. For example, storage of a megabit of information may use $1\times10^6$ distinct identifiers or a combinatorial space of size $C=1\times10^6$. The identifiers in this example may be assembled from a variety of components organized in different ways. Assemblies may be made from M=2 prefabricated layers, each containing $n=1\times10^3$ components. Alternatively, assemblies may be made from M=3 layers, each containing $n=1\times10^2$ components. In some implementations, assemblies may be made from M=2, M=3, M=4, M=5 or more layers. As this example illustrates, encoding the same amount of information using a larger number of layers may allow for the total number of components to be smaller. Using a smaller number of total components may be advantageous in terms of writing cost.

In an example, there are two sets of unique nucleic acid sequences or layers, X and Y, each with x and y components (e.g., nucleic acid sequences), respectively. Each nucleic acid sequence from X can be assembled to each nucleic acid sequence from Y. Though the total number of nucleic acid sequences maintained in the two sets is the sum of x and y, the total number of nucleic acid molecules, and hence possible identifiers, that can be generated is the product of x and y. Even more nucleic acid sequences (e.g., identifiers) can be generated if the sequences from X can be assembled to the sequences of Y in any order. For example, the number of nucleic acid sequences (e.g., identifiers) generated may be twice the product of x and y if the assembly order is programmable. This set of all possible nucleic acid sequences that can be generated may be referred to as XY. The order of the assembled units of unique nucleic acid sequences in XY can be controlled using nucleic acids with distinct 5' and 3' ends, and restriction digestion, ligation, polymerase chain reaction (PCR), and sequencing may occur with respect to the distinct 5' and 3' ends of the sequences. Accordingly, all the units and necessary reagents may be deposited simultaneously in a reaction compartment, and the distinct 5' and 3' ends on each unit allow the units (e.g., components) to self-assemble into the desired unique nucleic acid molecules, because the order of assembled units is controlled by design of the ends. Such an approach can reduce the total number of nucleic acid sequences (e.g., components) used to encode N distinct bits, by encoding information in the combinations and orders of their assembly products. For example, to encode 100 bits of information, two layers of 10 distinct nucleic acid molecules (e.g., component) may be assembled in a fixed order to produce $10^2$ or 100 distinct nucleic acid molecules (e.g., identifiers), or one layer of 5 distinct nucleic acid molecules (e.g., components) and another layer of 10 distinct nucleic acid molecules (e.g., components) may be assembled in any order to produce 100 distinct nucleic acid molecules (e.g., identifiers).

Nucleic acid sequences (e.g., components) within each layer may comprise a unique (or distinct) sequence, or barcode, in the middle, a common hybridization region on one end, and another common hybridization region on another other end. The barcode may contain a sufficient number of nucleotides to uniquely identify every sequence within the layer. For example, there are typically four possible nucleotides for each base position within a barcode. Therefore, a three base barcode may uniquely identify $4^3=64$ nucleic acid sequences. The barcodes may be designed to be randomly generated. Alternatively, the barcodes may be designed to avoid sequences that may create complications to the construction chemistry of identifiers or sequencing. Additionally, barcodes may be designed so that each may have a minimum hamming distance from the other barcodes, thereby decreasing the likelihood that base-resolution mutations or read errors may interfere with the proper identification of the barcode. Also, the barcode region may be designed to bind a probe, such as a primer for PCR, a CRISPR-Cas guide RNA, or an affinity tagged oligonucleotide (for example, a biotinylated oligonucleotide).

The hybridization region on one end of the nucleic acid sequence (e.g., component) may be different in each layer, but the hybridization region may be the same for each member within a layer. Adjacent layers are those that have complementary hybridization regions on their components that allow them to interact with one another. For example, any component from layer X may be able to attach to any component from layer Y because they may have complementary hybridization regions. The hybridization region on the opposite end may serve the same purpose as the hybridization region on the first end. For example, any component from layer Y may attach to any component of layer X on one end and any component of layer Z on the opposite end. Accordingly, all the components and necessary reagents to form a plurality of identifiers may be deposited simultaneously in a reaction compartment, and the hybridization regions on each component allow them to self-assemble into the desired unique identifier molecules, because the order of assembled components is controlled by design of the hybridization regions.

Figure 6A:
Figure 6B:
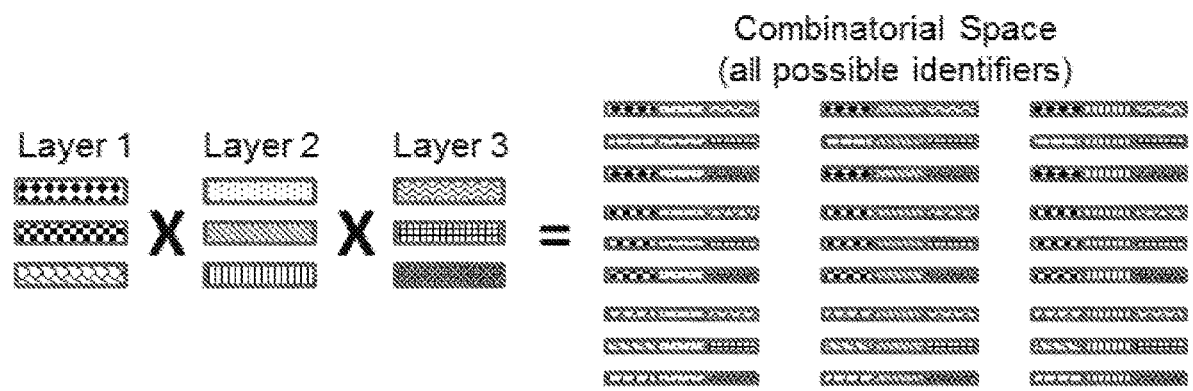

FIGS. 6A and 6B illustrate an example method, referred to as the "product scheme", for constructing identifiers (e.g., nucleic acid molecules) by combinatorially assembling a distinct component (e.g., nucleic acid sequence) from each layer in a fixed order, according to an illustrative implementation. FIG. 6A illustrates the architecture of identifiers constructed using the product scheme. An identifier may be constructed by combining a single component from each layer in a fixed order. For M layers, each with N components, there are $N^M$ possible identifiers. FIG. 6B illustrates an example of the combinatorial space of identifiers that may be constructed using the product scheme. In an example, a combinatorial space may be generated from three layers each comprising three distinct components. The components may be combined such that one component from each layer may be combined in a fixed order. The entire combinatorial space for this assembly method may comprise twenty-seven possible identifiers.

FIGS. 7-10 illustrate chemical methods for implementing the product scheme (see FIG. 6). Methods depicted in FIGS. 7-10, along with any other methods for assembling two or more distinct components in a fixed order may be used, for example, to produce any one or more identifiers in an identifier library. These methods are described in U.S. Pat. No. 10,650,312 entitled "NUCLEIC ACID-BASED DATA STORAGE", filed Dec. 21, 2017, which is incorporated by reference in its entirety. Identifiers may be constructed using any of the implementation methods described in FIGS. 7-10, at any time during the methods or systems disclosed herein. In some instances, all or a portion of the combinatorial space of possible identifiers may be constructed before digital information is encoded or written, and then the writing process may involve mechanically selecting and pooling the identifiers (that encode the information) from the already existing set. In other instances, the identifiers may be constructed after one or more steps of the data encoding or writing process may have occurred (i.e., as information is being written).

Enzymatic reactions may be used to assemble components from the different layers or sets. Assembly can occur in a one pot reaction because components (e.g., nucleic acid sequences) of each layer have specific hybridization or attachment regions for components of adjacent layers. For example, a nucleic acid sequence (e.g., component) X1 from layer X, a nucleic acid sequence Y1 from layer Y, and a nucleic acid sequence Z1 from layer Z may form the assembled nucleic acid molecule (e.g., identifier) X1Y1Z1. Additionally, multiple nucleic acid molecules (e.g., identifiers) may be assembled in one reaction by including multiple nucleic acid sequences from each layer. The one reaction may involve self-assembly of components into identifiers.

Figure 7:
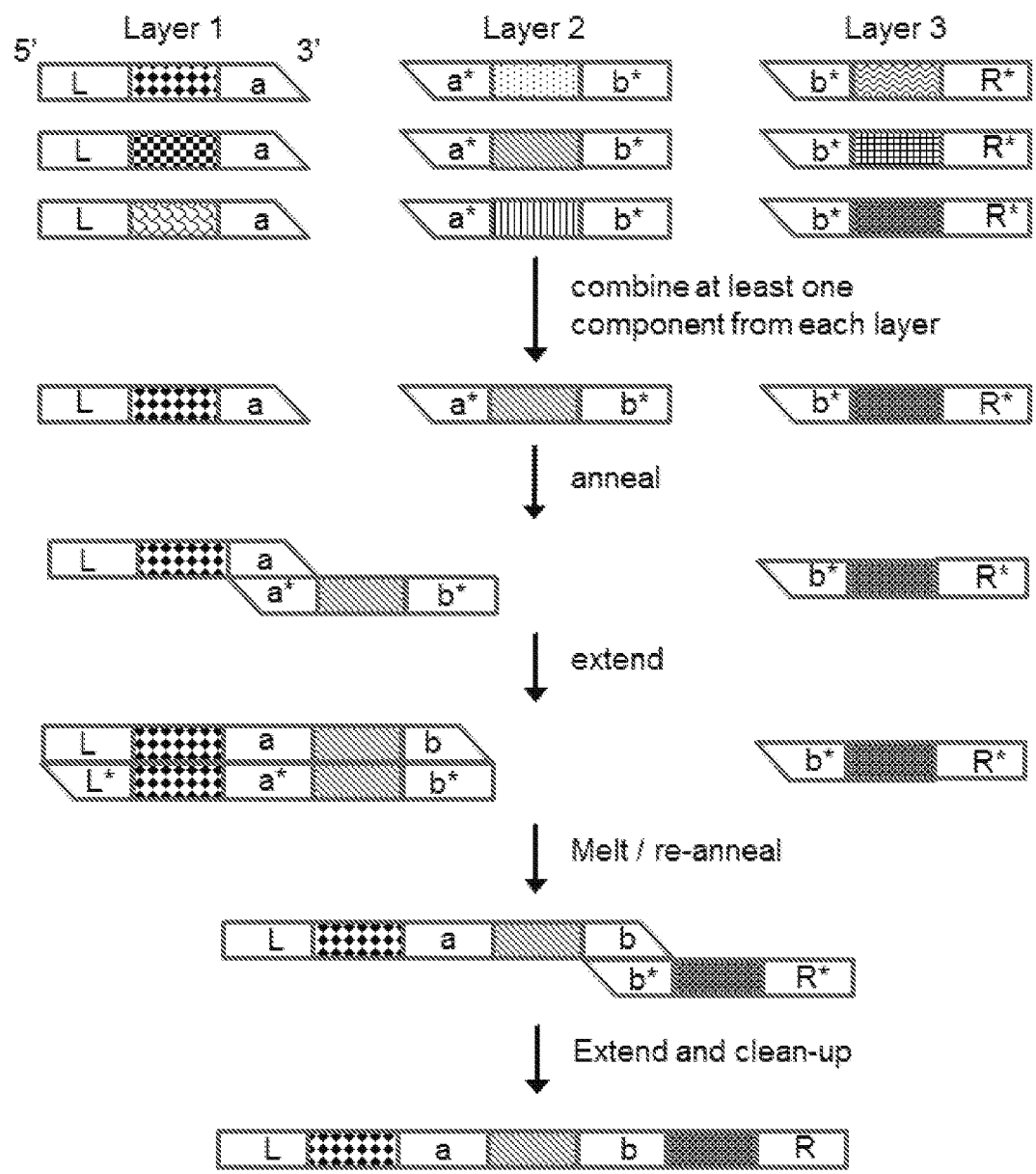

Identifiers may be constructed in accordance with the product scheme using overlap extension polymerase chain reaction (OEPCR), as illustrated in FIG. 7, according to an illustrative implementation. Each component in each layer may comprise a double-stranded or single stranded (as depicted in the figure) nucleic acid sequence with a common hybridization region on the sequence end that may be homologous and/or complementary to the common hybridization region on the sequence end of components from an adjacent layer. Accordingly, all the components and necessary reagents to form a plurality of identifiers may be deposited simultaneously in a reaction compartment, and the hybridization regions on each component allow them to self-assemble into the desired unique identifier molecules, because the order of assembled components is controlled by design of the hybridization regions.

Figure 8:
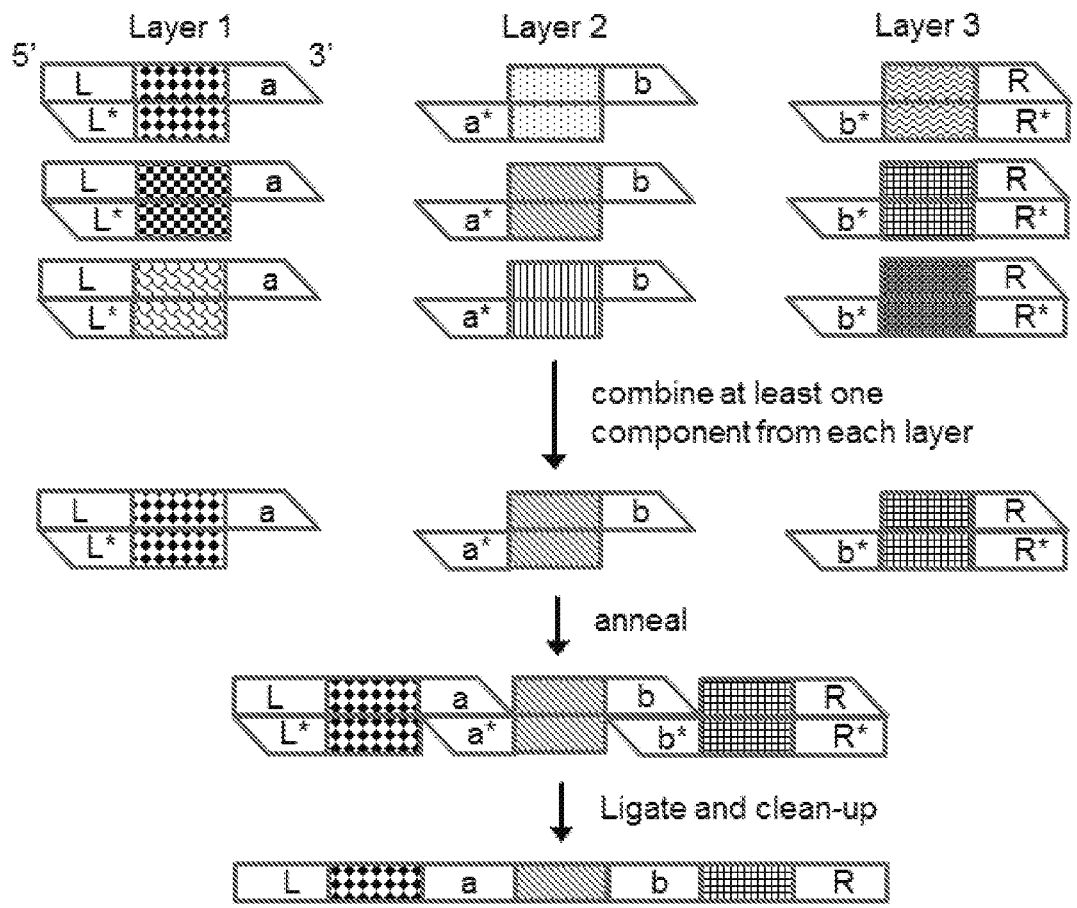

Identifiers may be assembled in accordance with the product scheme using sticky end ligation, as illustrated in FIG. 8, according to an illustrative implementation. Three layers, each comprising double stranded components (e.g., double stranded DNA (dsDNA)) with single-stranded 3' overhangs, can be used to assemble distinct identifiers. The sticky ends for sticky end ligation may be generated by treating the components of each layer with restriction endonucleases. In some implementations, the components of multiple layers may be generated from one "parent" set of components.

Figure 9:
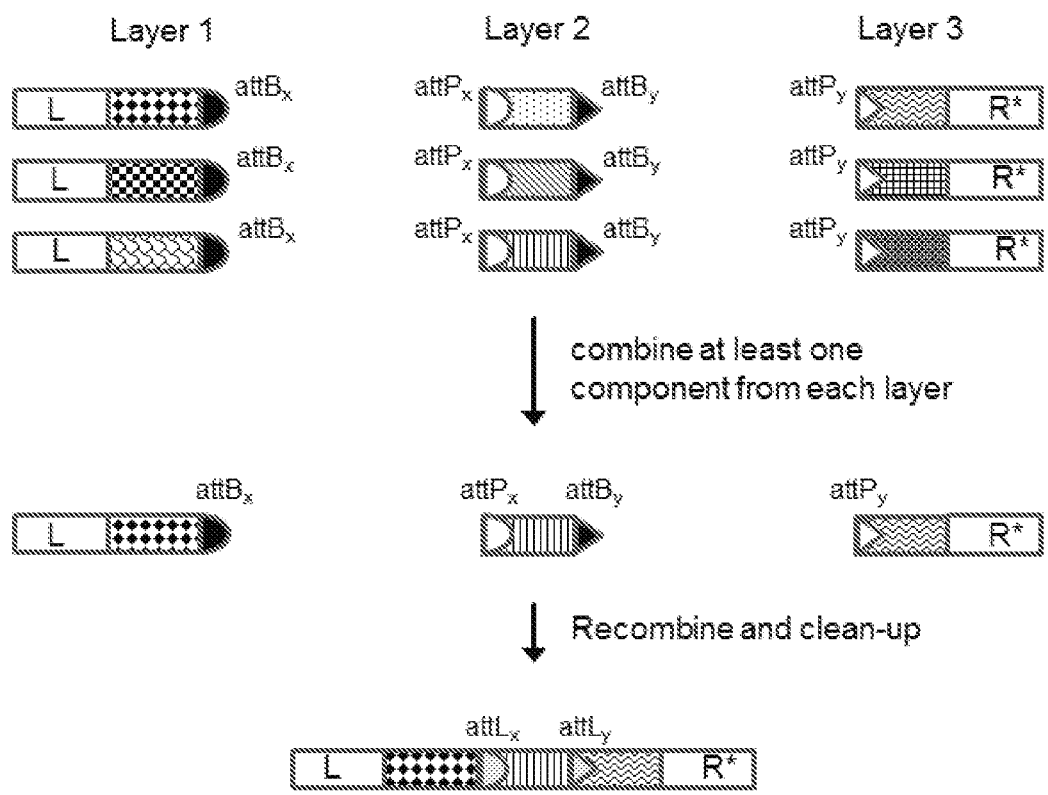

Identifiers may be assembled in accordance with the product scheme using site specific recombination, as illustrated in FIG. 9, according to an illustrative implementation. Identifiers may be constructed by assembling components from three different layers. The components in layer X (or layer 1) may comprise double-stranded molecules with an attBx recombinase site on one side of the molecule, components from layer Y (or layer 2) may comprise double-stranded molecules with an $attP_x$ recombinase site on one side and an $attB_y$ recombinase site on the other side, and components in layer Z (or layer 3) may comprise an $attP_y$ recombinase site on one side of the molecule. attB and attP sites within a pair, as indicate by their subscripts, are capable of recombining in the presence of their corresponding recombinase enzyme. One component from each layer may be combined such that one component from layer X associates with one component from layer Y, and one component from layer Y associates with one component from layer Z. Accordingly, all the components and necessary reagents to form a plurality of identifiers may be deposited simultaneously in a reaction compartment, and the recombinase sites on each component allow them to self-assemble into the desired unique identifier molecules, because the order of assembled components is controlled by design of the recombinase sites.

Figure 10A:
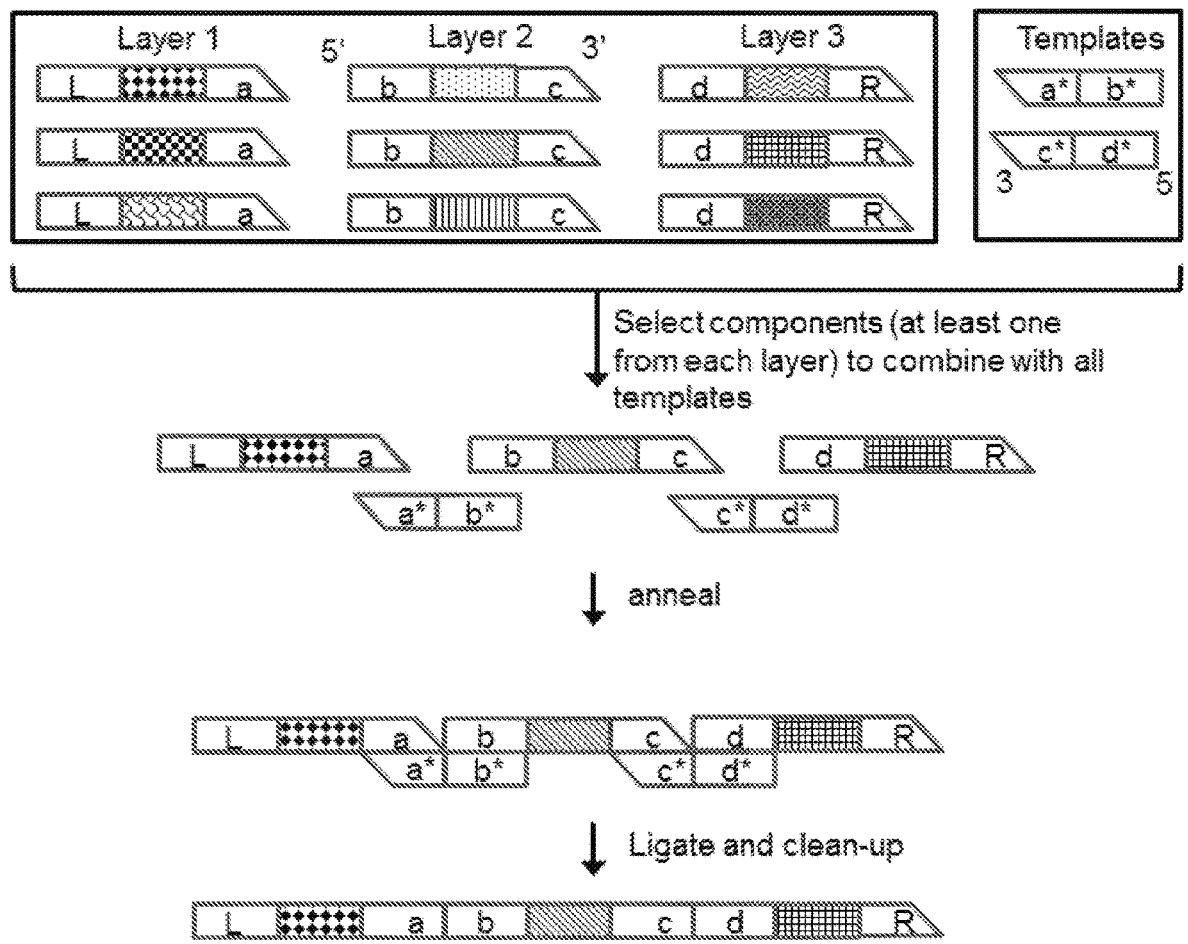

Identifiers may be constructed in accordance with the product scheme using template directed ligation (TDL), as shown in FIG. 10A, according to an illustrative implementation. Template directed ligation utilizes single stranded nucleic acid sequences, referred to as "templates" or "staples", to facilitate the ordered ligation of components to form identifiers. The templates simultaneously hybridize to components from adjacent layers and hold them adjacent to each other (3' end against 5' end) while a ligase ligates them. Accordingly, all the components and necessary reagents to form a plurality of identifiers may be deposited simultaneously in a reaction compartment, and the hybridization regions on each component allow them to self-assemble into the desired unique identifier molecules, because the order of assembled components is controlled by design of the templates.

Figure 10B:
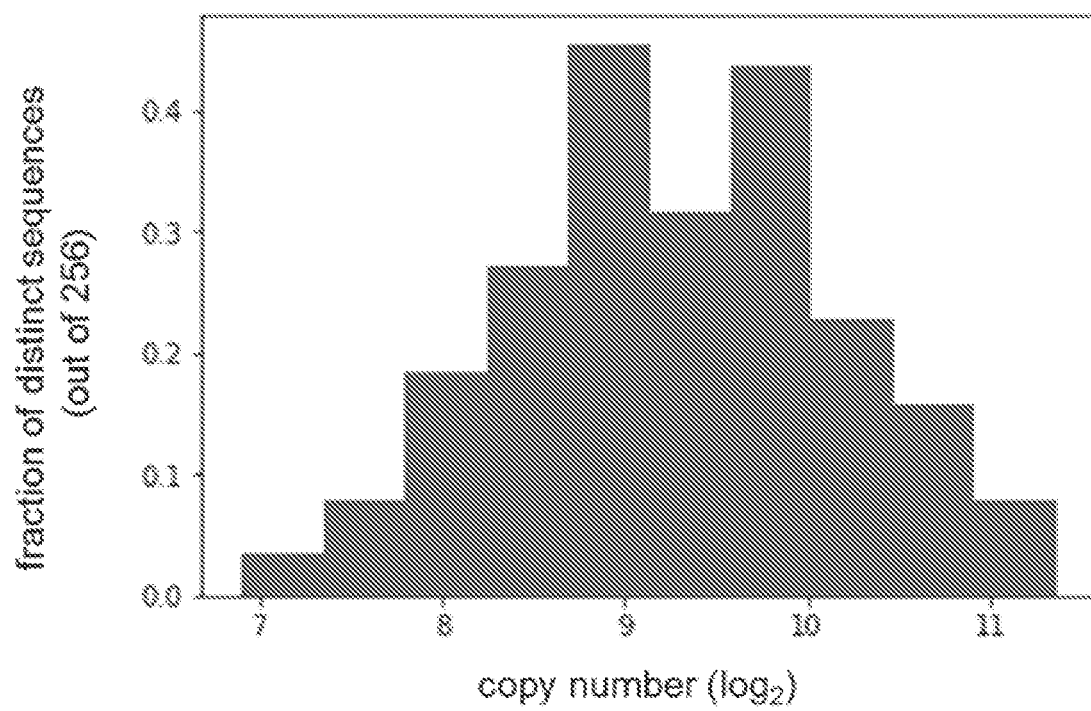

FIG. 10B shows a histogram of the copy numbers (abundances) of 256 distinct nucleic acid sequences that were each assembled with 6-layer TDL, according to an illustrative implementation. The edge layers (first and final layers) each had one component, and each of the internal layers (remaining 4 four layers) had four components. Each edge layer component was 28 bases including a 10 base hybridization region. Each internal layer component was 30 bases including a 10 base common hybridization region on the 5' end, a 10 base variable (barcode) region, and a 10 base common hybridization region on the 3' end. Each of the three template strands was 20 bases in length. All 256 distinct sequences were assembled in a multiplex fashion with one reaction containing all of the components and templates, T4 Polynucleotide Kinase (for phosphorylating the components), and T4 Ligase, ATP, and other proper reaction reagents. The reaction was incubated at 37 degrees for 30 minutes and then room temperature for 1 hour. Sequencing adapters were added to the reaction product with PCR, and the product was sequenced with an Illumina MiSeq instrument. The relative copy number of each distinct assembled sequence out of 192910 total assembled sequence reads is shown. Other implementations of this method may use double stranded components, where the components are initially melted to form single stranded versions that can anneal to the staples. Other implementations or derivatives of this method (i.e., TDL) may be used to construct a combinatorial space of identifiers more complex than what may be accomplished in the product scheme. Identifiers may be constructed in accordance with the product scheme using various other chemical implementations including golden gate assembly, gibson assembly, and ligase cycling reaction assembly.

Data Structures and Data Blocks for Efficient Data Storage in Nucleic Acid Sequences This section discusses systems and methods for encoding data in DNA in an efficient manner, and is in relation to FIGS. 11-19. In particular, certain data structures and control schemes are described. A data structure includes a format for data organization, management, and/or storage that enables efficient access and modification of the stored data. More precisely, a data structure includes a collection of data values, the relationships among them, and the functions or operations that can be applied to the data. Exemplary data structures and encoding schemes are described in U.S. application Ser. No. 16/532,077 entitled "SYSTEMS AND METHODS FOR STORING AND READING NUCLEIC ACID-BASED DATA WITH ERROR PROTECTION", filed Aug. 5, 2019, which is hereby incorporated by reference in its entirety. By encoding DNA with the these structures or schemes, stored data may be more easily accessed or manipulated.

As discussed above, a string may be encoded as a library of identifiers which represent positions of 1-bits in the string or symbols in a symbol string. However, an extra translation layer may be employed by using "codewords" and "codebooks". A "codeword" is a group of $n_c$ consecutive identifiers in an ordered identifier library and encodes a symbol (e.g., of an arbitrary alphabet) by setting only $k_c$ identifiers out of the $n_c$ available identifiers. The value of $k_c$ is called the "weight" of the codeword. The "codebook" is the set of all possible codewords. For example, the systems and methods described herein may use a codebook that encodes 6 bits of data in every contiguous group of 8 identifiers. In this example, the codebook could map each possible string of 6 bits to a unique subsets of $k_c$=4 out of the $n_c$=8 identifiers (since there are 8 choose 4=70 such subsets, it is possible to store up to floor($\log_2(70)$)=6 bits of data). These identifier combinations are referred to as codewords, and he data that they encode is referred to as words. Adjacent words within data may be stored in adjacent codewords among the logically ordered identifiers. Codewords can be represented symbolically as bit strings where every bit position corresponds to an ordered identifier, where the bit-value of '0' represents the absence of the corresponding identifier in the codeword and the bit-value of '1' represents the presence of the corresponding identifier in the codeword. Codebooks may be "low-weight" or "high-weight," where, for example, a low-weight codebook may set 2 out of 25 identifiers, and a high-weight codebook may set 178 out of 357 identifiers. High-weight codebooks may allow for higher density data storage (i.e., more bits stored per library), but low-weight codebooks may allow for better implementation of error-correction schemes and more robust encoders.

Figure 11:
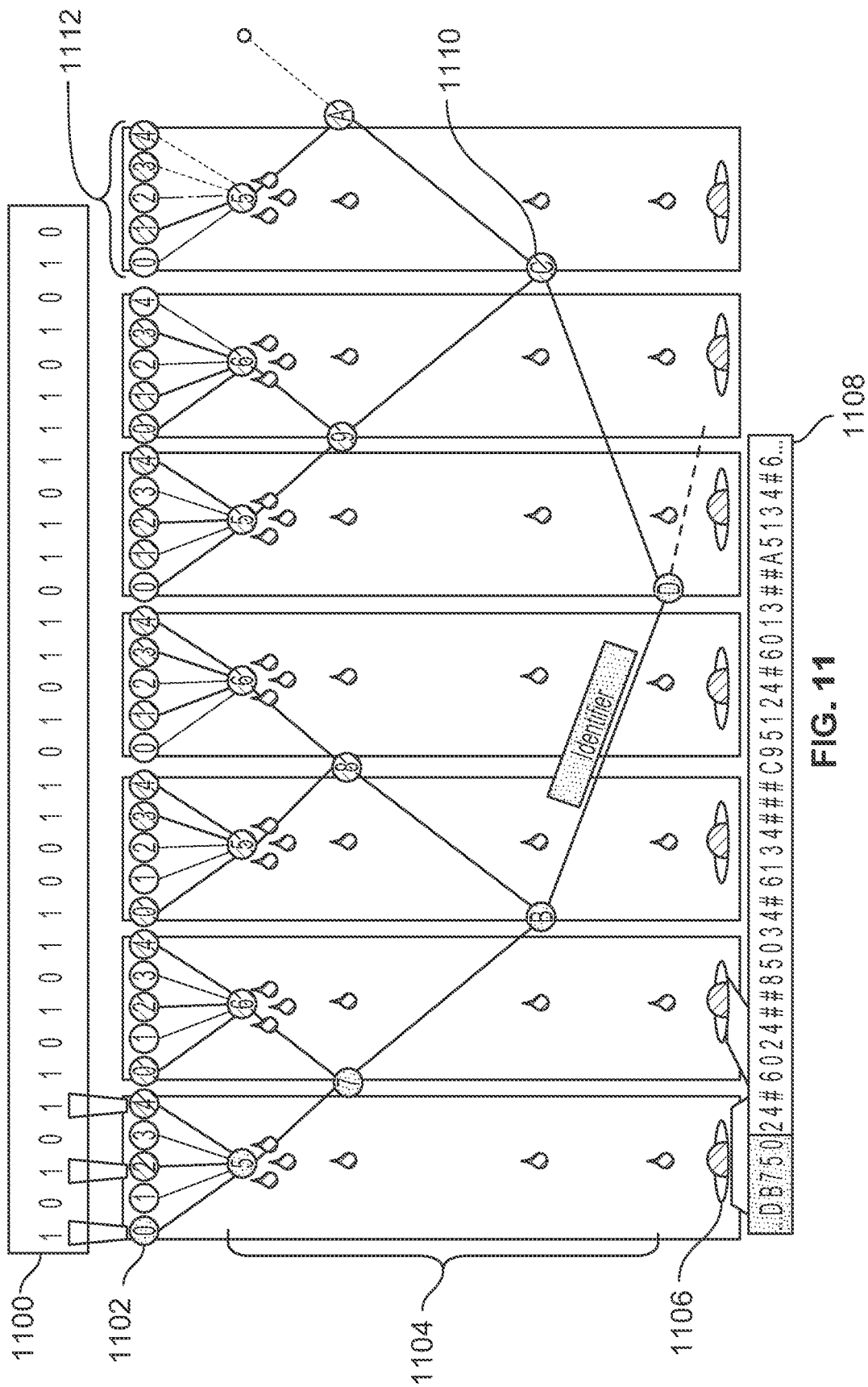
FIG. 11 shows a diagram of dispensing solutions into compartments according to a trie of identifiers.

FIG. 11 shows a diagram of encoding a string in an identifier library by dispensing solutions into reaction compartments according to identifier sequences constructed from a trie data structure, according to an illustrative implementation. A trie is an ordered tree data structure, in which each layer/level of the trie represents a layer of the identifier, and each edge of each trie layer represents a component within corresponding identifier layer. The final layer of the trie may represent the multiplex layer of an identifier. String of symbols 1100 represents a set of codewords to be stored in DNA identifier nucleic acid molecules. A codeword is a string of symbols that represents a specific string of symbols from a source alphabet, called a source word. A code maps source words to codewords in a process known as encoding. Droplets 1104 are dispensed into individual reaction compartments (e.g., compartment 1106). String of symbols 1100 is encoded by constructing identifiers that are represented by the trie paths connecting the root of the tree (not shown) to the leaves of the final (multiplex) layer 1102 that point to symbol values of '1'.

In general, the weight of a codeword includes the number of bits that have '1' values, relative to the number of bits in the codeword. As shown in FIG. 11 and as will be described further below, particularly in relation to FIG. 15, the codeword's "weight" is evenly distributed across the codewords because the string of symbols 1100 is divided such that each string of five bits (e.g., a sub-string) is encoded in a reaction compartment, and has exactly three '1' values (out of five) so each compartment receives three components from the multiplex layer to form three identifiers. For example, reaction compartment 1106 is configured to contain identifiers with a unique combination of components from the base layers (e.g., the components that comprise the path of the trie up to the multiplex layer—components 7, B, D, . . . ), and components 0, 2, and 4 from the multiplex layer, respectively, as shown in the multiplex layer and as corresponding to the positions of the string of symbols "10101". For each of the '1' values, the corresponding identifier molecule for that symbol position (including the components that make up the path leading to that symbol position) is deposited into the reaction compartment.

The output from the writing process of a string of symbols, as described above, is a library of encoded DNA (identifiers) that may require long-term storage and infrequent access. The produced pool of encoded DNA contains a large number (e.g., hundreds of thousands) of molecules of each identifier sequence. In terms of grams, the total amount of material produced may be in microgram quantities. The pool may be amplified with PCR to ensure enough material exists for redundancy, archiving, and accessing. After amplification, the pool may be allocated into multiple containers and stored in different locations. The pool may be stored in a range of nucleic acid storage and archival systems. For example, DNA may be stored in Eppendorf tubes, in a freezer, cryo-preserved in liquid nitrogen, or stored in Tris-EDTA. Shelf-life of DNA assessed by reading material subjected to accelerated stability conditions such as different temperatures. The systems and methods described herein may include an automated sample management system that allows for both long-term storage and random access of stored DNA.

In some implementations, an operating system (OS) is capable of coordinating writing, reading, discoverable querying of archives scalable to exabyte sizes, or any combination thereof. The OS may be configured to represent the storage medium as a collection of fixed size "blocks." Each block is a contiguous sequence of identifier sequences in a single identifier library, stored in a single pool of identifiers. A block may, however, be mirrored in several pools for fault tolerance. The OS can be responsible for organizing, allocating, and writing blocks. A "block index" is a hierarchical data structure mapping "block ID's" to physical addresses (comprised of container and identifiers), where a "block ID" is a logical address, barcode, or tag assigned to each block. The physical address contains the information needed to access its corresponding block. Specifically, in some implementations, the OS enables the reading and writing of a tree of semantically annotated and indexed blocks via a codec optimized for the read/write platform described above. The OS includes a translation stack that can include an ingest API, as well as modules for organizing and formatting data for long-term yet granular data querying and discovery. These aspects of the OS can be broadly suited for any writing, reading, or access method. Other aspects of the OS can be designed to specifically optimize methods for writing, accessing, and reading information. These include modules for compressing and error-protecting data, as well as modules for configuring and sending data to the writing systems described above. Though data written in DNA molecules with the above methods will be readable with any sequencer, specific reading methods are described below. The OS may also include automation software and workflows that mediate the handling of DNA-based information between the writer and reader; for example, by allocating DNA to, accessing DNA from, and replenishing DNA in a system of storage containers capable of supporting an Exabyte of information.

In some implementations, every block has a fixed, uniform size. For a plurality of blocks, each block having an associated block ID, the block ID's may be ordered, for example, by having ordered values or representations. The ordering of block ID's may be configured to implicitly indicate the physical address of each block having an ordered block ID. The physical addresses may be ordered, so that each block is located at an ordered physical address corresponding to its ordered block ID. For example, a first block ID may have a value or representation "0", and a second block ID may have a value or representation "1". The first block ID indicates that a corresponding first block is in a first address space, and the second block ID indicates that a corresponding second block is in a second address space.

For example, on can choose to partition a combinatorial space of identifiers into adjacent blocks of fixed size c codewords. In this way, the range of identifiers encoding the $g^{th}$ instance of a block, can be inferred as the range encoding codeword instances $(g-1)*c+1$ through $g*c$. These particular identifiers can then be readily accessed though chemical access programs which retrieve only identifiers that share specified sets of components in common. These access programs work by selectively targeting and subsequently enriching, or selecting, identifiers with said specified sets of components with probes, for example with primers and PCR or affinity tagged oligonucleotides and affinity pull-down assays. Probes can be applied in a series of selection reactions, wherein each reaction targets an individual component. The output from one reaction can be used as input into another reaction. identifiers can be logically ordered by their components and further because a blocks can be represented by a continuous range of these ordered identifiers, the identifiers that comprise a block are more likely to share components in common than if they were disparate. This reduces the complexity of the access programs needed to retrieve these identifiers. The reduced complexity can be further improved if the blocks are assigned to ranges of identifiers that exclusively share a set of components in common.

In some implementations, a primary string of symbols is stored over a plurality of blocks by dividing the primary string into a plurality of sub-strings. The string of symbols stored in each block is one sub-string of symbols obtained from the primary string of symbols. The sub-strings make up the primary string in an ordered manner. Accordingly, the block storing each sub-string may have a block ID that is ordered according to the position or order of the corresponding sub-string in the primary string. For example, the primary string may be divided into 5 sub-strings and stored over 5 blocks, each block having a block ID of a value from 1 to 5 (i.e., a first sub-string of the 5 sub-strings is stored in a block having block ID "1").

Figure 12:
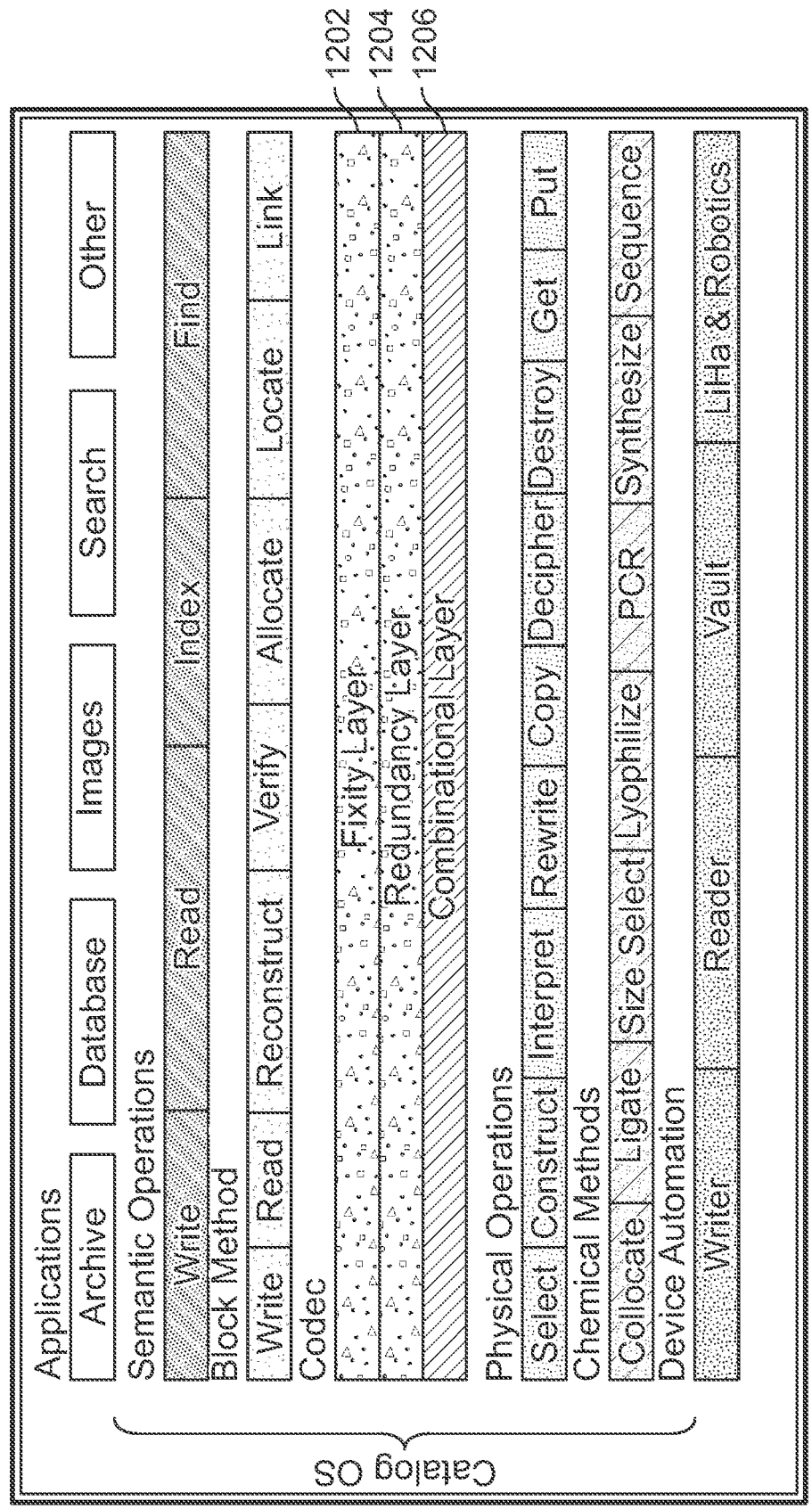
FIG. 12 shows a system diagram of an operating system organized by layer.

FIG. 12 shows a layered organization of the capabilities managed by the OS organized into functional layers, some of which involve data blocks and/or data structures, according to an illustrative implementation. Each layer draws on the services offered by the layer, summarized in the list below. The seven layers translate into six areas of development involving design and construction of:

(1) Codec: an encoder/decoder pipeline with writer-specific optimizations
(2) Chemistry Interface: a translator from bit operations to chemical operations
(3) Automation Interface: interfaces and translators to automation devices
(4) Block Abstraction: a block-based interface & supporting core data structures
(5) Search & Indexing: infrastructure for semantic annotation and indexing
(6) Archival Application: an archival application demonstrating the OS Benefits of the encoding schemes and OS described herein include the ability to select an encoding scheme optimized for writing speed, writing cost, reading cost, or access cost; the ability to optimize the mapping of index data to blocks to minimize decoded footprint; the ability to manipulate information at all scales from large blocks to single bits and model data structures natively; and tight integration with current archival standards and practices enabling archival, querying, and reasoning over data and relationships.

The codec functions as the encoder/decoder for information. Because layers above need it and layers below cannot be meaningfully tested without it, the proper operation of the codec is highly important. The codec receives a source bit stream and is charged with translating it into a form suitable for writing using chemical methods. The source bit stream is divided into packets, where all packets are of a fixed size. Packets may be processed independently and serve as a unit for parallel processing. Packets are composed of one or more blocks. A block is the smallest unit of allocation in the archive, and the archive's combinatorial space is divided into a series of contiguous strings of bits called blocks. The fixity layer is responsible for computing a block hash using a standard cryptographic hashing algorithm, and this hash is included in a parent block. When a block is decoded, its integrity may be checked by re-computing its hash and checking it via the parent block.

Figure 13:
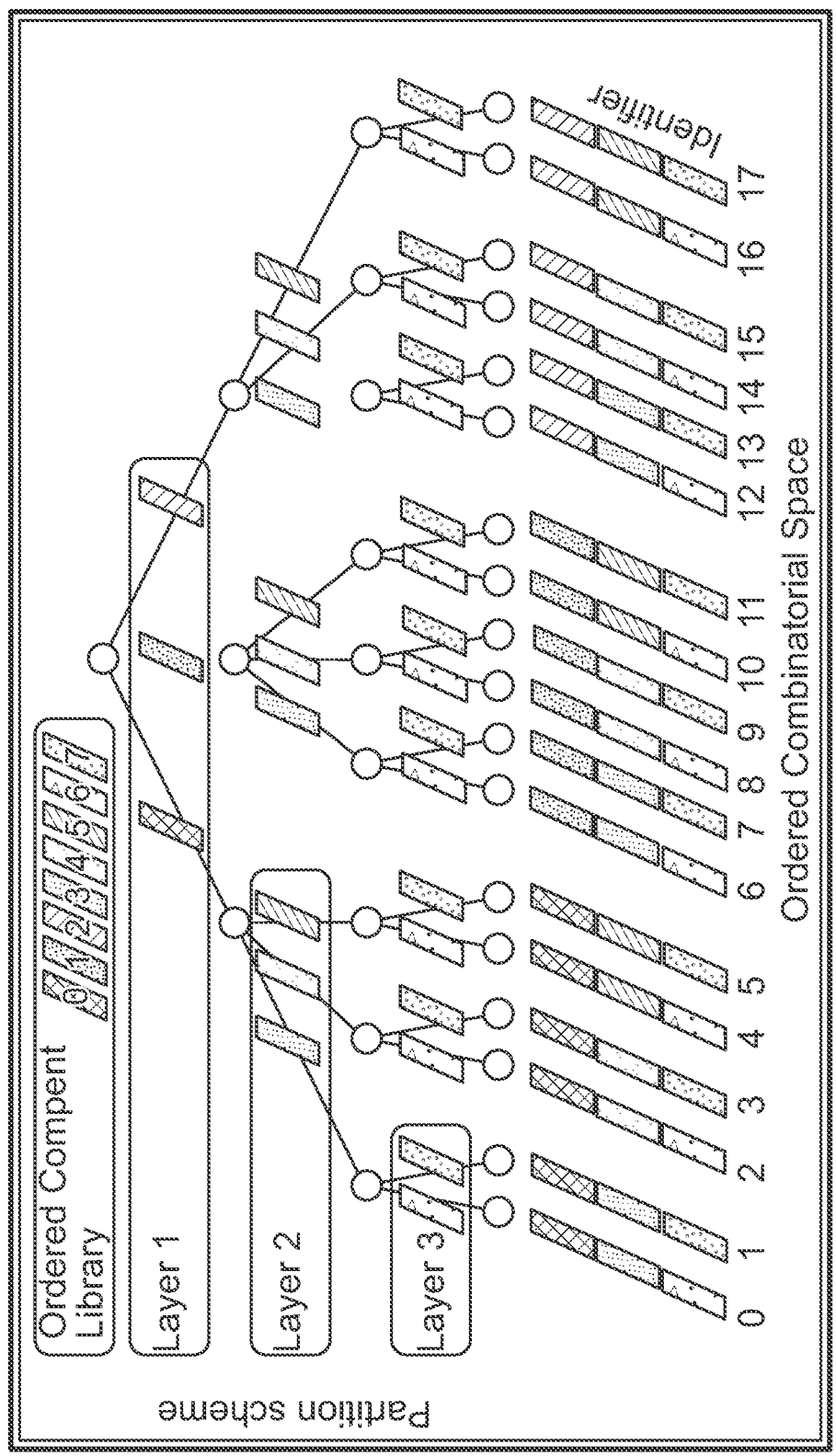
FIG. 13 shows system diagram of a layered product constructor with three layers and a component library of eight components.

In some implementations, the codec performs or orchestrates encoding in accordance with a data structure, such as a B-tree structure or a trie structure, including the example encoding scheme shown in FIG. 13.

FIG. 13 is a system diagram of a Layered Cartesian Product combinatorial constructor (LCPCC) for designing and ordering identifiers, according to an illustrative implementation. The product constructor has three layers (M=3) and a component library of eight component sequences (C=8). A combinatorial partition scheme with {3,3,2} component sequences per layer is shown, meaning three components in the first layer, three components in the second layer, and two components in the third layer. The space of all possible identifier sequences forms a combinatorial space. The total number of combinatorial objects constructible from the component library, which may be referred to as the span of a combinatorial scheme, determines the length of the bit stream writable to a single pool of identifiers. The span of this particular scheme is 3×3×2, or 18. In general, any combinatorial partition scheme may be used with C components separated into M layers, where the i-th layer has $C_i$ components, the sum across the M values of $C_i$ is C, and the product of the M values of $C_i$ is the span of the combinatorial space that defines the number of possible identifier sequences, and accordingly, the length of the writable bit stream. The combinatorial objects are ordered in the combinatorial space lexicographically by extending a ranking on the component sequences to the identifiers constructed from them. This ordering information is implicit in the identifier, identifies its position in the combinatorial space, and may be used to identify the position of the symbol encoded by the identifier in the source symbol stream. For example, the LCPCC may be used to encode a binary alphabet, and define the symbol encoded by a constructed identifier to be "1." The "0" symbol may be represented by not constructing the corresponding identifier. A source bit stream may be encoded by constructing a specific set of identifiers (i.e., an identifier library) unique to that bit stream.

Figure 14:
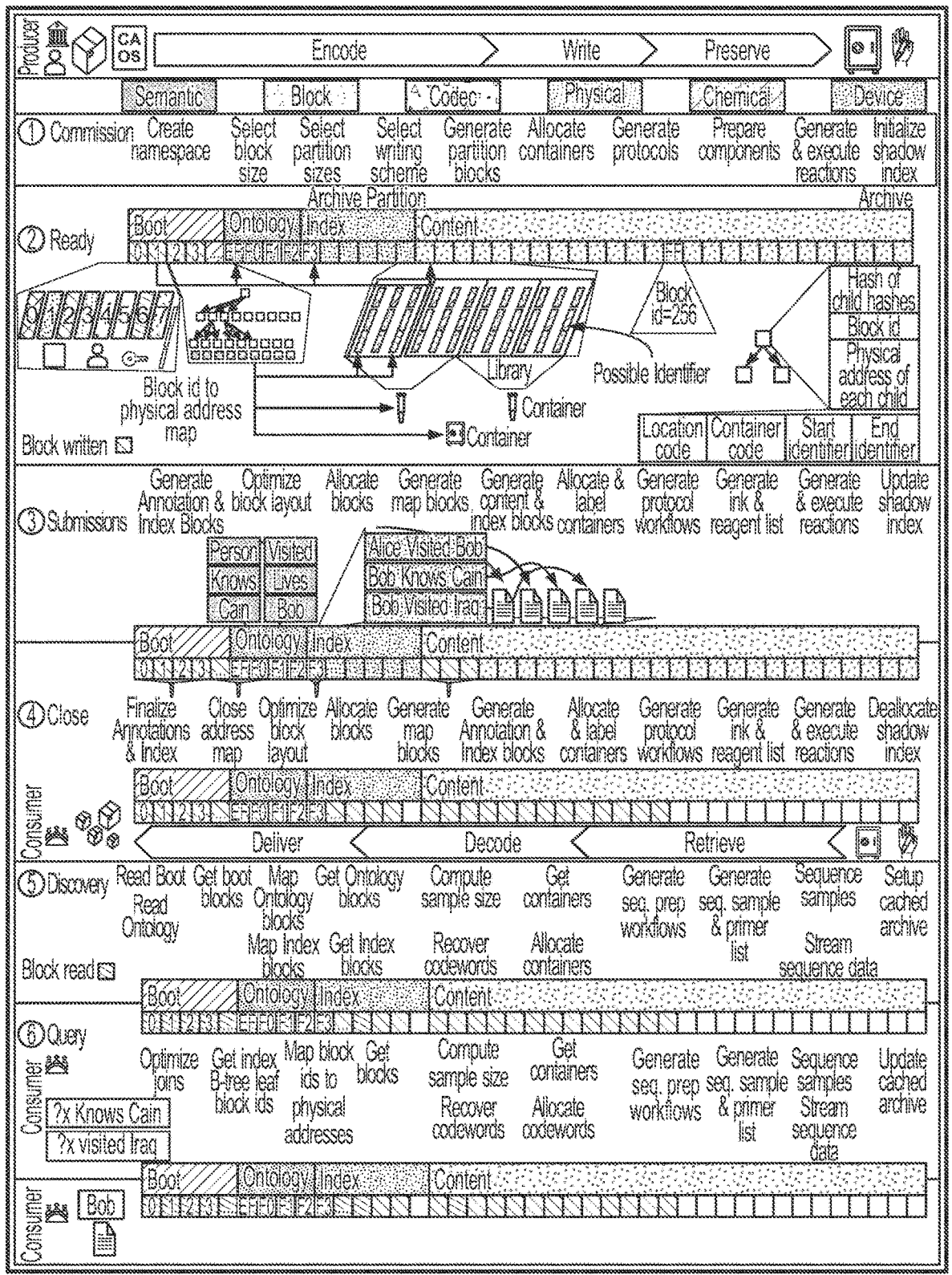
FIG. 14 shows a system diagram of archival operations.

FIG. 14 shows a system diagram of archival operations for mapping data blocks and using data structures, according to an illustrative implementation. The archive (CAR) is partitioned into boot, ontology, index, and content regions. The boot partition may be written using a standard encoding scheme capable of being decoded without any external metadata, and may store the parameters, keys, and addresses needed to read the other partitions. The OS abstracts the storage medium as a collection of fixed size blocks, as described above.

Each block may include a contiguous sequence of identifier sequences in a single identifier library, stored as a single pool of identifiers, and may be mirrored in several pools of identifiers for fault tolerance. In general, the OS is responsible for organizing, allocating, and writing blocks. When the block layer receives a source bit stream packet, the block index divides and allocates the packet to blocks in the archive. The boot partition comprises the block index, a hierarchical data structure mapping block IDs to physical addresses (comprised of container and identifiers). The block index tracks free/used blocks and allocate blocks to new packets.

Each block ID can be a logical address and can be converted to a physical address in the molecular archive. This is achieved by traversing the Block Index as illustrated in FIG. 14. Each node in the data structure (e.g., an address node) may include a sequence of child block identifier ranges, similar to a B-Tree data structure (e.g., as described below in relation to FIG. 15). Each range points to the next block on the path to the block of interest. In this way, the system maintains a tree of address nodes, which culminate in leaf nodes that refer to blocks in the molecular archive containing the actual data. In other words, the leaf node stores the block ID that identifies the physical address of the block, and can additionally stores a hash of the block. Internal nodes can also contain a hash, such as the concatenation of the hashes of its child nodes, thus forming a hash tree. As indicated in FIG. 14, the physical address of a block can include a Location Code, a Container Code, and an identifier range defined by a start and end identifier that refer to a plurality of identifiers that encode the relevant information. In general, it is possible for a block ID to resolve to more than one physical address to enable fault tolerance. In this case, the information stored in the block ID may be spread across two or more disparate containers, or two or more disparate identifier ranges.

Each high level operation on a block of bits depends on and results in a number of physical operations, which rely on chemical methods or physical steps. In order to orchestrate those chemical or physical processes, two types of software tools could be used. First, optimization tools translate block operations into an optimized set of physical operations. Then, translation tools convert the physical operations into detailed programs of actions to be executed by technicians or automation devices, and may include designing and implementing a translator between operations on blocks of bits and physical and chemical operations.

The systems and methods described herein provide preservation and targeted discovery and querying of an archive. Importantly, the present disclosure leverages data blocks and data structures to perform specific targeted access operations that do not require decoding of large portions of the archive. Instead, with the system sand methods of the present disclosure, it is possible to discover, query, and read targeted content selectively and incrementally, while minimizing the need to compute join operations and other structures on the archive. A key metric to be minimized is the total number of bits decoded to satisfy a sequence of queries.

Figure 15:
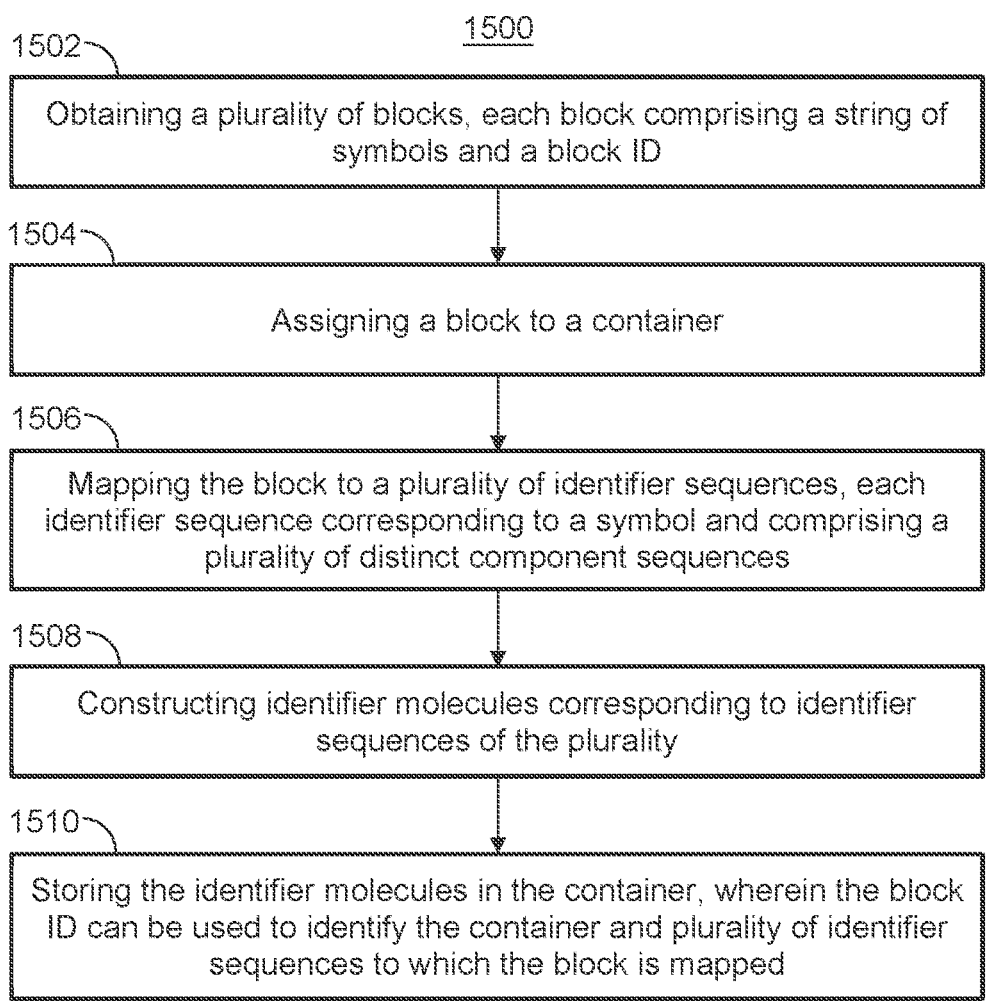
FIG. 15 shows a flowchart for storing blocks of data in containers.

FIG. 15 shows a flowchart 1500 outlining the steps for storing blocks of data associated with block identifications (IDs) in containers, according to an illustrative implementation. At step 1502, a plurality of blocks is obtained. Each block comprises a string of symbols and is associated with a block ID. A block ID may be any identifying characteristic or symbol associated with a particular block. For example, it may be a semantic annotation in the form of a triple. In some implementations, a block ID is an integer, a string, a position, a triple, a list of attributes, or a semantic annotation. For example, the first X symbols of a string of symbols included in the block may indicate a numerical ID for that block.

At step 1504, a block (one of the blocks belonging to the plurality of blocks received in step 1502) is assigned to a container. A container may be a physical location, such as a bin, tube, or other physical storage medium where nucleic acid molecules may be stored. A container may be linked to a single block or multiple blocks. For example, one container may be associated with B blocks of information. In some implementations, a container may comprise multiple sub-containers.

At step 1506, the block is mapped to identifier sequences to be associated with the container. These identifiers comprise an identifier range or multiple disparate identifiers of identifier ranges. An identifier range is specified by the component sequences that comprise the identifiers flanking the range. In some implementations, each individual identifier is associated with a distinct integer, such that an identifier range may be specified by two integers. An individual identifier sequence of the plurality of identifier sequences corresponds to an individual symbol in the string of symbols stored in the block. Each identifier sequence includes a corresponding plurality of component sequences. Each of these component sequences includes a distinct nucleic acid sequence.

At step 1508, individual identifiers of the plurality of identifier sequences are constructed. For example, a set of Q identifier sequences is associated with a particular container. A subset V of those Q identifier sequences may be physically constructed to represent information in the block, as described in various methods described above. At step 1510, the identifiers constructed in step 1508 are stored in the assigned container. For example, the assigned container then holds a number V of identifiers representing the information stored in the block. Identities of the container and the plurality of identifier nucleic acid sequences associated therewith are configured to be determined using the associated block ID. In some implementations, the identities are stored in a data structure designed to facilitate access of the identity of each container using the associated block ID. For example, the data structure is one of a B-tree, a trie, or an array. In some implementations, at least a portion of the data structure is stored along with the digital information in an index. The index includes a second plurality of identifier sequences associated with a second container. In some implementations, the index is stored in a magnetic storage device, an optical storage device, a flash memory device, or cloud storage In some implementations, the index includes a B-tree data structure. In this case, each node of the B-tree may include a distinct plurality of identifiers (i.e., different than the set of identifiers constructed in step 1508) of the second plurality of identifier sequences. The process involves searching the B-tree to determine the identities of the distinct plurality of identifiers. Specifically, searching for a particular block ID in the B-tree involves selecting the distinct plurality of identifiers that comprise a first node and reading a value of the first node. The steps of selecting an identifier and reading a value of a node may be repeated with subsequent nodes. The identity of the distinct plurality of identifiers that comprise the subsequent node is determined by the block ID in relation to the value of the first node. In an example, the first node is the root node of the B-tree and the process of selecting and reading nodes continues until the value of a leaf node of the B-tree is read. The value of the leaf node is configured to communicate whether the block for the block ID exists. If the block ID exists, the identity of the container and the identity of the plurality of identifier nucleic acid sequences comprising said block (for example, the identifier range) may be communicated to a user or system.

In some implementations, the index is a trie data structure. In this case, each node of the trie may comprise a distinct plurality of identifiers of the second plurality of identifier sequences. In some implementations, the block ID is a string of symbols and each node in the trie corresponds to a possible prefix of the string of symbols. If a path through the trie for a particular block ID exists, then the physical address (comprised of the container and identifier range or ranges) of the corresponding block can be specified by the leaf node of that path. Each intermediate node of the trie can be represented by a separate plurality of identifiers and can contain information regarding how many daughter nodes it has, what symbols those daughter nodes represent, and the physical addresses (comprised of the container identity and identifier range or identifier ranges) of those daughter nodes. In that way, the trie can be navigated in DNA, similar to the B-tree, using access and read operations as described herein. Method 1500 may further comprise accessing a physical address, using a series of probes, from a pool of identifiers comprising the second plurality of identifier sequences.

In some implementations, the data structure is an array. In this case, each element of the array comprises a distinct plurality of identifiers of the second plurality of identifier sequences. Each element in the array may correspond to a block ID and contain the physical address (including the container identity and identifier range) of that block ID.

The physical address may be natively configured to the block ID such that the block ID maps to the physical address without storing the physical address in an additional data structure. For example, the block ID maps to a plurality of component sequences that are shared by all identifier sequences of the plurality of identifier sequences associated with the physical address. A plurality of identifier sequences associated with a block may comprise contiguously ordered identifier nucleic acid sequences (e.g., as is described in relation to FIG. 13), such that said plurality of identifier sequences is specified in a corresponding physical address by an identifier range comprising the identities of the first and last identifiers of the range. The first and last identifiers may be represented by integers. A plurality of identifiers (e.g., those associated with a block) can be accessed using a series of probes, which may be sequential. Probes can be PCR primers, such that accessing is executed via PCR, or probes can be affinity tagged oligonucleotides, such that accessing is executed via an affinity pull down assay.

In implementations where the block ID is a position, said position may be a position in a string of symbols that is represented by the corresponding block of a parent string of symbols. Said parent string comprises a data structure, for example, for counting or locating the occurrences of a pattern in another string of symbols. As discussed below, said data structure may be a Burrows-Wheeler Transform (BWT), a suffix array, a suffix tree, or an inverted index.

Data structures may be stored in the blocks to help determine, locate, and count pattern occurrences in the data using a suffix tree based approach. In a suffix tree, the blocks are configured to represent nodes of a suffix tree. The suffix tree is a trie, where every path from the root node to a leaf represents a suffix of a symbol string S. The edges of the trie represent substrings of symbols that comprise each path. A suffix tree can be represented in an identifier nucleic acid library where every block corresponds to a node in a suffix tree and contains information about its daughter nodes. For example, information about daughter nodes comprises the substrings of symbols that comprise the edges leading to each daughter node, and the physical addresses of the blocks containing those daughter nodes. The root node can be a prescribed block, like the first block. Querying for the membership, count, or location of a pattern involves following a path along the suffix tree by accessing identifiers of the block corresponding to root node, decoding the information contained therein, determining the physical address of the next block based on the information contained therein and the query pattern, and continuing the process until either no downstream blocks (or nodes) are left that will satisfy the corresponding query or until a lead node is reached. In the former case, the query pattern does not exist in the string S. In the latter case, the blocks corresponding to the leaf node can be configured to contain the count or locations of the query pattern.

Data structures may be stored in the blocks to help determine, locate, and count pattern occurrences in the data using an inverted index based approach. In an inverted index, there can be a block for each possible substring of a fixed length over a symbol alphabet that comprises a string S of symbols. Each block can contain information about the starting positions of the corresponding substring within S. The block IDs can correspond to the substrings, or they can correspond to the positions of the sorted substrings, such that the physical address of a block corresponding to a substring can be ascertained without additional information. A query pattern can be mapped to substrings of the inverted index the comprise it, and the blocks can be accessed and decoded. The positional information contained therein can be used to determine the count and locations of the query pattern within S. The inverted index need not be limited to substrings of fixed length. For example, it can also be used to represent the positions of words in a document, or across multiple documents.

Data structures may be stored in the blocks to help determine, locate, and count pattern occurrences in the data using a full-text index in minute space (FM-index) based approach. An FM-index is a sub-string index based on a Burrows-Wheeler Transform (BWT), with similarities to a suffix array. The FM-index is a data structure which allows for compression of input data or text while permitting fast sub-string queries. Construction of the FM-index is described in detail below. The FM-index may be used to efficiently find the number of occurrences of a pattern within the compressed data/text as well as to locate the position of each occurrence. Accordingly, in some implementations, the string of symbols stored in a block is a portion of a data structure intended to support locating, counting, and/or determining the membership of any sub-string of symbols within a second string of symbols, which may be larger than the first string. The data structure may be an FM-index, a counter array, a Burrows-Wheeler transform, or a suffix array—each of these data structures are discussed in further detail below, with reference to FIGS. 16-19. In some implementations, the data structure is stored in a distinct set of one or more containers, for example, separate from containers where the second string is stored.

As mentioned above, a data structure may include a BWT, which converts a string S to into a transform of the string: bw(S). The transform has certain properties that assist in searching string S (see description below in relation to FIGS. 26-32). In general, the BWT may be considered as a permutation or lossless transformation of the input symbols/bits which are ordered in the transform in a manner that is suitable for compression via methods that are easier to implement relative to an un-transformed string S. The BWT includes a pair of transformations: a forward transform, which rearranges the symbols of the input string S to form bw(S); and a backward transform, which reconstructs the original string S from its BWT bw(S).

In general, for an input string $S=s_1, s_2, \ldots, s_n$ having length n, where the symbols of S are selected from an ordered alphabet $\Sigma$ (e.g., the English alphabet, a set of positive integers, any set of characters or symbols, or a combination thereof). The forward transform proceeds on this input string S as follows. A string s$ is built, where $ is a special symbol which does not occur in the ordered alphabet $\Sigma$ and is assumed to be smaller than any other symbol in the alphabet according to its total ordering. For example, with the English alphabet, the total order would be $, A, B, C, . . . X, Y, Z. Conceptually, a matrix M of size (n+1)×(n+1) contains rows that are all the cyclic left-shifts of string s$. Matrix M may be referred to as the rotation matrix of s. A left-shift of a string entails moving the first symbol of the string to the end of the string, and shifting all other symbols by one position to the left. This left-shift is iterated until every possible cyclic left-shift of s$ is included in M (see left hand side of FIG. 16). The matrix M, need not be explicitly constructed during a Burrows-Wheeler transformation. Then, the rows of M are sorted lexicographically, reading the rows left-to-right and according to the order defined on alphabet $\Sigma$, with $ being considered as first in the order. The final sorted matrix M includes a first row that is $s, because $ is smaller than any symbol in Z and only appears once in the string (see right hand side of FIG. 16). The last column of the matrix M' corresponds to a column L that includes $, while the Burrows-Wheeler transform bw(s) is equal to (L', r), where L' is the string obtained by reading the last column of M and omitting the symbol $, and r is the position of the symbol $ in the last column.

Figure 16:
FIG. 16 shows a Burrows-Wheeler transform of a string.

FIG. 16 depicts an illustrative example of the BWT for a string S="abracadabra", according to an illustrative implementation. The unsorted 12×12 matrix, M, is shown on the left, having each cyclical left-shift of S$, yielding 12 rows for the 11 symbols in S plus the added symbol $. The right hand side of FIG. 16 depicts the sorted version of the 12×12 matrix M', which has a first row corresponding to the string starting with $, "$abracadabra", because $ is defined as first in the order of all the symbols of S$, and the rest of the strings are sorted according to the order of the English alphabet. The five rows starting with symbol a (because the letter a appears five times in the words "abracadabra") are sorted in alphabetical order according to the following symbols (e.g., the second, third, fourth, and fifth symbols). This process of transforming the matrix M to derive M' may be referred to as suffix sorting or right sorting.

Reading the first column of the sorted matrix, M, denoted by F, gives the string "$aaaaabbcdr" which is the sorted sequence of all symbols in S. The same string but without the first character $ is represented as F', or "aaaaabbcdr". The output string, L', is obtained by reading the last column, L ("ard$rcaaaabb"), and excluding the symbol $, so L' is equal to "ardrcaaaabb". The position of the single occurrence of the symbol $ in the last column is noted as r equal to 3. The output string L' has a locally homogeneous property that is particularly useful in compression settings. Specifically, the locally homogeneous property is apparent in that the last six symbols of the last column L in FIG. 16 form a highly repetitive string "aaaabb" that can be highly compressed via compression methods. This property of local homogeneity is intrinsic to the BWT, because the strings are sorted by the alphabetical order according to their right context (i.e., suffix).

A suffix array (SA) may be used herein. A suffix array, sa[0, n−1], constructed for a string s of length n symbols, stores in sa[i] the position of the $i^{th}$ suffix of s in lexicographic order. The suffix position sa[i] may be encoded in a number of bits equal to $\log_2(n)$, and the suffix array sa may be serialized in binary. This serialization involves concatenating each bit representation of the suffix positions in the suffix array or storing each bit representation in identifiers in distinct containers.

FIG. 17 depicts an example suffix array for the string S="abracadabra", compared to the BWT of the same string, according to an illustrative implementation. The first column in FIG. 17 shows every suffix of string S$, which is the input string S with the symbol $ appended, where the symbol $ is defined as the first in the total order of symbols. Each suffix is obtained by, for each position in the string S$, taking the symbol at that position and all following symbols. The corresponding suffix positions, the starting position of each suffix in S$, are in the second column of FIG. 17. For example, the first suffix in the top row has suffix position 0, and is therefore the entire string S$, or "abracadabra$." The second suffix in the top row has suffix position 1, and is therefore the portion of the string S$ beginning after the first position, or "bracadabra$." The remaining suffixes are similarly determined.

Just like the BWT involves sorting the rows lexicographically, the suffixes from the first column of FIG. 17 are sorted lexicographically according to alphabetical order, and are listed in the third column of FIG. 17 and their corresponding suffix positions listed in the fourth column of FIG. 17. Here, the suffix "$" will always be in the first row of the sorted suffix array, because the symbol $ is defined as first in the lexicographic order. The listed of sorted suffix positions, in column 4, may be the suffix array that is physically stored.

The last two columns of FIG. 17 shows the sorted-rotated matrix M' and corresponding last column L, for the same input string having been converted to a BWT, as depicted in FIG. 16. The sorted suffixes in the third column correspond to the rows of matrix M', and for each row of matrix M', the corresponding sorted suffix is the set of symbols up to and including the symbol $. Every symbol L[i] in the last column L for the i-th row corresponds to the symbol of the input string s that precedes the suffix position sa[i] in the same row of FIG. 17 (i.e., the $i^{th}$ row). However, if the suffix is the whole string (i.e., sa[i]=0), then $ is used as the preceding symbol. In this manner, sorting the suffixes for the SA may be equivalent to sorting the rows of M for the BWT. The relation between each structure is formalized by the following equation:

$$L[i] = \begin{cases} s[sa[i]-1] & \text{if } sa[i] \neq 0 \\ \$ & \text{otherwise} \end{cases} \quad \text{Eqn. 1}$$

This relation shows there is a bijective correspondence between the rows of the rotated matrix M' and the suffixes of the string s. Given the suffix array of string s, it takes linear time to derive the string L for the BWT.

Figure 18:
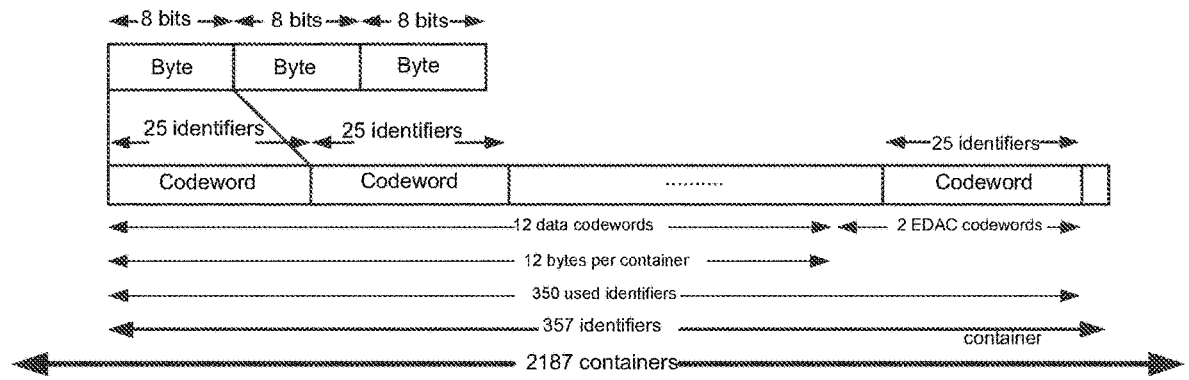
FIG. 18 shows a graphical example of a Burrows-Wheeler transform stored in nucleic acids.
Figure 19:
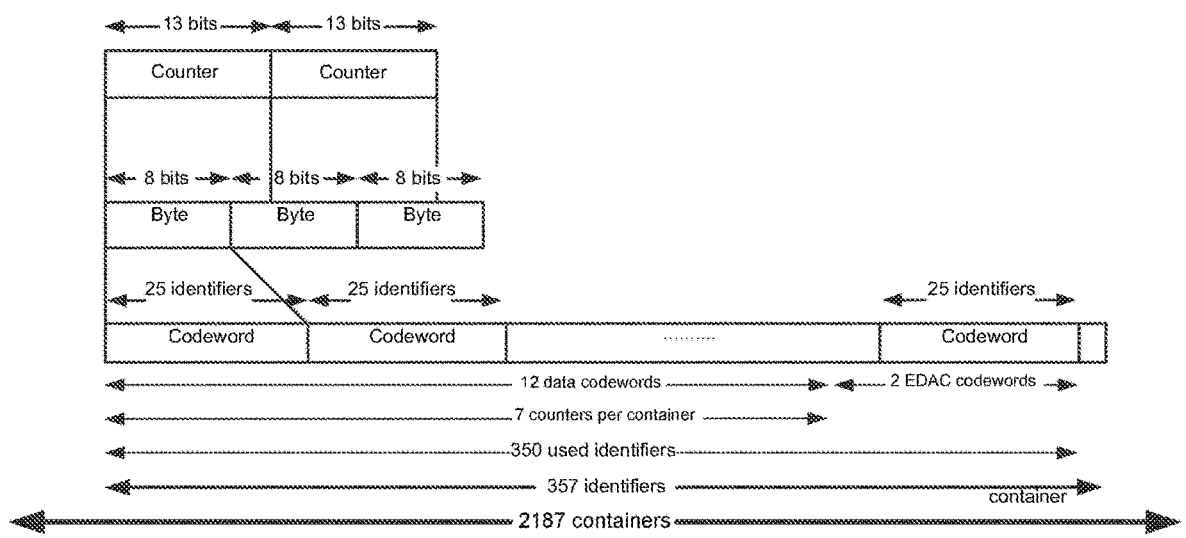
FIG. 19 shows a graphical example of a counter array stored in nucleic acids.

FIGS. 18 and 19 depict a lab example that implement the data structures described herein, according to an illustrative implementation. This lab example is implemented using a component library size of 378 components, which are subdivided among 8 levels as indicated by the following partition scheme: (3, 3, 3, 3, 3, 3, 3, 357). The fan-out for a trie, corresponding to this library, takes value c=3 for the first 7 levels and then value c=357 for the last level. A total of 780,759 unique identifiers may be encoded with this component library (i.e., $3^7 \times 357 = 780{,}759$). In some implementations, not all such identifiers are used to encode symbols of an indexed string s, for example, because technology constraints in the writing of such identifiers and in designing error-correction codes for making the approach feasible and robust. The example depicted in FIGS. 18 and 19 is shown for illustrative purposes only, and it will be understood that the present disclosure is applicable to component libraries of any size, for any number of levels. It is to be understood that, while the term "container" often refers to a physical compartment in this disclosure, the containers described in relation to FIGS. 18 and 19 refer to sets of nucleic acid molecules, that are not necessarily physically partitioned in distinct compartments.

FIG. 18 shows an example representation of encoding of a Burrows-Wheeler transform of a string, according to an illustrative implementation. In this example, a container refers to a group of identifiers which share the same 7 component-long prefix and distinguish themselves according to the last component of the 357 possible components partitioned in the last layer. Identifiers sharing the same 7 "base" levels are constructed in a single container in parallel, for example, by multiplexing identifiers in a single self-assembly reaction. There are $3^7 = 2{,}187$ containers, and each container may contain 357 unique identifiers according to the 357 components available in the last layer for identifier construction. When the 7 base levels are constructed in parallel, they may be replicated to an amount equal to the number of identifiers having distinct components the last layer.

A low-weight codebook may be implemented which uses only 350 identifiers per container, out of the 357 available identifiers. In general, a low-weight codebook may use any suitable number of identifiers per container, relative to the number of available identifiers per container, as long as the number of identifiers per container is less than a threshold. The codebook partitions the 350 identifiers in blocks of 25 identifiers, yielding 14 blocks per container. Each block may correspond to a codeword. Each container can be partitioned into 12 data codewords, which encode some bits of information, and 2 error detection and correction (EDAC) codewords, which implement an error-correcting code. If each codeword sets 2 identifiers out of the 25 available identifiers, the 300 possible codeword configurations (25 choose 2) will allow encoding 1 byte (8 bits), hence 96 source bits per container with error correction. For a set of 2,187 containers, 26,244 bytes of information can be encoded, with 4,374 bytes for error correction.

Given a binary string s of size n equal to $2^{13} = 8{,}192$ bits (1 kilobyte), the Burrows-Wheeler transform may be used for encoding of the string s. The length of the BWT of string s (i.e., BWT(s)) is the same as the length of string s, specifically $n=2^{13}$ in this example. A teaching-style algorithm may be used to build the BWT of s. According to the low-weight codebook, each container encodes 12 bytes or 96 bits of information (1 byte or 8 bits for each data codeword). The BWT of s, BWT(s), having length 8,192 bits, are serialized in 86 containers (ceiling of 8,192 bits divided by 96 bits per container). Blocks of size w=96 bits can be defined such that each container encodes a block of the BWT(s). Further a counter array can be encoded that stores the running count of a particular symbol value per block (96 bits) of BWT(s).

FIG. 19 shows an example representation of encoding a counter array derived from the Burrows-Wheeler transform of FIG. 18, according to an illustrative implementation. The counter array is divided into blocks, or counters, of a set length b 13 bits, enough to store a number of size $2^{13}$=8192 equal in length to the number of symbols in BWT(s). Accordingly a container can store floor(96/13)=7 counters with 12 codewords, and with an additional 2 edac codewords. In this example, each block of the counter array corresponds to a block in the BWT of s, $BWT_s$, and stores the number of 1's in the prefix of that position. This relation is formalized to define the counter array as c[0,floor((n−1)/w)] (counter array c having length floor((n−1)/w)+1) such that c[i] (a given block or counter, the $i^{th}$ block of c) stores the number of 1's in the prefix $BWT_s$[0, i×w−1]. Accordingly, c[0] (the first block of c) is equal to zero. A given counter c[i] is stored in container at position floor(i/7) and counts the number of 1's (bit value 1) that occur in the part of the $BWT_s$ before the $i^{th}$ container.

The $BWT_s$ has length n=$2^{13}$ bits, and each counter may be encoded in $\log_2(n)$ bits, equal to 13 bits. The counter array c is serialized in binary by allocating 7 counters per container, because 7 counters of 13 bits each is equal to 91 total bits which is less than the maximum storage per container of 96 bits. Accordingly, a given counter c[i], represented in 13 bits, is stored in container labeled floor(i/7), counting the containers from 0. 86 containers store the transform of s, $BWT_s$, so there are 86 total counters forming the array c. The 86 total counters are stored over 13 containers (ceiling of 86 counters divided by 7 counters per container). FIG. 19 graphically shows this exemplary distribution.

As described above for the counter array, a suffix position of a suffix array for the same string s may be encoded in 13 bits ($\log_2(n)$ bits). The suffix array is serialized in binary by storing 7 suffix positions per container. For the same example as above, a given suffix position sa[i] is located in container floor(i/7), counting containers from 0. The suffix array takes ceiling(n/7) containers, equal to ceiling(8,192/7) containers, or 1,171 containers.

The above described data structures are stored in a total of 1,270 containers (86 for the BWT plus 13 for the counter array plus 1,171 for the suffix array. This usage of containers is a fraction of the 2,187 available containers according to the component library used for this example. The overall target library may be subdivided according to the follow notations: the BWT library $L_{BWT}$, the counter library $L_C$, and the suffix library $L_{SA}$. In some implementations, this subdivision is only logical or implicit, such that accesses of these libraries can occur in parallel. For parallel accesses, queries to each library may be combined.

In the above example, obtaining $\text{rank}_1(x)$, that is the total number of occurrences of bit-value '1' up to and including bit position x, of $BWT_s$ involves the following. First, calculating the block of that bit position in $BWT_s$, which is the block position z=floor(x/w), where w=96 is the block size of $BWT_s$. Second, reading said block by accessing its container, which is at container position z of $L_{BWT}$, and decoding the data encoded therein to calculate a first count $n_{BWT}$ of the number of bit-values of '1' up to and including position x. Third, reading the corresponding counter z in the counter array, which is in the container position floor(z/7) of $L_C$ since there are 7 counters per container, and decoding the data therein to calculate a second count $n_C$ if the number of bit-values of '1' up to the block containing bit position x. And last, taking the sum of the first count and the second count ($\text{rank}_1(x)=n_{BWT}+n_C$. This method is extensible to calculating the rank with respect to 0, since $\text{rank}_0(x)=x-\text{rank}_1(x)+1$.

It should be understood that in this example, the $i^h$ block of the counter array counts a particular symbol value up to the $i^{th}$ block of the BWT, but that in other embodiments, the $i^{th}$ block of the counter array can count a particular symbol value up to and including the $i^{th}$ block of the BWT. Such a difference would only change the third step above where $n_C$ would correspond to the counter at position z−1 instead of position z. Alternatively, the steps could be configured to count the total number of bit-values of '1' through block z and then subtract the number of bit-values of '1' that occur after position x within block z. Generally, any mapping of BWT blocks to counter blocks f(z) can be defined without affecting the efficiency of the method. It should also be understood that identifiers belonging to containers, as used in this example, are configured to be efficiently accessible with a series of probes that each bind a component (since identifiers of each container share an exclusive set of 7 components in common). And moreover, that the information contained within a container is configured to be correctable to a certain tolerance due to the 2 associated edac codewords per container. In general, different mappings of the counter array and the $BWT_s$ to identifiers could have been defined.

Efficient Read and Access Operations of Data Stored in Nucleic Acid Sequences

Figure 20:
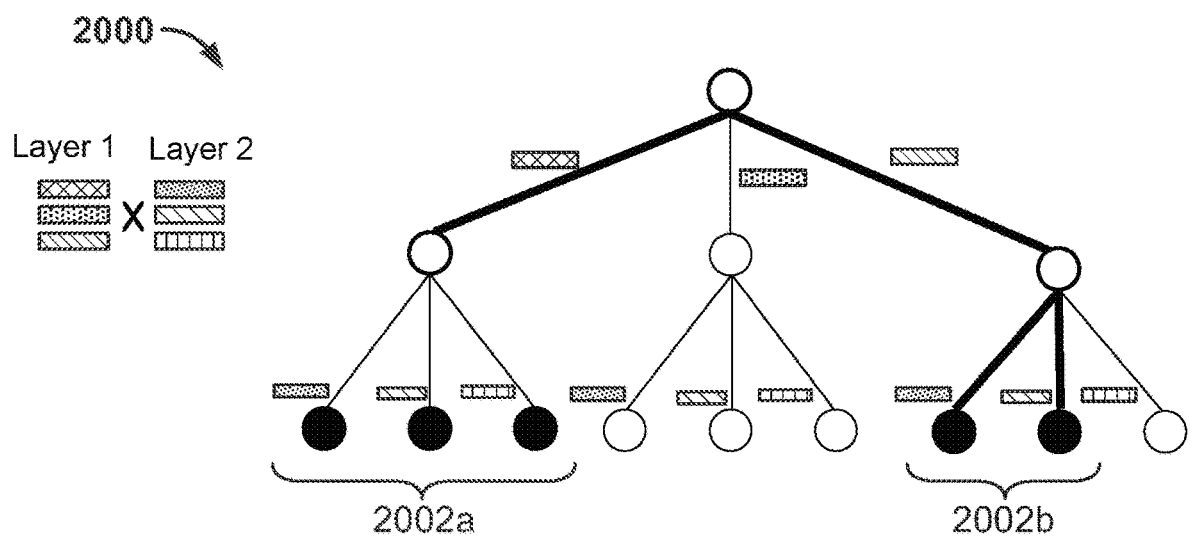
FIG. 20 shows a graphical example of a query tree.
Figure 21:
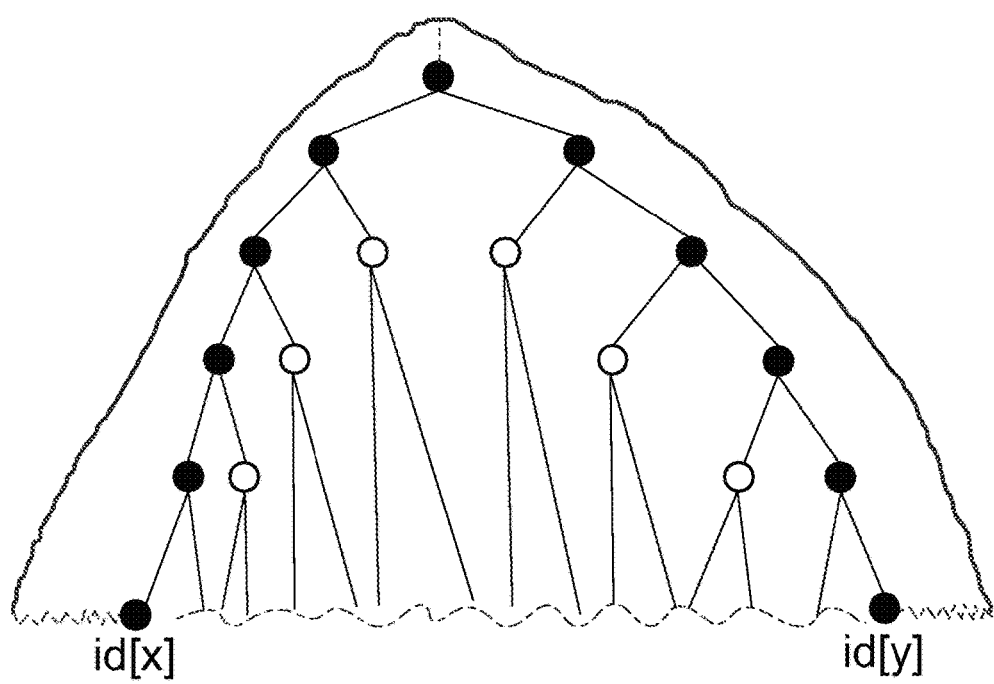
FIG. 21 shows a graphical example of a decomposition of a contiguous range of identifiers in a binary tree.
Figure 22:
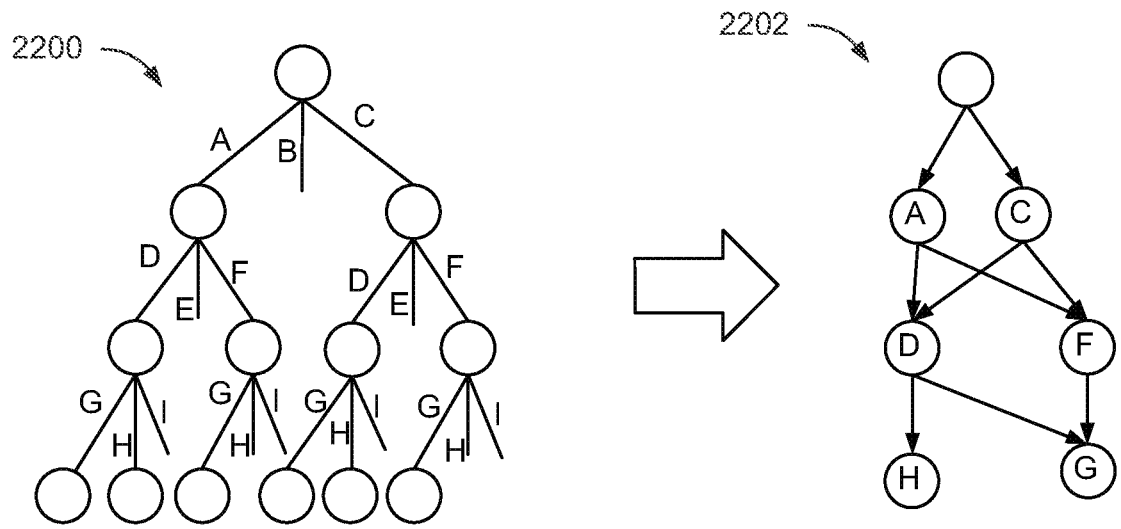
FIG. 22 shows a graphical example of conversion of a query tree into a query-directed acyclic graph.

Identifiers may be accessed and read to reveal encoded information; read and access operations are described in relation to FIGS. 20-22. Given a library L of identifiers, a read operation Read(L) can be performed to fully read the set of identifiers contained in L, and an access operation Access(L,Q) can be performed to select identifiers from L by specifying a proper query formulation Q. Reading a library L refers to a process of obtaining a random subset of identifiers from L, each identifier having multiplicity (or copy number). A DNA sequencer may be used to execute this process. A reading method with DNA sequencing is defined by two parameters: a maximum size of the subset of L that the sequencing operation can sample and report in a single run, referred to as a number of reads, which is independent of the size of L, and a maximum length of an identifier that can be read, referred to as a read length. A number of times a specific identifier is sampled by a reading process is called the copy count or the coverage of that identifier in that specific process run. It is to be understood that both terms "access" and "query" are used in the present disclosure to a process for targeting a subset of nucleic acid molecules, data, or information from a set of which. These terms may be used interchangeably herein.

Given a technology with a maximum random read throughput of $R_{max}$ identifiers, a function≤$f(R_{max}, \delta)$ can be defined such that L, having multiplicity in its identifiers, can be fully read with failing negligible probability≤$1/|L|^\delta$, if and only if $|L| \leq f(R_{max}, \delta)$. In other words, library L has duplicate identifier molecules having the same identifier sequences, so f indicates the number of distinct identifiers that can be read comfortably with a negligible probability of failure. As an example, a current technology supports a number of random reads $R_{max} \approx 25 \times 10^6$ and a read length of 150 nucleotides. A reasonable estimation of ≤$f(R_{max}, \delta)$ for this technology is $25 \times 10^4$ to guarantee a probability of failure smaller than $10^{-6}$ in sampling all distinct identifiers in L.

For smaller libraries, a non-random reading process is performed whereby the presence or absence of each possible identifier is determined with a hybridization assay, for example, a DNA micro-array, a CRISPR-based probe, or PCR. This non-random reading method may be faster and cheaper than DNA sequencing, for example, when reading libraries of size 1,000 or fewer identifiers.

As identifiers are constructed of components corresponding to different layers, it is possible to access identifiers that have specific components at some specific levels, or layers. A query formulation is built as a regular expression composed by logicals AND and OR, and by a match-component operator formalized in the form of a set of tree structures called query trees, which is orchestrated in the form of a directed acyclic graph (DAG), the access program. A DAG will specify the order in which chemical reactions will be executed over various containers containing the identifiers. For example, a query over the combinatorial space of identifiers in FIG. 13 may be specified as something like: all identifiers with components matching (0 or 2) and 5 and 6. Such an expression, when orchestrated as an access program would access identifiers 4 and 16 within a library defined by this combinatorial space. The access program could be three reactions, performed in series. A first reaction where probes are used to selected for identifiers with components 0 or 2 (for example with multiplex PCR). A second reaction that takes the output nucleic acids from the first reaction and uses a probe to select for identifiers with component 5. And lastly a third reaction that takes the output nucleic acids from the second reaction and uses a probe to select for identifiers with component 6.

In order to access a subset of L, a selector($i,c_i'$) allows for restriction of the set of identifiers in L to the identifiers having an $i^{th}$ component that is a member of the subset $c_i'$ of the full set of components $C_i$ in the $i^{th}$ layer. $c_i'$ implements the OR logical of a match for the particular $i^{th}$ component. Selectors s and t may be composed together to obtain a selector which restricts L to identifiers which match both s and t, thus obtaining an AND logical. The AND logical applies to consecutive levels, implementing a selection over one or more sub-paths in a trie T(L), such as the tries in FIG. 11 and FIG. 13, but having specificity to the library L. As discussed above, access involves PCR or affinity tagging, for example. As identifiers are constructed of components corresponding to different layers, it is possible to access identifiers that have specific components at some specific levels. A query formulation is built as a regular expression composed by logicals AND and OR, and by a match-component operator formalized in the form of a set of tree structures called query trees, which is orchestrated in the form of a directed acyclic graph (DAG), the access program. A DAG will specify the order in which chemical reactions will be executed over various containers containing the identifiers.

A set of m selectors is called a left-selector or a 5'-selector, when the levels of all the m selectors are distinct and refer to the first m levels of the trie T(L). A set of selectors σ is called an accessor when σ contains at least one left-selector accessing no more than π levels of T(L), where π is a parameter of a chemical method, such as PCR, being used for the access operation. For PCR, a value of π may be 2, because two components are targeted in a reaction by targeting one component with each of two PCR primers. Accessors are combined to form a query tree Q which is a sub-tree of T(L).

FIG. 20 shows a graphical example of a query tree 2000 performed over a trie T(L), according to an illustrative implementation. Trie T(L) enumerates a combinatorial space of 9 identifiers, indicated by the 9 bottom nodes of the trie. As depicted in FIG. 20, each identifier has two components: one component from layer 1 and one component from layer 2. The query Q is performed over T(L) to select five identifiers, three identifiers in group 2002a and two identifiers in group 2002b. Rather than parsing five paths to reach the five identifiers, the query Q involves a reduced set of paths. Specifically, the query Q involves a set of only three paths: one partial path, and two full paths.

A partial path is a downward path in T(L) starting from the root (the singular, top-most node in the trie) and leading to one of the internal nodes (one of the three nodes in the middle level of T(L) in FIG. 20). A partial path has length<M a number of layers used to define the identifiers of library L. The partial path in Q involves only two nodes, so one accessor of π=2 components is sufficient for specifying the partial path. As depicted in FIG. 20, the partial path selects three identifiers in group 2002a.

A full path is a downward root-to-leaf path in T(L), extending from the root to a leaf (one of the bottom nodes in the trie, indicating a unique identifier sequence). A full path has length=M. Each of the two full paths involves three nodes each, so two accessors, one of π=2 components and one of one component, is sufficient for specifying each full path. The two full paths in FIG. 20 share a root node and another node at the first level, so the two full paths may be decomposed into an accessor of size π=2 (to go from the root to the other node) and two distinct selectors for the two distinct leaves at the end of each full path.

In other words, when a query tree Q is executed to access a subset of identifiers in L, a full path selects just one leaf (the leaf reached by the full path), and a partial path selects multiple leaves (leaves that may be reached by full path extensions of the partial path). There is a bijection (one-to-one pairing) between the leaves of T(L) and the identifiers of L, so the execution of Q on L selects the identifiers represented by the leaves of T(L) reachable by the query tree Q. $L_Q$ denotes the subset of L selected by Q. In the example of FIG. 20, the query tree Q selects five identifiers of L, so $L_Q$ contains the five identifiers denoted by the groups 2002a and 2002b.

A query tree may not necessarily be implemented by just one chemical reaction, because Q may fetch more identifiers than physically allowed by the access method. For example, a given Q selects more identifiers than f($R_{max}$, δ), or Q has a depth greater than π=2, requiring execution of many accessors. These issues may be addressed by an access program that is a DAG in which nodes are part of query trees, and edges denote Input/Output between the connected nodes, hence, query trees.

Any subset S of identifiers in L may be converted into a corresponding query tree $Q_S$. For each leaf x corresponding to an identifier in S, $Q_S$ is first the tree denoted by the full paths that lead to any x in T(L). A node in $Q_S$ is denoted as full if all of its children (nodes following branches from the parent node) belong to $Q_S$ or if it is a leaf of $Q_S$. $Q_S$ is then be finalized by pruning all children of full nodes from $Q_S$, and iterating this step until no further pruning is possible. Remaining nodes form a connected sub-tree of T(L) which is the smallest sub-tree that selects exactly the identifiers of S. The number of nodes constituting this sub-tree indicates the size of the sub-tree and is upper-bounded by |S|×M nodes, because the largest instance of an appropriate sub-tree for S includes a distinct full path of length M for every leaf x corresponding to each identifier of S. As an example of pruning, the query tree Q in FIG. 20 has a partial path ending at what is considered a full node that has been pruned of its children, because all three identifiers in 2002a are part of a subset S.

In some implementations, S forms a contiguous range R=[id[x], id[y]] of (y−x+1) identifiers in L. R is converted into a corresponding contiguous range of leaves of T(L), and the above steps for generating $Q_S$ are applied. An example of this implementation is shown in FIG. 21, according to an illustrative implementation, which shows a graphical example of a decomposition of a contiguous range R of identifiers (represented by leaves) in a set of full and partial paths within a binary tree T(L). The leftmost and rightmost paths are two full paths leading to the leftmost and rightmost identifiers id[x] and id[y], respectively. Empty-circled nodes denote entire sub-trees descending from two nodes per level, given that the tree is binary. The "fan-out" of the nodes (i.e., number of components) at each level is denoted by c, which equals 2 for the example in FIG. 21. R is selected by a $Q_S$ consisting of at most 2(c−1) paths per (M−1) levels, so a $Q_R$ consists of at most 2(M−1)(c−1) queried paths and, hence, selectors. The number of paths is based on the factor (c−1) instead of c, because if there are c partial paths at some level i which originate from the same parent node, then these partial paths can be contracted or condensed to a shorter partial path ending at the shared parent node in the level above, still covering the same sub-range.

For a generic query tree Q, if the accessed identifiers are ordered in the order of the corresponding leaves of T(L), the identifiers form a range of contiguous identifiers with corresponding contiguous leaves $((s_1, t_1), \ldots, (s_n, t_n))$, where each $(s_1, t_1)$ is a non-empty, disjoint, and maximal contiguous subsequence of identifiers/leaves.

A suitable query tree $Q_S$ is one that: (i) satisfies the queried subset S, (ii) is feasible according to the adopted reading technology having certain limitations, and (iii) is minimized in reading cost. In some implementations, it is useful to read more identifiers than needed, such that $Q_S$ reaches some false-positive identifiers which are not in S and can be discarded at a post-processing step via automated or manual inspection. A case with minimized execution time for a query tree $Q_S$ may be implemented by pruning the tree Q one level after another, starting from the deepest level, until the total number of leaves covered by the current query tree is smaller than $f(R_{max}, \delta)$ (the maximum number of unique identifiers that may be read in a single run of a given reading method). A case with minimized number of nodes can be achieved by a greedy solution where every node u is assigned a priority prio(u) which measures a gain induced by removal of the node's children from the current query tree expressed as a function of the number of its children in Q (to be removed) and the number of extra leaves that are covered by the removal of those children. The greedy solution then proceeds by removing nodes from Q according to their priorities until the overall number of covered leaves by the pruned query tree is larger than $f(R_{max}, \delta)$.

As mentioned above, an access program may be used to overcome issues relating to feasibility of a given query, for example, if the set of identifiers to be read is larger than $f(R_{max}, \delta)$, or if sequencing the entire set of identifiers incurs an extraordinary expense. An access program P is a directed acyclic graph (DAG) in which: (i) each node is an access or read operation, (ii) each directed edge denotes the input/output between two nodes (possibly enriched in the concentration of identifiers present in the target library), (iii) the input to the root of the DAG is the original identifier library L, and (iv) the output of the DAG consists of as many (possibly non-disjoint) subsets of the library L as the number of its terminal nodes. The feasibility of P is guaranteed if, whenever a read operation is executed, then the pool of identifiers inputted to the read has a size smaller than $f(R_{max}, \delta)$. The feasibility depends on the concentration of identifiers in containers used to execute the query tree, which may be at least a fixed value $m_c$. In some implementations, to satisfy the concentration requirement, the identifiers in the target library L is replicated by an approximate constant $m_r$. In some implementations, in execution of a query tree consisting of l long downward paths (from root to node/leaf), the library L is partitioned into aliquots (volumetric partitioning of a sample) in l separate containers (e.g., wells in a well-plate, test tubes). The minimum concentration $m_c$ of each identifier may still be satisfied in each aliquot. Aliquoting involves pipetting from one container into/containers but may also be performed automatically by an automated liquid handling machine. Execution of l long independent paths over a trie T(L) of library L involves performing a replication operation with $m_r$=l which guarantees $m_c \times l$ copies per identifier. Then, an l-way aliquot operation is performed to partition the identifiers into l separate containers, each container having about $m_c$ copies per identifier. l accessors, for l long downward paths, are then executed over these l tubes, individually and/or in parallel.

In implementations where paths of a query tree are relatively short, they may be executed in parallel on the same container, requiring just one reaction, or a small number of reactions. In implementations where some paths are long and share some of the same sub-paths, then some reactions may be merged in the same container, reducing the number l of needed aliquots. Merging reactions is related to symmetry present in the structure of the query tree, so an access program may be configured to detect possible merges in the query tree.

FIG. 22 shows an example of this merging process on a query tree Q 2200 applied to a trie T(3), where letters A through I denote accessors, and branches that do not lead to a node are paths of the full trie 2200 that are not present in query tree 2200, according to an illustrative implementation. In the example of FIG. 22, tuery tree 2200 includes 6 full paths: ADG, ADH, AFG, CDG, CDH, and CFG. Every node specifies a chemical reaction with the selector or accessor labeling that node, and the reaction is executed over the identifiers from the incoming reaction (previous node). Based on the size and structure of query tree 2200, 12 total selectors are used overall, and at most, 6 reactions (one reaction per child node) per level are required.

Query-DAG 2202 on the right side of FIG. 22 is a result of merging shared suffixes in query tree 2200. Query-DAG 2202 merges shared suffix FG between AFG and CFG, shared suffix DG between ADG and CDG, and shared suffix DH between ADH and CDH. The resulting query-DAG 2202 is implemented with 6 accessors and no more than 2 reactions per level. A number of aliquots at a node depend on its fan-out, so query-DAG 2202 is implemented with no more than a 2-way aliquot operation, with at most 2 containers per level and thus a 2-way replication operation at most per level.

In general, an access program is implemented using a query tree consisting of l downward paths (selectors). In some implementations, the query tree is shallow, meaning the paths have length $p \leq \pi$, where $\gamma L$ is as defined above depending on the read technology, then one reaction is sufficient for executing the query tree. The query tree consists of the OR logical of the paths, i.e., the selectors' results, so the selectors may be applied in parallel on the same container. In some implementations, the query tree has some paths longer than π and must be executed by the AND of (p/π) accessors which are differentiated in execution. However, these limitations may be overcome in implementations where the query tree comprises one or more repetitions occurring in corresponding downward paths. A form of repetition is as described above in relation to FIG. 21, the repetition being a shared suffix among two or more paths in the query tree corresponding to an access operation. When two paths share a suffix s, such as the DG suffix in two paths ADG and CDG of 2200 of FIG. 21, they share the last sequence of |s| selectors, so the sets of identifiers selected by the two paths may be merged into the same container. This process involves transforming a query tree $Q_S$ like 2200 into a query-DAG $D_S$ like 2202, where the transformation involves collapsing equal suffixes of paths in $Q_S$. Nodes in $D_S$ are labeled with accessors (π-long selectors), and each node denotes a reaction which is performed by applying the corresponding accessor over the identifiers which are merged in a container according to the sub-paths. The number of reactions to be executed in parallel by the access program is equal to the number of nodes in each level of $D_S$.

In some implementations, an access program has a query tree that is the OR logical of its constituting paths, and a query path length of p≤L is executed by combining in AND logical(s) its constituting (p/π) accessors. The access program involves execution of r paths of length at most p, which may be decomposed level-wise in a sequence of (p/π) sets of at most r accessors each (one accessor per path). Each such set is executed via one reaction operating over a container. This implementation over-estimates the material cost of the access program, for example, if the paths share some prefixes (and may thus be executed together), or if merging parts of the paths reduces the number of aliquot and replication operations (and thus the number of parallel reactions). An execution time of an access program specified by a query tree Q with m leaves is proportional to its depth divided by π: (1/π)×depth(Q). The access program proceeds by executing one reaction per π levels of the query tree Q, which may involve executing many accessors over possibly distinct containers. The execution time accounts for time taken by replication and aliquoting. In some implementations, query tree Q is contracted by keeping nodes at levels that are multiples of r and contracting sub-paths of π-components to form a meta-component of length π, which are considered as a single symbol. At every π levels, $c^\pi$ paths are explored, so the contracted trie has a depth of L/π and fan-out of $c^\pi$. A node has a fan-out f, and then its input, from the parent node, is replicated f times. In implementations where a query is executed according to a query-DAG D derived from tree Q, then the execution time is approximated by (1/π)×depth(D) plus the replication time which is determined as before based on the nodes of the D, taking into account each node's fan-out. This execution time may be smaller than the execution time for Q, because depth(D)=depth(Q) and |D|≤|Q|, per the definition of the query-DAG discussed above.

A setup time of the access program is proportional the size of Q divided by π, given that an accessor is formed by π components. The setup time is bounded above by the size: |Q|, or a sum of the lengths of the m individual paths divided by π: (1/π)×m×depth(Q), whichever is less. The corresponding query-DAG $D_S$ to $Q_S$ are used in place of Q to specify the setup time.

The read and access operations discussed herein form the basis for performing other operations on a DNA-based storage system.

Rank and Fetch Operations of Data Stored in Nucleic Acid Sequences

Figure 23:
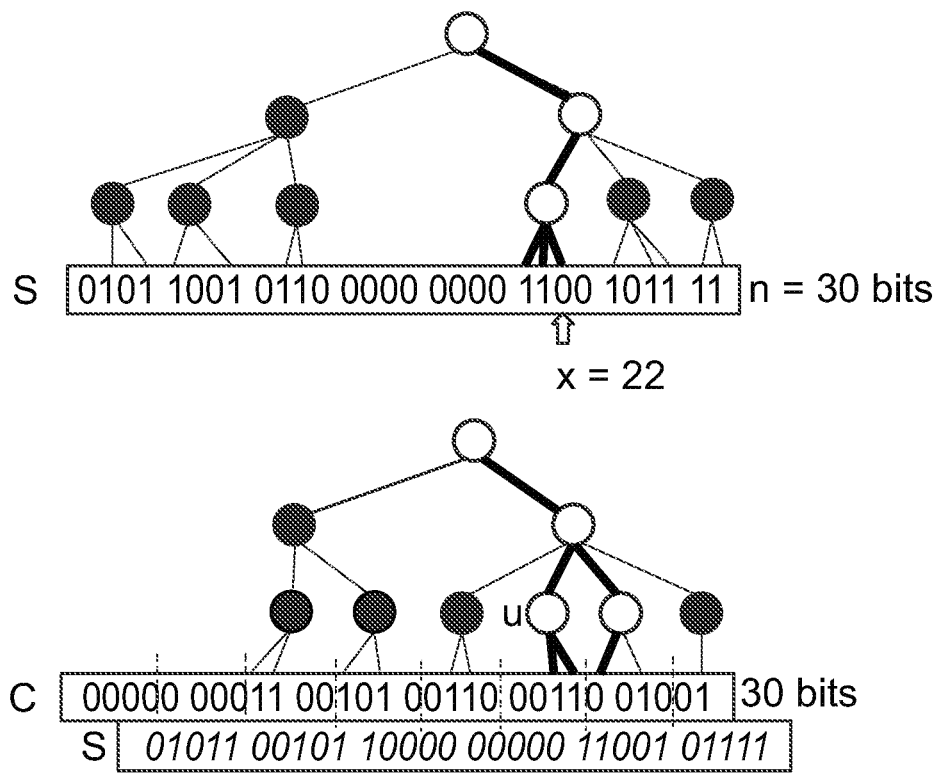
FIG. 23 shows a graphical example of execution of a rank operation on a binary string.
Figure 24:
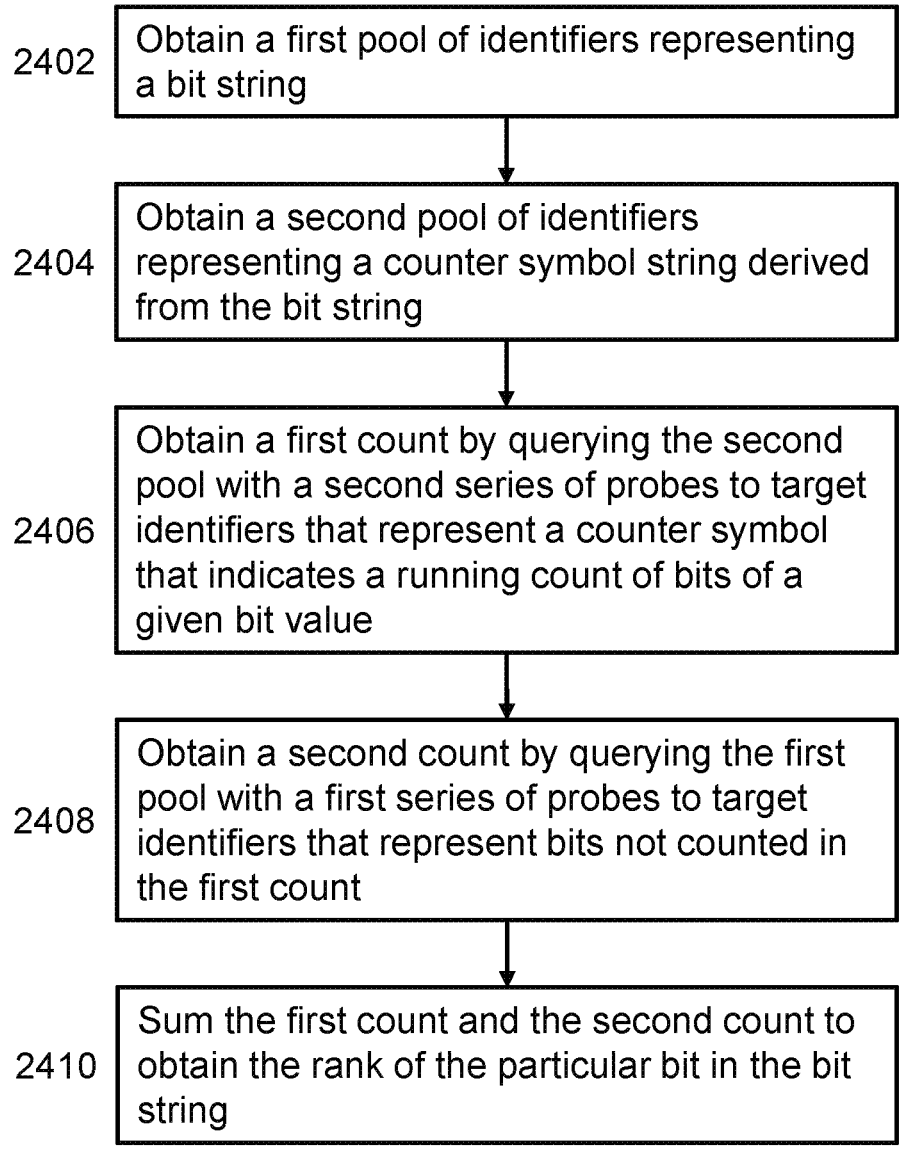
FIG. 24 shows a flowchart for execution of a rank operation.

FIGS. 23 and 24 depict exemplary methods of performing a rank operation to determine a count of a symbol or bit value for a range of a data string, up to and including a particular position in the string, according illustrative implementations. The rank operation includes multiple access and read operations, described above. Similarly, a fetch operation may be performed to retrieve a subset of a string of symbols. As discussed above, aspects of this disclosure relate to storing, indexing, and searching binary strings. A string S of length n binary bits may be represented by identifier nucleic acid molecules via a pool of identifiers $L_S$ built with M components chosen in sets of size c. For example, the size |L[M]| of the combinatorial library L is set equal to $c^L \geq n$, so the number of layers M is approximated by $\log_c n$. String S is encoded as a pool of identifiers such that the identifier id[x] in position x belongs to $L_S$ if the bit S[x] at position x in S has a bit value of 1. In some implementations, this means that only identifiers in L corresponding to bit values of 1 are constructed and subsequently pooled, while identifiers in L corresponding to bit values of 0 are not constructed.

The present disclosure includes systems and methods that perform a rank operation rank(x) which, for a binary string, returns the count of the number of 1's in the prefix string S[0,x](the portion of the bit string S which precedes and includes position x). For a nonbinary string, the rank operation returns the count of the number of symbols having a specific symbol value in the prefix string. While some of the examples described herein relate to binary strings, it will be understood that the present disclosure applies to rank operations for symbol strings having more than two possible symbol values.

In some implementations, b is the number of bits needed to encode the integer n indicating the length of the binary bit string S. The number of bits b is estimated by $\log_2(n+1)$. String S is divided into blocks of size b, and the block which includes the position x in string S may be denoted by B(x). Counting from 0 at one end of string S, the ordered index B(x) is equal to floor(x/b). Computation of rank may be decomposed into two steps: (i) count the number of 1's in S[0, b×B(x)−1] (the number of 1's in the blocks preceding the block B(x) containing x); and (ii) count the number of 1's in S[b×B(x), x] (the number of 1's in block B(x) up to and including x). These steps can be done in any order. The counts from both steps is then summed to determine the rank at position x. In some implementations, the operation rank (x) is implemented via an access program which consists of two access operations and two read operations, executable in parallel, because each pair of an access operation and a read operation are applied to a distinct target library, a distinct target library corresponding to each step (i) and (ii).

While some of the examples described herein relate to the above two steps, the present disclosure includes other ways of determining rank that reach equivalent results. For example, in some implementations, the two steps described above are slightly modified. Specifically, computation of rank may be decomposed into two different steps: (i) count the number of 1's in S[0, (b+1)×B(x)−1] (the number of 1's in the blocks preceding and including the block B(x) containing x); and (ii) count the number of 1's in S[x+1, (b+1)×B(x)] (the number of 1's in block B(x) that were included in step (i) but occur only after x). Then, the count from step (ii) is subtracted from the count at step (i) to obtain the rank at position x, by removing the number of 1's that were double counted in steps (i) and (ii). More generally, the string S may be divided into a block size, w, which need not be the same as b. In some implementations, the operation rank(x) is implemented via an access program which consists of two access operations and two read operations, executable in parallel, because each pair of an access operation and a read operation are applied to a distinct target library, a distinct target library corresponding to each step (i) and (ii).

FIG. 23 shows an example for the calculation of rank(22) in a binary string S of n=30 bits stored using identifiers according to the methods described herein, according to an illustrative implementation. Accordingly, this operation determines the number of bit values of 1 in the positions up to and including position x=22 in S. In this example, the target library $L_S$ includes 13 identifiers which correspond to 13 bits set to a value of 1 in S. The identifiers are composed of 3 components each, corresponding to the 3 levels in each trie in FIG. 23. The trie $T_S[3]$ above string S in FIG. 23 accordingly consists of 13 leaves (corresponding to the 13 identifiers for the 1 bits), 3 levels above the leaves, and a fan-out of c=4. Only the paths leading to existing leaves (identifiers corresponding to bit value 1) are drawn.

The first query tree in FIG. 23 corresponds to step (ii) of the rank operation as discussed above. The block size b in this example equals log(n+1)=5, and the block containing position 22 is B(22)=4. Query tree $Q_R$ (indicated with thicker lines in the tree structure) covers a range R[20, 22] from position 20 to position 22. $Q_R$ consists of three full paths that select the three leaves at positions 20, 21, and 22 corresponding to bit values of 1, 1, and 0, respectively. Only two of these values are equal to 1, so the identifiers at positions 20 and 21, id[20] and id[21], respectively, are retrieved. The count for this query tree $Q_R$ is set to $n_S=2$, corresponding to the number of 1's in B(22) up to and including position x=22, in accordance with step (ii) set out above.

The remaining 1's in the blocks preceding B(22) may now be determined in accordance with step (i) of the rank operation. This step is performed by referencing a binary counter string C which encodes ceiling(n/b)=6 counters of b=5 bits each. C is stored using identifiers according to the methods described herein and may accordingly be accessed and read similarly to S. Each 5-bit counter of C counts the number of 1's in the prefix of S preceding each counter. S is copied below C for reference. The first 5-bit counter of C equals 0 in binary, because there is no prefix of S preceding the first counter. The second 5-bit counter is "00011" which equals 3 in binary, because it follows the first block of S which contains 3 1's. The bits of C are separated by dotted vertical lines to denote groups of 4 bits corresponding to the c=4 fan-out of the query tree $Q_C$ applied to C. $Q_C$ applied to C selects identifiers in the range C[20,24], corresponding to the counter of the number of 1-bits in S[0,19], the prefix of B(22). $Q_C$ consists of one partial path, ending at the node u, and one full path that covers the bit in position 24. The identifier id[24] at position 24 does not exist, because its corresponding bit is set to 0, so the full query path does not retrieve anything. The partial path ending at node u retrieves two identifiers id[22] and id[23] at positions 22 and 23, respectively. The bits of the counter C[20,24] read out "00110" which encodes the integer value 6, corresponding to the number of 1's in S[0,19], the prefix of B(22). The count for this query tree $Q_C$ is set to $n_C=6$, corresponding to the number of 1's in S up to B(22), in accordance with step (i) set out above. Execution of this exemplary rank operation via access program returns $n_S+n_C=2+6=8$, which is the correct number of 1-bits in S[0,22].

As described above and shown by example in FIG. 23, computation of rank may be decomposed into two steps: (i) count the number of 1's in S[0, b×B(x)−1] (the number of 1's in the blocks preceding the block B(x) containing x); and (ii) add the number of 1's in S[b×B(x), x](the number of 1's in block B(x) up to and including x). This operation is formalized for a bit string S of length n and executed according to the following phases. Phase 1 involves computing the number $n_1(C)$ of 1's in S[0, b×B(x)−1], the prefix of block B(x). Prefix refers to the bits preceding a certain bit or block. A first target library $L_C$ represents the binary string C[1, b×B(n)], the counter string for a string S. Counter string C is defined such that C[ib, (i+1)b−1] stores the binary representation in b bits of the value rank(ib−1) of S, where i=1, . . . B(n)−1. C has a length≤n (less than or equal to the length of S). C(0) is not stored, because it is equal to 0 according to the definition. Phase 1 involves creating a query tree $Q_C$ which fetches identifiers of the first library $L_C$ in the range $R_C$=(id[b×B(x)], id[b×(B(x)+1)−1]), corresponding to the counter of C that encodes the rank of S up to the block B(x) containing the specified position x. $Q_C$ has a depth on the order of $\log_c n$ and size on the order of cL, the depth times the fan-out, where the size is independent of block size b. Phase 1 then involves creating the access program which reads the bits constituting the substring of C delimited by $R_C$ via two operations: Y=access($L_C$, $R_C$) (accessing the identifiers of $L_C$ in the range $R_C$) and then read(Y), where Y is the subset of identifiers obtained via the access operation. This access program is feasible, according to the previously discussed criteria, because the read operation is executed over a range of at most b identifiers, where b is on the order of log(n), which is less than $f(R_{max}, \delta)$. The identifiers retrieved by the access program denote the positions of the 1-bits in the sub-string of C delimited by $R_C$. Phase 1 culminates by setting $n_1(C)$ to the integer value encoded by the binary sub-string of b bits in which only those positions are set to 1.

Phase 2 involves computing the number $n_1(R)$ of 1's in S[b×B(x), x], the sub-string of S corresponding to the block B(x) that contains position x. A second target library $L_S$ represents the binary string S such that an identifier physically exists if the bit value at the corresponding position in S is equal to 1, i.e., id[x] exists if and only if S[x]=1. Phase 1 involves creating a query tree $Q_R$ which fetches identifiers of the second library $L_S$ in the range $R_S$=(id[b×B(x)], id[x]), corresponding to the positions of block B(x) in S up to and including position x. $Q_R$ has a depth on the order of $\log_c n$ and size on the order of cL, the depth times the fan-out. Phase 1 then involves creating the access program which reads the bits constituting the substring of S delimited by $R_S$ via two operations: X=access($L_S$, $R_S$) (accessing the identifiers of $L_S$ in the range $R_S$) and then read(X), where X is the subset of identifiers obtained via the access operation. The identifiers retrieved by the access program denote the positions of the 1-bits in the sub-string of S delimited by $R_S$. Phase 2 culminates by setting $n_1(R)$ equal to the number of retrieved identifiers. The rank operation concludes by returning the value $n_1(C)+n_1(R)$, from phases 1 and 2, respectively, where rank is the number of 1-bits in S in the range from 0 to position x.

FIG. 24 shows a flowchart 2400 for performing a rank operation on a bit string, according to an illustrative implementation. The methods described above for FIG. 23 and the general case with phases 1 and 2 may be used in the method of flowchart 2400. At step 2402, a first pool of identifiers representing the bit string, such as S above, is obtained. At step 2404, a second pool of identifiers representing a string of counter symbols, such as C above, is obtained. At step 2406, a first count is obtained by accessing the second pool, using a second series of probes, which may be sequential, to target identifiers that indicate a running count of bits of a particular value. The targeted identifiers represent a counter symbol that indicates the running count of the number of bits of a given value is obtained for either (1) all blocks of w bits preceding the particular bit, or (2) all blocks of w bits preceding the particular bit and including the block of w bits that includes the particular bit. At step 2408, a second count is obtained by accessing the first pool, using a first series of probes, which may be sequential, to target identifiers. The targeted identifiers either (1) represent bits not counted in step 2406 and preceding or including the particular bit, or (2) represent bits that were counted in step 2406 but that do not precede or include the particular bit. At step 2410, the rank of the particular bit in the bit string is obtained from the first count and the second count (e.g., by determining the sum or difference of the counts).

Each bit in the bit string has a bit value and a bit position. Each pool may have a solid, liquid, or solid form and is formed by forming a plurality of identifier nucleic acid molecules. Each identifier corresponds to a respective bit position and is formed by physically assembling M selected component nucleic acid molecules. Each of the M selected components is selected from a set of distinct component nucleic acid molecules that are separated into M different layers. The identifiers may be collected in the first pool to represent the string of bits such that the bit values are indicated by a presence or absence of the corresponding identifier in the first pool. Similarly, the second pool of identifiers are formed by collecting the identifiers that each represent a bit in the counter string. In some implementations, the first pool is the same as the second pool, and, in other implementations, the first pool and the second pool are separate.

In some implementations, the physical presence of corresponding identifiers in the first pool indicates the bit value of 1, and the physical absence of corresponding identifiers indicates the bit value of 0. Each counter symbol may be represented by a string of b counter bits, and b may be determined by the ceiling of the function $\log_2(n+1)$, where n is the length of the bit string. Each string of b counter bits may represent a running count of a number of bits for every w bits in the bit string that have a specific value, e.g., 1 or 0. The string of counter symbols may include a ceiling of n divided by w counter symbols and is represented by a string of counter bits having length n. In some implementations, an initial counter symbol has value zero, represented by a string of b counter bits all having value 0. If the particular bit is within the first block of w bits, then the running count preceding the first block of w bits is zero.

The first and second counts are obtained by reading the targeted identifiers from each query, according to the read operations described herein. For example, the first count is obtained by reading the counter symbol value corresponding to the targeted identifiers in 2406, or the second count is obtained by reading the targeted identifiers in 2408. In some implementations, the first index of each string is set equal to 0. The counter symbol used to obtain the first count in step 2408 may correspond to a number of bits in the string of bits that have value 1 within the range 0 to w×B(x)−1, where x corresponds to the particular bit's position in the string of bits, and B(x) is the floor of x divided by w. At least b identifiers may be targeted from the second pool, and the targeted at least b identifiers may be within the range b×B(x) to b×(B(x)+1)−1.

In some implementations, the second count corresponds to a number of bits in the string of bits that have value 1 within the range w×B(x) to x, where x corresponds to the particular bit's position in the string of bits, and B(x) is the floor of x divided by w. In step 2408, the first count may be obtained by targeting identifiers queried from the second pool that represent the counter symbol corresponding to blocks of w bits including the particular bit, and the second count in step 2412 are obtained by targeting and counting the unique identifiers targeted in 2410 that represent bits that were counted in 2408 but that do not precede or include the particular bit. Accordingly, the rank is obtained in 2414 by subtracting the second count from the first count.

In some implementations, the counter string block size w may be set equal to the bit string block size b. Alternatively, counter string block size w may be set to 1. The first count in 2408 may be obtained by targeting identifiers queried in the second pool in 2406 that represent the counter symbol corresponding to the blocks of w bits including the particular bit, and wherein the rank is equivalent to the first count. Accordingly, steps 2412 and 2414 may be omitted from the method.

In some implementations, the first pool of identifier nucleic acids represents a translation of the string of bits such that the presence or absence of identifiers does not correlate directly with one bit value or another in the string of bits, but such that blocks of contiguously ordered identifiers referred to as codewords can be translated to blocks of bits in the string of bits. Codewords comprise the presence of a fixed number of unique identifier acid molecules out of a fixed number of possible unique identifier nucleic acid molecules. Additional information may be used to detect and correct errors in writing, accessing, and reading identifier nucleic acid molecules from the first and second pools. Said additional information is stored in the identifiers of the first and second pools.

In some implementations, the first count in 2406 represents all blocks of w bits preceding the particular bit, the first series of probes in 2408 targets one or more distinct identifier nucleic acid molecules within the first pool that represents bits not counted in 2406 and preceding or including the particular bit, and the rank of the particular bit in the string of bits is obtained by summing the first and second counts in 2410. In other implementations, the first count in 2406 represents all blocks of w bits preceding the particular bit and including the block of w bits that includes the particular bit, the first series of probes targets one or more distinct identifier nucleic acid molecules within the first pool that represents bits counted in 2406 but that do not precede or include the particular bit, and the rank of the particular bit in the string of bits is obtained by subtracting the second count from the first count in 2410.

In some implementations, the size of binary blocks to be read in S is adjusted. Increasing the block size reduces the number of counters in C and thus reduce the length of C. For example, by setting w as the length of binary blocks in S, the length of C becomes on the order of (n/w)log(n), and w is the amount of bits fetched from read(X) in phase 2. In the above decomposition, the size of C was chosen to be less than or equal to n, the size of S, by setting w approximately equal to log(n).

It is to be understood that, while the rank operation described by method 2400 focuses on binary strings of bits, method 2400 may also be applied to a string of symbols. In some implementations, the string of bits represents a string of symbols, and the rank is obtained for a particular symbol in the string of symbols. The symbols in the string of symbols are selected from a set of symbol values, and the string of counter symbols in 2404 is indicative of a running count of a number of symbols having a particular symbol value. In some implementations, there are multiple second pools of identifiers in 2404, and each second pool represents different strings of counter symbols that count the number of instances of specific symbol values, each different string of counter symbols counting instances of a corresponding specific symbol value.

The example above, in FIG. 23, and any binary rank operation may be alternatively executed by counting the number of 0-bits in S, this operation being denoted by $rank_0(x)$. $rank_0(x)$ may be computed as $rank_0(x)=x-rank_1(x)+1$. The rank operation may also be performed on a string of symbols selected from a set of symbol values, obtaining the rank for a particular symbol in the string of symbols. For example, the string of counter symbols is indicative of a running count of a number of symbols that have a specific symbol value. In step 2404, different pools of identifiers represents different strings of counter symbols that count the number of instances of specific symbol values, each different string of counter symbols counting instances of a corresponding specific symbol value.

In some implementations, the number of identifiers that must be read to perform a given rank operation is very small even if the rank operation is performed on a large bit string (e.g., a large input message). For example, ranking a particular bit in a terabit-size message involves reading as few as 40 to 100 identifiers, depending on the configuration. With this small amount of identifiers, reading may be performed by a low-throughput hybridization method such as a DNA micro-array or PCR (e.g., qPCR or digital PCR), rather than using higher-throughput methods like DNA sequencing have a higher associated cost.

Another operation that may be performed on the DNA-based storage systems described herein is a fetch operation, for example, by extending the above process for retrieving one entry from the counter array C to deal with an integer array. Given an array of n integers consisting of b bits each, the array may be converted into a binary string by serializing the n integers in a b-fixed size representation. The converted binary string is represented as A[0, nb−1], because the serialization leads to a binary string of length n times b. A is represented by a pool of identifiers LA, encoded according to the methods described herein, where each identifier is physically constructed if it corresponds to a bit value of 1 in A (i.e., id[x] if and only if A[x]=1). The fetch operation is defined as fetch(x,y) which returns the integers occurring in the range [x,y] and are represented by the b-long binary strings starting at positions determined by the range and the string length (i.e., at positions i×b for i=x, . . . , y). The fetch operation accesses the identifiers of LA representing a sub-array of A delimited by a first position xb and a last position (y+1)b−1. The fetch operation is implemented by an access program consisting of one access operation and one read operation.

The access program for the fetch operation may be executed as follows. The target library LA represents the binary string A as described above. A query tree $Q_A$ is created that selects identifiers in the range $R_A$, as described above, that is delimited by a first position xb and a last position (y+1)b−1 (i.e., $R_A$=(id[x×b], id[(y+1)b−1])). The range $R_A$ covers exactly all the bits of A which represent the integers of the input array (the un-serialized integer array) that occur at positions in the range x toy (i.e., [x,y]). The sub-string of A delimited by $R_A$ is accessed, according to the access methods described herein, and the identifiers included in that sub-string are read, according to the read methods described herein. This access program has depth on the order of $log_c$ A which is equal to $log_c$ nb, and has a size on the order of $log_c$ A which is equal to $log_c$ nb. The range $R_A$ has a size equal to (y−x+1)×b bits. The identifiers retrieved by the access program may be used to reconstructed the y−x+1 integers stored at the positions in the range [x,y] of the input integer array. This fetch operation may be executed in an execution time on the order of (y x).

Figure 25:
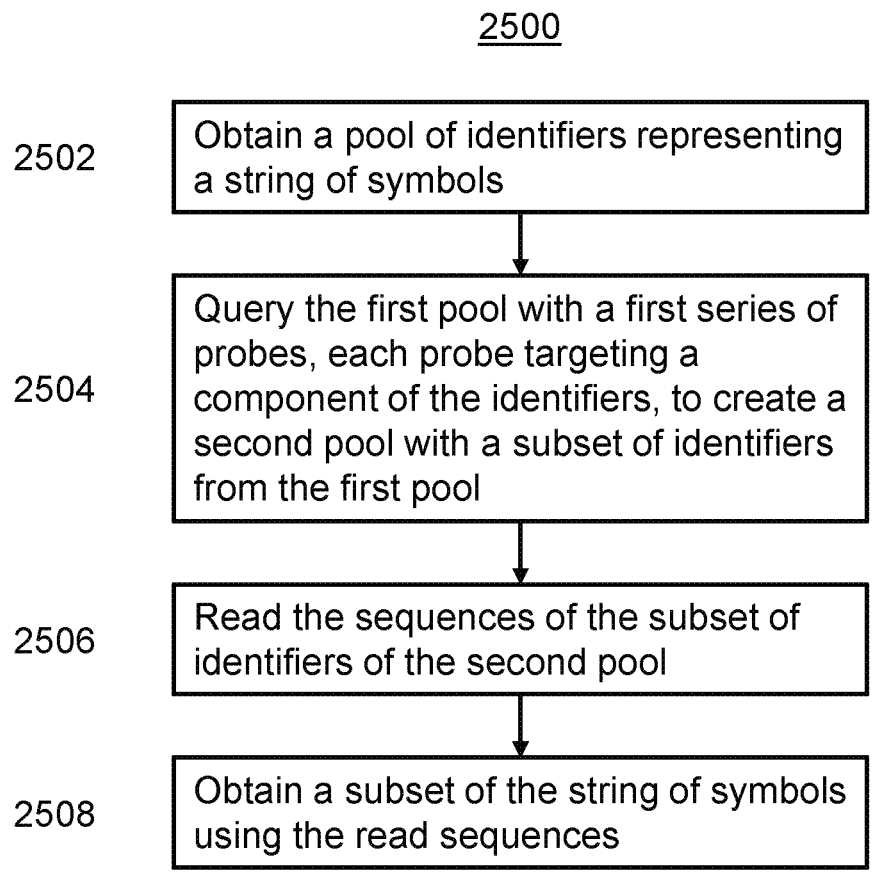
FIG. 25 shows a flowchart for execution of a fetch operation.

FIG. 25 shows a flowchart for execution of a fetch operation on a string of symbols, according to an illustrative implementation. The methods and logic described above may be used in this method of FIG. 25 to perform the fetch operation. The string of symbols Step 2502 involves obtaining a first pool of identifiers representing the string of symbols. Step 2504 involves accessing the first pool with a first series of probes, each probe targeting a component of the identifiers of the first pool, to create a second pool with a subset of identifiers from the first pool. Step 2506 involves reading the sequences of the subset of identifiers in the second pool. Step 2508 involves obtaining a subset of the string of symbols using the read sequences.

In the string of symbols, each symbol has a symbol value and symbol position. In some implementations, step 2502 involves forming a plurality of identifier nucleic acid molecules, each identifier corresponding to a respective symbol position and formed by physically assembling M selected component nucleic acid molecules. Each of the M selected components are selected from a set of distinct components that are separated into M different layers. The components of each layer may be logically ordered, such as is described in relation to FIG. 13. The identifiers may be collected in the pool to represent the string of symbols, such that the symbol values are indicated by a presence or absence of the corresponding identifiers in said pool.

In some implementations, in step 2504, the first series of probes is sequential and corresponds to a partial or full downward path in a query tree representative of the M layers of components. A full downward path corresponds to a root-to-leaf path that includes M probes, such that the sequential series of the M probes targets a single identifier. A partial downward path corresponds to fewer than M probes, such that the sequential series of the probes targets multiple populations of identifiers having different sequences. The multiple populations of identifiers having different sequences may correspond to different components in at least the $M^{th}$ layer.

In some implementations, in step 2504, querying the first pool involves using a first probe in the first sequential series of probes to capture a first component nucleic acid molecule in a first layer within the first pool; separating the first pool into at least two pools in separate compartments; and using additional probes to capture component nucleic acid molecules in a second layer within the at least two pools. The first sequential series of probes may be designed to obtain a desirable portion of the string of symbols including the subset. The desirable portion may correspond closely to the subset obtained in step 2504.

In some implementations, the first pool obtained in step 2502 is split into at least two duplicate pools, and steps 2504-2508 are executed on each of the said duplicate pools. The first pool may be replicated (e.g., via PCR) prior to being split into the at least two duplicate pools. The probes in step 2504 may be PCR primers, and accessing is performed by PCR. Alternatively, the probes in step 2504 may be affinity tagged oligonucleotides, and accessing is performed by an affinity pull-down assay. In some implementations, method 2500 further comprises accessing a first pool of identifiers with a sub-series of probes to create an intermediate pool of identifiers. The intermediate pool may be split into at least two duplicate pools. A first intermediate pool may be accessed with a subsequent sub-series of probes to form a second intermediate pool or a second pool. At least two intermediate pools may be combined to form another intermediate pool.

In some implementations, the fetch operation uses a hybridization-based approach like DNA micro-arrays or PCR (e.g., qPCR or digital PCR) for reading of identifiers. For example, if the targeted identifiers are in a small amount, it may be more cost-effective to use a low throughput method; however, if a large subset of identifiers must be read, DNA sequencing may be used for high throughput reading.

Pattern Searching in Data Stored in Nucleic Acid Molecules

As mentioned above, another operation that may be performed on the DNA-based platform is a count operation that relies on the BWT of a string and the rank operation. At the basis of the count operation is the use of two rank operations that may be executed in parallel, because each rank operation either insists on different parts of the BWT and of a counter array, or these parts overlap, and their execution can be structured in order to reuse the results of some operations. Described in the following is a search method which deploys the BWT, the counter array, and the rank operation.

With the data structures implementable on the systems described herein, a count operation may be performed to count the number of occurrences of a pattern P in a string. This count operation is described in relation to FIGS. 26-30. At the basis of the count operation is the use of two rank operations that may be executed in parallel, because each rank operation either insists on different parts of the BWT and of a counter array, or these parts overlap, and their execution can be structured in order to reuse the results of some operations. The retrieval of pattern occurrences is not necessarily implemented via a binary search, but the systems described herein may use a search method which deploys the BWT, the counter array, and the rank operation. These operations/data structures may be stored in a compressed fashion while still permitting retrieval of their entries.

A count operation may be performed by obtaining a first pool of identifiers representative of a string of bits L which is a last column of a Burrows-Wheeler Transform matrix of, for example, a message. Each identifier is assembled according the methods described herein and is capable of individually binding to one or more probes. A second pool of identifiers is obtained, representative of a string of counter symbols that is derived from the bit string L and represent a running count of a number of bits having a specific bit value. The count of a particular bit pattern in the message is obtained by selectively accessing identifiers from the first and second pools. A series of probes are used to access identifiers from the first and second pools. The running count may be used to reconstruct a first column F of the BWT matrix, for example, by using LF-mapping as described below.

Figure 26:
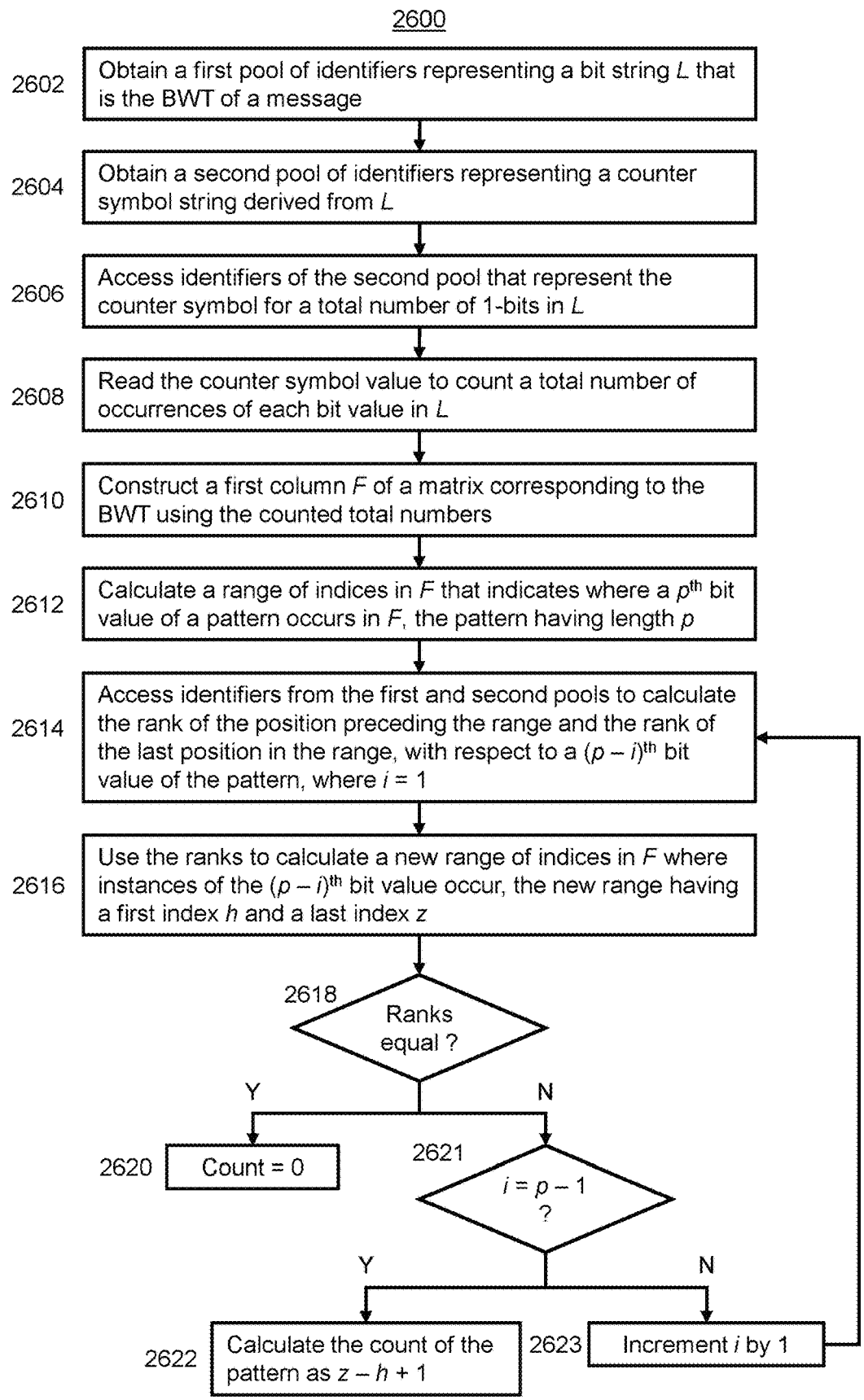
FIG. 26 shows a flowchart for execution of a count operation on a binary string.

FIG. 26 shows a flowchart for a count operation method 2600, for counting the number of occurrences of a particular pattern P in a binary bit string S that may be, for example, a message or some other form of information, according to an illustrative implementation. The BWT L of S is stored via representation by identifiers in a first pool. Step 2602 involves obtaining the first pool if identifiers, representing the BWT L. In step 2604, a second pool of identifiers is obtained, the identifiers of the second pool representing a counter symbol string derived from L. In step 2606, identifiers of the second pool are accessed, using the methods described herein, to retrieve identifiers that represent the counter symbol that indicates the total number of occurrences of bit value 1 in L. Step 2608 involves reading the counter symbol value from the retrieved identifiers to count a total number of occurrences of each bit value in L (e.g., the total number of 1's or 0's for the binary string). In step 2610, the first column F of the Burrows-Wheeler matrix is constructed using the total numbers counted in step 2608. Step 2612 involves determining indices of a range in the first column F that indicates all occurrences of the last symbol in the pattern P (i.e., the $p^{th}$ symbol for a pattern of length p). Step 2614 involves access identifiers from the first and second pools to calculate the ranks at the first and last indices h and z of the range, the ranks being determined with respect to the value of the symbol that precedes, in the pattern P, the symbol of the range (i.e., the $(p-i)^{th}$ symbol in P, where the loop counter i is initially equal to 1). In step 2616, the ranks at each index are used to calculate indices of a new range in the first column F where the value of the preceding symbol $((p-i)^{th}$ symbol) occurs. At decision block 2618, the ranks $r_{h-1}$ and $r_z$ are compared to check if they are equal. If the ranks are determined to be equal (Y), then method 2600 proceeds to step 2620 and outputs a count of zero, indicating that there are no occurrences of pattern P in the string S. If the ranks are not equal (N), then method 2600 proceeds to decision block 2621 where it is checked if i equals p−1 (indicating the end of the pattern). If i equals p−1 (Y), then method 2600 proceeds to step 2622, where the count of the pattern P is determined to be z−h+1. If i does not equal p−1 (N), then method 2600 proceeds to step 2623 where loop counter i is incremented by 1, and the process returns to step 2614 for at least one more iteration of steps 2614-2618. Steps 2612-2616 are iterated until the first symbol of P is reached, and the count is output at step 2622, or until it is determined there are no occurrences of the pattern P in the string S, and a count of zero is output at step 2620.

Each bit in the bit string has a bit value and a bit position. Each counter symbol may be stored in a counter symbol string that is a serialized counter array. Each counter symbol may be represented by a string of b counter bits indicative of a running count of a number of bits, for every w bits in the string of bits L that have a specific bit value, e.g., '1'. Step 2612 may involve determining a first position h and a last position z that define the range in F of occurrences of the $p^{th}$ bit value of the pattern P, where the range is inclusive of h and z. Step 2614 may involve calculating, at position h−1 in the string L, the rank $r_{h-1}$ of the $(p-i)^{th}$ bit value of pattern P, where the loop counter i is initially 1. Step 2614 may further involve calculating, at position z in string L, the rank $r_z$ of the $(p-i)^{th}$ bit value of pattern P. If $r_{h-1}$ is equal to $r_z$, then the count of occurrences of the pattern in the message may be set to zero. Step 2616 may involve setting h to the index of the $(r_{h-1+1})^{th}$ instance in F of the $(p-i)^{th}$ bit value and setting z to the index of the $r_z^{th}$ instance in F of the $(p-i)^{th}$ bit value, where the new h and z define a new range. After h and z have been recalculated, the loop counter i may be incremented by 1, and steps 2614-2616 are repeated until i=p−1. Iterations of steps 2614-2616 may be performed sequentially, or the iterations may be performed in parallel reactions, for example, using query tree optimization methods described in the foregoing.

Each pool may have a solid, liquid, or solid form and may be formed by forming a plurality of identifier nucleic acid molecules. Each identifier may correspond to a respective bit position and may be formed by physically assembling M selected component nucleic acid molecules. Each of the M selected components may be selected from a set of distinct component nucleic acid molecules that are separated into M different layers. The identifiers may be collected in the first pool to represent the string of bits such that the bit values are indicated by a presence or absence of the corresponding identifier in the first pool. Similarly, the second pool of identifiers may be formed by collecting the identifiers that each represent a bit in the counter string. In some implementations, the first pool is the same as the second pool, and, in other implementations, the first pool and the second pool are separate.

In some implementations, the physical presence of corresponding identifiers in the first pool indicates the bit value of 1, and the physical absence of corresponding identifiers indicates the bit value of 0. Each counter symbol may be represented by a string of b counter bits, and b may be determined by the ceiling of the function $\log_2(n+1)$, where n is the length of the bit string. Each string of b counter bits may represent a running count of a number of bits for every w bits in the bit string that have a specific value, e.g., 1 or 0. The string of counter symbols may include a ceiling of n divided by w counter symbols and may be represented by a string of counter bits having length corresponding to b multiplied by the ceiling of n divided by w. In some implementations, an initial counter symbol has value zero, represented by a string of b counter bits all having value 0. In some implementations, the counter string block size w may be set equal to the bit string block size b. Counter string block size w may be set to 1. In some implementations, step 2602 is omitted from method 2600.

In some implementations, the first pool of identifiers represents a translation of the string L that represents codewords corresponding to blocks of contiguously ordered identifiers that are translated to blocks of bits in L. The presence or absence of identifiers in the first pool does not correlate directly with one bit value or another in the string of bits. The codewords may correspond to a fixed number of unique identifiers out of a fixed number of possible unique identifiers. Additional information may be stored. For example, additional information may be stored for use in detecting and correct errors in writing, accessing, and reading identifiers from the first and second pool. The additional information may be stored in the identifiers of the first or second pool.

For a pattern of length one, such as simply the bit value 1 or 0, steps 2614 through 2618 may be omitted. For pattern of length two, such as '01' or '11', step 2618 may be omitted, because no iteration is needed. The method may further involve stopping the method if the range in the first column F is determined to be non-existent, and the count is returned as zero. If the range is non-existent then the symbol of pattern P does not exist in the string, and thus there are zero occurrences of P.

In some implementations, a third pool of identifiers are obtained, the identifiers in the third pool representing a suffix array SA derived from the BWT. Each element of the SA may be represented by a bit string of at least $\log_2(n)$ bits indicative of the index of the corresponding element of L. Method 2600 may further involve locating the occurrences of the pattern, given that the count is greater than zero, by accessing the identifiers in the third pool corresponding to the elements of the suffix array between and including the final values of indices h and z of the range. These indices may be the indices of the final range when the count of occurrences is returned. These steps may be performed as a fetch operation.

In some implementations, method 2600 further involves obtaining a fourth pool of identifiers representative of the bit string S, which may be a message for example. The context of a first location of the pattern P may be extracted by accessing the identifiers in the fourth pool corresponding to the first location and the neighboring positions surrounding the first location.

Figure 27:
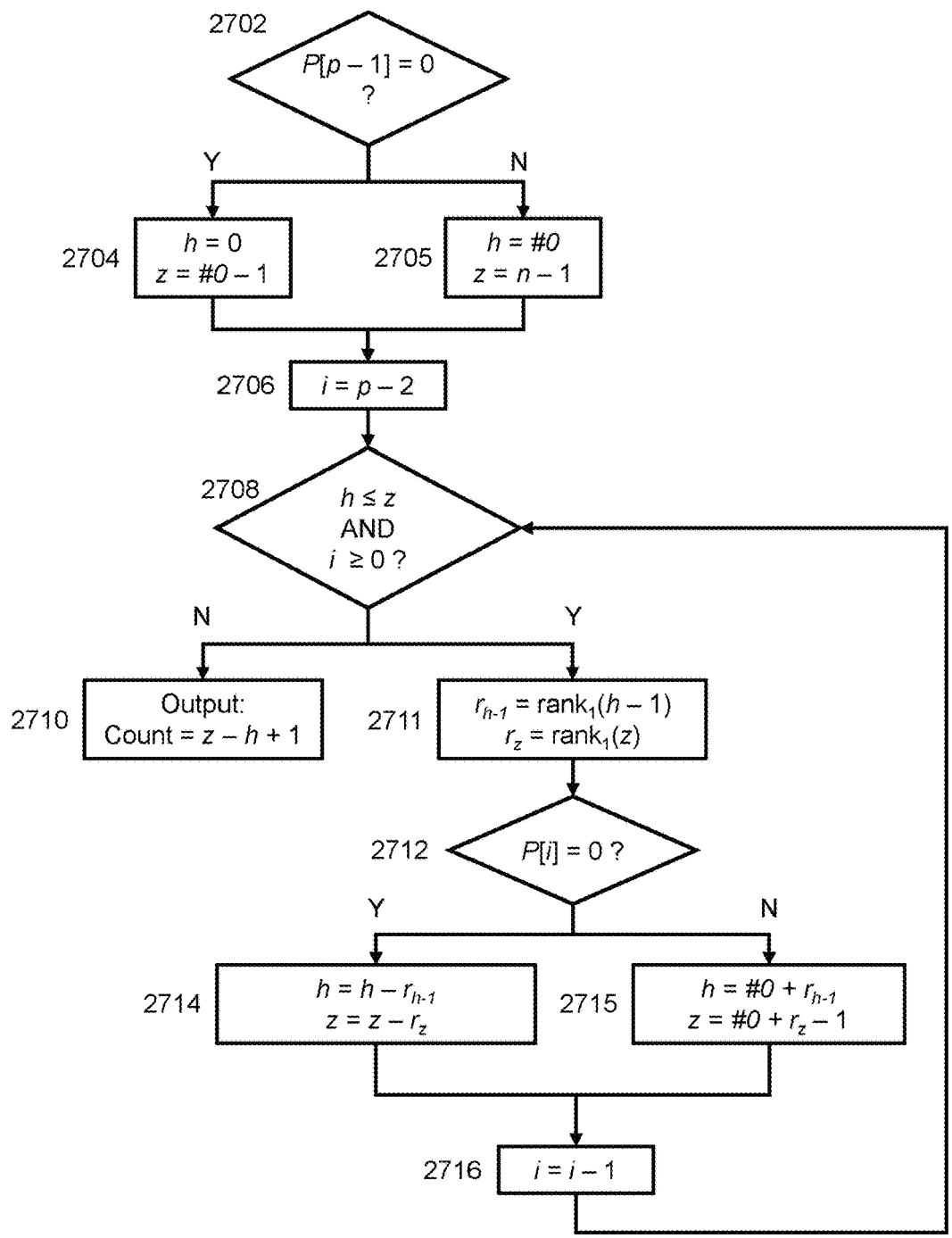
FIG. 27 shows a flowchart for a count operation on a binary string.

As an alternative to the counting method described in relation to FIG. 26, FIG. 27 shows a flowchart describing method 2700 for a count operation, counting the occurrences of the binary pattern P in the string s, according to an illustrative implementation. Pattern P has length p bits, and string s has length n bits. Method 2700 first involves, at 2702, a decision block" that is conditional to check if the last symbol P[p-1] of pattern P is equal to 0. If the last symbol is equal to 0 (Y), then at step 2704 a first index h is set equal to 0 (e.g., the first position in a first column of a Burrows-Wheeler matrix), and a last index z is set equal to #0 (the number of 0's in string s) minus 1. In this case, the first and last indices h and z may delimit a range of suffixes each starting with 0. If the last symbol of P is not equal to 0 (N), then at step 2705 the first index is set equal to #0, and the last index is set equal to n−1. In this case, the first and last indices may delimit a range of suffixes each starting with 1.

Method 2700 further involves at step 2706 setting a loop counter i equal to p−2. This loop counter may enable method 2700 to scan P backwards until occurrences exist (i.e., when the first index is less than or equal to the last index). At 2708, a decision block is implemented and conditional on the first index being less than or equal to the last index and the loop counter i being greater than or equal to zero. If the conditions of decision block 2708 are not met (N), then at block 2710, the output count is determined to be equal to z−h+1. If the conditions of decision block 2708 are met (Y), then at step 2711, a first rank $r_{h-1}$ is executed, with respect to symbol value 1, at the index preceding the first index h (first index minus 1) on a Burrows-Wheeler transform ($BWT_s$) of string s. A last rank $r_z$ is executed, with respect to symbol value 1, at a position equal to the last index z on the $BWT_s$.

At step 2712, another decision block is executed, conditional upon the $i^{th}$ symbol of pattern P being equal to 0. If the condition is met (Y), then at step 2714 the first index h is recalculated to equal one less than the current first index minus the first rank $r_{h-1}$, and the last index z is recalculated to equal one less than the current last index minus the last rank $r_z$. The new first index h at step 2714 may be calculated as the difference of the current first index and the rank, with respect to symbol value 0, at the index preceding the current first index on the $BWT_s$, and the new last index z may be calculated as the difference of the current last index and the rank, with respect to symbol value 0, at the current last index on the $BWT_s$. If the decision block 2712 condition is not met (N), meaning the $i^{th}$ value of pattern P is 1, then at step 2715 the first index h is recalculated to equal the sum of the number of 0's in s and the first rank $r_{h-1}$. The last index z is recalculated to equal one less than the sum of the number of 0's in s and the last rank $r_z$. At step 2716 the loop counter is incremented down by one, and the method returns to decision block 2708. Steps 2711-2716 are iterated if the conditions of block 2708 are still met.

Method 2700, at step 2711, specifically executes rank operations for 1-bits, hence the notation $rank_1$. This is slightly different from how method 2600 executes rank operations, where rank is determined with respect to the preceding bit value in pattern P. However, both methods yield the same result, because the rank at a position x with respect to bit value 1, $rank_1(x)$, can be easily converted to the rank at position x with respect to bit value 0, $rank_0(x)$, by the following equations:

$$rank_0(x)=x-rank_1(x)+1 \quad \text{Eqn. 2}$$

$$rank_1(x)=x-rank_0(x)+1 \quad \text{Eqn. 3}$$

Accordingly, step 2711 may alternatively implement $rank_0$.

Figure 28:
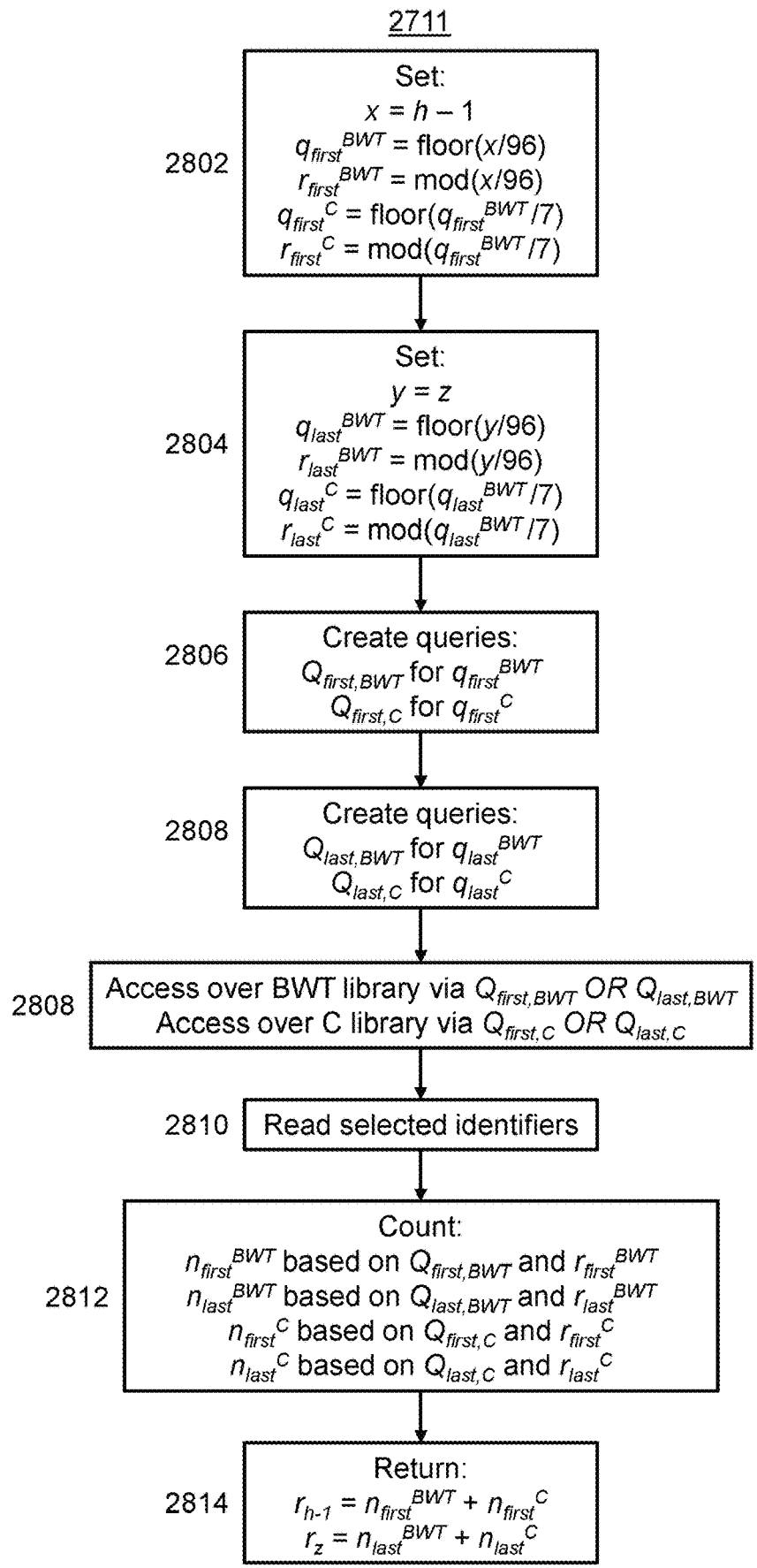
FIG. 28 shows a flowchart for execution of a step of the method in FIG. 29.

Step 2711 of method 2700 in FIG. 27 involves execution of two rank operations. This step is described in further detail in FIG. 28 as method 2711 for execution of two rank operations in parallel via two access operations and two read operations, according to an illustrative implementation. Method 2711 in FIG. 28 is executed iteratively according to the decision block 2708 in method 2700. Method 2711 uses certain parameters from the example encoding scheme described in relation to FIGS. 18 and 19; however, it should be understood that other encoding schemes having alternative parameters may be applied to these methods.

Step 2802 of method 2711 involves setting a parameter x equal to one less than the current first index (from algorithm 1). Step 2802 further involves setting $q_{first}^{BWT}$ equal to the floor (largest integer less than) of x divided by 96 (the number of bits encoded in each container), where $q_{first}^{BWT}$ is the index of a container in a library storing $BWT_s$, the specific container storing the $x^{th}$ bit of $BWT_s$. A parameter $r_{first}^{BWT}$ is set equal to the modulus (remainder) of x and 96, where the parameter indicates the offset of the $x^{th}$ bit in that container. Similar parameters are computed for a counter array c. $q_{first}^{C}$ is set equal to the floor of $q_{first}^{BWT}$ divided by 7 (the number of counters per container), where $q_{first}^{C}$ is the container in a library storing c that includes the $q_{first}^{BWT-th}$ counter of c. $r_{first}^{C}$ is set equal to the modulus of $q_{first}^{BWT}$ and 7, indicating the offset in that container of the counter.

Step 2804 of method 2711 involves setting a parameter y equal to the last index (from algorithm 1) and setting the same BWT and counter array parameters as step 2802 for parameter y, denoted by $q_{last}^{BWT}$, $r_{last}^{BWT}$, $q_{last}^{C}$, and $r_{last}^{C}$. Step 2804 involves creating queries $Q_{first,BWT}$ and $Q_{first,C}$ which identify the container including the $x^{th}$ bit of $BWT_s$ and the container including the counter of 1's before that container. The queries identify containers, so the queries may be two paths whose components represent $q_{first}^{BWT}$ over 7 digits in base 3 and $q_{first}^{C}$ over 7 digits in base 3, respectively. Step 2806 involves similarly creating queries $Q_{last,BWT}$ and $Q_{last,C}$ which are specialized on $q_{first}^{BWT}$ and $q_{first}^{C}$, respectively. Step 2808 involves execute in parallel a first access operation of $Q_{first,BWT}$ and $Q_{last,BWT}$ in union (an OR logical) over the target library storing $BWT_s$, and a second access operation of $Q_{first,C}$ and $Q_{last,C}$ in union over the target library storing counter array c. In some implementations, these access operations retrieve at most 2 containers each (which could be one container if they are equal) and need 16 accessors (4 times the ceiling of 7 divided by π, the technological limitation for reading), because the unified queries may be four paths of 7 components each, and π is equal to 2 (e.g., for PCR). Step 2810 involves merging the sets of identifiers selected by the access operations and reading the sets. In some implementations, these identifiers are included in no more than 4 containers, each container including no more than 28 identifiers, and thus they are at most 4×28=112 in total.

Step 2812 involves counting, in a parameter $n_{first}^{BWT}$, the number of identifiers having leading 7 component-long paths equal to $Q_{first,BWT}$ and having a last component less than or equal to $r_{first}^{BWT}$. Similarly, a parameter $n_{last}^{BWT}$ is set equal to the number of identifiers having leading 7 component-long paths equal to $Q_{last,BWT}$ and having a last component less than or equal to $r_{last}^{BWT}$. Step 2814 involves setting a parameter $n_{first}^{C}$ equal to the value corresponding to the $r_{first}^{C-th}$ counter in the container storing identifiers having 7 component-long leading paths equal to $q_{first}^{C}$. A parameter $n_{last}^{C}$ is set similarly. In step 9, an output, first rank RF, is set equal to the sum of $n_{first}^{BWT}$ and $n_{first}^{C}$, and another output, last rank RL, is set equal to the sum of $n_{last}^{BWT}$ and $n_{last}^{C}$.

For what concerns the retrieval of the occurrences which lie in a suffix array sa[0, n−1] built on the suffixes of string s in the range R delimited by the first and last indices, the fetch operation may be implemented by specifying as many 7 component-long paths for a library storing the suffix array as containers that contain those occurrences. In the encoding scheme example, every container includes 7 suffix positions, so the fetch operation may be executed with no more than 2+(last index−first index+1)/7 paths. These paths may share components, because they may identify a consecutive range of containers. A super-query may be implemented which retrieves more identifiers than needed, deferring the filtering of identifiers to a post-processing computational phase. A minimum integer z may define a size S(z) equal to $3^z \times 7$ which is greater than (last index−first index+1), with z equal to 0, 1, . . . , 7. The range R may be covered by at most 2 ranges of size S(z), and these can be defined by two partial-path queries consisting of (7−z) components. The super-query may be executed with a number of accessors equal to the ceiling of (7−z)/π, with possibly one replication operation, to get a superset of the pattern occurrences (by a multiplicative factor 3, if they are more than 7 occurrences). A read operation may then be executed over the merging of the identifiers resulting from the two queries.

Figure 29:
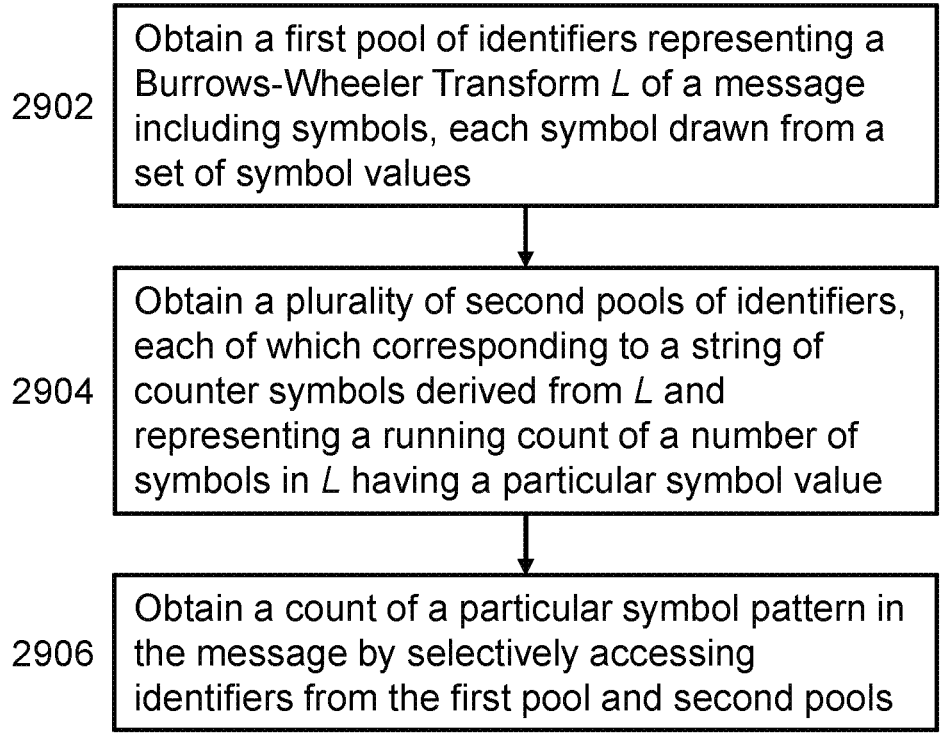
FIG. 29 shows a flowchart for execution of a count operation on an arbitrary string.

Up until this point, the count operation has been described in examples using binary strings; however, the count operation may also be implemented over DNA storing arbitrary strings. A string s drawn from an arbitrary alphabet served as the basis for the Burrows-Wheeler transform and suffix array shown in FIGS. 16 and 17. By exploiting the string BWT(s) and additional data structures, the present disclosure provides for searching of a pattern drawn from an arbitrary alphabet. FIG. 29 shows a flowchart for a method 2900 for performing a count operation on an arbitrary, symbolic string, according to an illustrative implementation. Step 2902 involves obtaining a first pool of identifiers, the identifiers representing a Burrows-Wheeler Transform L (last column of the BWT matrix) of a string of symbols (s), where each symbol in the string of symbols is taken from a set of symbol values. Step 2904 involves obtaining second pools of identifiers, each second pool representing a string of counter symbols derived from BWT(s) L and representing a running count of a number of symbols in L having a particular symbol value. Step 2906 involves obtaining the count of a particular symbol pattern in the symbolic string, by selectively accessing identifiers from the first pool and the set of second pools. Following method 2900, the methods described in FIGS. 26-28 with respect to binary strings may be applied to each pair of pools representing a bit string and a corresponding counter string.

For example, step 2906 may involve reconstructing a first column F of the Burrows-Wheeler Transform matrix for s. Using a series of probes, identifiers may be accessed from the last counter symbol of each of the second pools that represent the total number of occurrences of each corresponding symbol value in L. This total number of occurrences of each corresponding symbol value may be used to reconstruct F. Knowing F, 2906 may further involve determining a range of positions in F that have the last (p-th) symbol value in the pattern, having length p. Said range of positions in F is defined by a first position h and a last position z, inclusive of h and z.

Step 2906 may further include, for each preceding symbol in the pattern after the p-th symbol: determining a first rank of the corresponding symbol value in L at a position immediately preceding the range and a second rank of the corresponding symbol value in L at a position at the end of the range, using a series of probes to access the identifier nucleic acid molecules from the first pool and the corresponding second pool; and using the first rank and the second rank to update the range to the range of positions in F that have instances of the corresponding symbol that precede the subsequent symbol in the pattern. The first rank $r_{h-1}$ is of the respective preceding symbol value in the pattern, at position h−1 in L, and the second rank $r_z$ is of the respective preceding symbol value in the pattern, at position z in L. Updating the range includes setting h to the position of the $(r_{h-1}+1)$-th instance of the respective preceding symbol value in the pattern, in F and setting z to the index of the $r_z$-th instance of the respective preceding symbol value in the pattern, in F. The count of occurrences of the pattern may be set based on the final values of the first and second ranks or of the first and last indices. For example, the count is a difference between the final values of the first and second ranks. The count is set to zero if the first and second ranks are equal to each other for the p-th symbol or any preceding symbol.

The symbolic string L may be transformed into r bit strings of length equal to the length of L, where r represents the number of symbol values in the set of symbol values. A bit string Le may be created for each symbol value R, for v=1, 2, . . . , r by representing every occurrence of R, in L with one bit value (e.g., 1) and representing the occurrence of all other symbol values with the other bit value (e.g., 0). For example, given a symbol string S="BABBO", then bit strings $S_A$=01000, $S_B$=10110, and $S_O$=00001 may be created. The total number of 1's among all bit strings is equal to the length of the original symbol string. In some implementations, there are r first pools, each corresponding to the string of bits $L_v$. The first pool corresponding to $L_v$ may be used to determine the first and second ranks of a symbol value $R_v$ in the pattern.

The counter symbols may be derived from each bit string such that each counter symbol is represented by a string of b counter bits indicative of a running count of a number of bits, for every w bits in the corresponding string of bits, that have a specific bit value (e.g., 1). In some implementations, the value of w is set equal to the value of b. In other implementations, w is set to the value of one.

Each pool may have a solid, liquid, or solid form and may be formed by forming a plurality of identifier nucleic acid molecules. Each identifier may correspond to a respective bit position and may be formed by physically assembling M selected component nucleic acid molecules. Each of the M selected components may be selected from a set of distinct component nucleic acid molecules that are separated into M different layers. The identifiers may be collected in the first pool to represent the string of bits such that the bit values are indicated by a presence or absence of the corresponding identifier in the first pool. Similarly, the second pool of identifiers may be formed by collecting the identifiers that each represent a bit in the counter string. In some implementations, the first pool is the same as the second pool, and, in other implementations, the first pool and the second pool are separate.

The pools of identifiers may be configured such that the presence or absence of identifiers does not correlate directly with one bit value or another in $L_v$, but such that blocks of contiguously ordered identifiers referred to as codewords can be translated to blocks of bits in $L_v$, for v=1, 2, . . . , r. The codewords may correspond to a fixed number of unique identifiers out of a fixed number of possible unique identifiers. Additional information may be stored. For example, additional information may be stored for use in detecting and correct errors in writing, accessing, and reading identifiers from the first and second pool. The additional information may be stored in the identifiers of the first or second pool.

In some implementations, method 2900 further involves obtaining a pool of identifiers representing a suffix array SA derived from the BWT. Each element of the SA may be represented by a bit string of at least $\log_2(n)$ bits indicative of the index of the corresponding element of L. Method 2900 may further involve locating the occurrences of the pattern, given that the count is greater than zero, by accessing the identifiers in the pool representative of the suffix array. These steps may be performed as a fetch operation. In some implementations, method 2900 involves obtaining a pool of identifiers representative of the arbitrary string, which may be a message for example. The context of a first location of the pattern P may be extracted by accessing the identifiers in the fourth pool corresponding to the first location and the neighboring positions surrounding the first location.

Given a string s of length n symbols drawn from an arbitrary alphabet Σ of size |Σ|. The string "abracadabra$", as shown in FIGS. 16 and 17, is an example of such an arbitrary string. In the previous method described in relation to FIG. 29, it was discussed that searching for a pattern P of length p in the string s relies on counting symbols in prefixes of the BWT of s via implementation of the general $rank_\sigma(x)$ operation which counts the occurrences of symbol σ in the string prefix s[0, x] (a subset of string s from the first index to the index x). This method requires executing as many $rank_\sigma$ operations as there are symbols in the searched pattern, because $rank_\sigma(x)$ may be implemented by executing one $rank_1(x)$ operation over the characteristics binary string $S_6$ which has bit value '1' where s has symbol σ.

The following lab example aims to execute fewer $rank_\sigma$ operations and to utilize an approach that works with low-weight codebooks. This implementation exploits the grouping of symbols in searching for the pattern P, virtually enlarging the alphabet and reducing in turn the number of iterations.

For this example, a string $S^k[0: n-1]$ is defined as follows: k is an integer parameter starting from 1 and bounded above by the string length n, and the macro-symbol $S^k[i]$ is the sub-string occupying the last k symbols of the $i^{th}$ row in the matrix inducing the BWT. Each string $S^k$ may be stored in n×k bytes. For this example, using the input string "abracadabra$", there are the following sub-strings. $S^1$ is the BWT of s, i.e., BWT(s), because the last k=1 symbols of a row in the BWT matrix is exactly the last column L which is BWT(s). $S^2$ is equal to "ra br ad a$ br ac da $a ra ca ab ab", because the last k=2 symbols are taken from each row. Spaces are included for ease of reading, and each group of 2 symbols is considered as a unique "macro-symbol." Accordingly, macro-symbol $S^2[3]$ is "a$", and $S^2$ consists of n=12 macro-symbols of 2 characters each, totaling 24 bytes.

$S^3$ is equal to "bra abr cad ra$ abr rac ada a$a bra aca dab $ab", because the last k=3 symbols are taken from each row. $S^3$ consists of 12 macro-symbols of 3 characters each, totaling 36 bytes. These strings may be repeatedly constructed for each k up to n.

$S^k$ strings are not necessarily explicitly constructed, but may be derived as follows. A new string $\hat{S}^k$ may be defined such that $\hat{S}^k[i]$ is equal to $S^k[i_1][1]$, meaning that for every macro-symbol of $S^k$, only the first symbol of the macro-symbol is kept, hence the symbol at distance k from the last column L in the BWT matrix. The $i^{th}$ macro-symbol of $S^k[i]$ by concatenating the $i^{th}$ (single) symbols of all strings $\hat{S}^k[i]\hat{S}^{k-1}[i]\hat{S}^{k-2}[i] \ldots \hat{S}^1[i]$. A reduced space occupancy is afforded by $\hat{S}^k$, which stores only n symbols, less than the k×n symbols stored by each $S^k$.

For pattern searching, $\text{rank}_\alpha$ operations must be executed over the $S^k$ strings, where α is a macro-symbol of length k symbols. An encoding strategy may be implemented for the single symbols of the $\hat{S}^k$ strings, the strategy mimicking the above example for the symbol string "BABBO". Specifically, the $\hat{S}^k$ strings are partitioned into blocks of b containers each (where in the lab example, each container encodes 12 bytes, hence 12 symbols of s). A counter $c_\alpha^k$ is kept for the number of occurrences of every macro-symbol α before that $k^{th}$ block in $\hat{S}^k$. Added to the counter $c_\alpha^k$ may be the total number of macro-symbols α'<α which occur in S. This feature may make it possible to not need to store an additional counter array C with a number of occurrences. There may be at most $|\Sigma|^k$ counters per block.

In some implementations, not all sub-strings α of length k occur in s and thus need not be stored in $c_\alpha^k$. Sub-strings which do exist or do not exist may be tracked in order to only store their corresponding data structures either in DNA, via the encoding schemes described herein, or by a hybrid storage scheme that deploys both DNA-based data storage as described herein and the internal memory of a computer. The hybrid storage scheme may implement a re-mapping between existing (macro-)symbols in string s and the integers in the range [0, . . . ]. A real alphabet $\hat{\Sigma}_k$ may denote the symbols appearing in s (properly encoded by consecutive integers). There may be a real alphabet $\hat{\Sigma}_k$ symbols less than or equal to the minimum of n or $|\Sigma|^k$ for any k. This re-mapping may be implemented by a hash table (e.g., Cuckoo hashing) kept in internal memory or a compressed solution based on rank data structures.

As means for example, let pattern P equal "dab" in the string "abracadabra". The previous data structures are deployed for macro-symbols of length 1 and 2, and search for P is split into two phases which operate backward on P. First, search for "ab", and, second, search for "d". Starting with a first index first equal to zero and a last index last equal to 11, the rows prefixed by ab are determined. This first step involves accessing string $S^2$ and executing over this string the operations $\text{rank}_{ab}(\text{first}-1)$, equal to 0, and $\text{rank}_{ab}(\text{last})$, equal to 2. These rank operations may be executed by two parallel access operations and two parallel read operations over the string $S^2$ and its counter array $c_{ab}^2$. The number of strings smaller than "ab" are 2 in s, so new values for indices are first=2+$\text{rank}_{ab}$(first−1)=2 and last=2+$\text{rank}_{ab}$(last)−1=3. The rows prefixed by ab are two and occur at rows 2 and 3 of the BWT matrix, as can be seen in FIG. 16. The second step involves determining the rows prefixed by "dab", thus "pre-pending" symbol "d" to "ab". This step is executed by accessing $S^1$ and executing over this string the operations $\text{rank}_d$(first−1)=0 and $\text{rank}_d$(last)=1. The number of strings smaller than "d" are 9 in s, so new values for indices are first=9+$\text{rank}_d$(first−1)=9 and last 9+$\text{rank}_d$(last)−1=9. The new indices are equivalent, so the process may be stopped and return the count of occurrences of P as 1. In this example, 2 iterations/steps are executed to search for P, instead of the 3 rounds that would be needed if searching was performed one symbol at a time. A similar search operation is described in relation to FIG. 32 for a general case.

In order to count the occurrences of a pattern in a string, the BWT, a counter array, a suffix array, and access and read methods have been implemented. In some implementations, the string itself may be stored in DNA and accessed at locations of particular patterns. If a search method is used to find the locations of the patterns in the string, then those locations and their surrounding neighborhoods may be accessed within the identifier pool representing the string and subsequently read. This process may be useful, for example, to gather the contexts in which a particular string pattern occurs.

Identifier libraries may be replicated and aliquoted into separate containers, so multiple pattern searches may be executed simultaneously in parallel. For example, 10, 100, 1000, or more pattern searches may be performed in parallel. The rank and fetch operations of different searches may be multiplexed at the point of reading by using a DNA sequencer and a unique barcode to label the identifiers belonging to different searches.

In the foregoing, it was discussed that the BWT may include a forward transform and a backward transform. By the examples above, it is shown that each row of M', the sorted cyclic-shift matrix for the BWT, contains a permutation of an input string S with the symbol $ appended (i.e., the string S$). Similarly, each column of M' contains a permutation of S$. In particular, the first column F, for the exemplary string "abracadabra", is "aaaaabbcdr" which is alphabetically sorted and represents the best-compressible transformation of the original input string. F is not invertible, so the last column L is used as the BWT due to reversibility and compressibility.

Every row of i of M' can be decomposed into three parts, because the leftward cyclic shift: a suffix $S[k_i, n-1]$ of S, the special symbol $, and the prefix $S[1, k_i-1]$. For example, in FIG. 16, row 2 of M' is prefixed by "abra", followed by $, and suffixed by "abracad." As a first property of the BWT matrix, a symbol of the last column L[i] precedes the symbol of the first column F[i] in the string S, except for the row i representing S$ such that F[i]=S[1] and L[i]=$. This property is a result of the nature of every row of M and M' being a left cyclic shift of S$, so, by taking the first and last symbols of each row, the last symbol (which is in L) is immediately followed by the first symbol (which is in F) over the string S. A second property of the BWT matrix is that all the occurrences of a same symbol c in L maintain the same relative order as in F. This property means that the $k^h$ occurrence of symbol c in L corresponds to the $k^{th}$ occurrence of the symbol c in F. A method called "LF-mapping" may exploit these properties to reconstruct S from its BWT(s)=(L', r). LF-mapping may be represented as an array of size n. The $i^{th}$ entry of the array, LF[i], is equal to j if and only if the symbol L[i] maps to symbol F[j]. If L[i] is the $k^{th}$ occurrence of symbol c in L, then F[LF[i]] is the $k^{th}$ occurrence of c in F.

Figure 30:
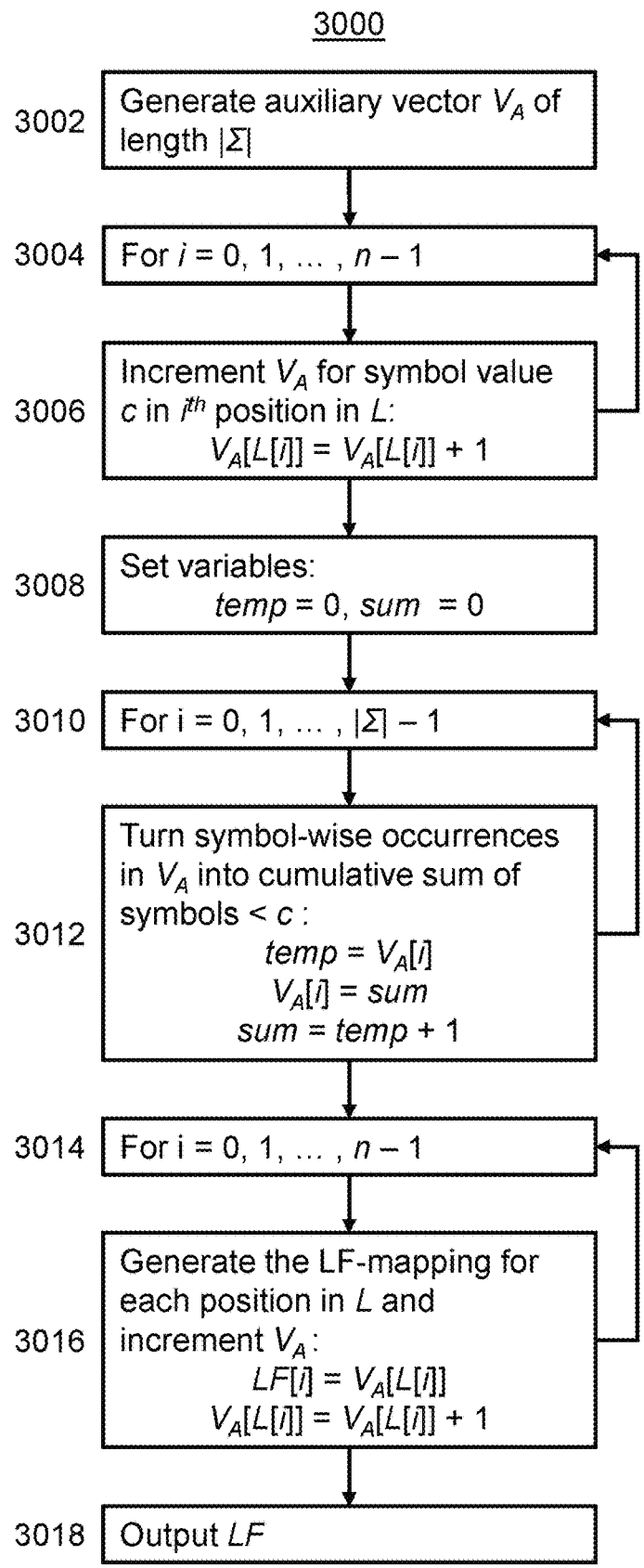
FIG. 30 shows a flowchart for LF-mapping.

FIG. 30 shows an method 3000 for constructing the LF-mapping from column L, according to an illustrative implementation. At step 3002, method 3000 defines an auxiliary vector $V_A$, of size |Z+1. $V_A$ may be indexed by a symbol or an a integer. A first for loop at step 3004 determines, for each symbol c in L, the number $n_c$ of its occurrences in L, and stores $V_A[c]=n_c$ at step 3006. Then, a second for loop at step 3010 turns these symbol-wise occurrences into a cumulative sum, so that at step 3012 the new $V_A[c]$ stores the total number of occurrences in L of symbols smaller than c, namely $V_A[c]=\Sigma_{x<c} n_x$. This step is done by adopting two auxiliary variables at step 3008, so that the overall working space is still of size on the order of n. $V_A[c]$ gives the first position in F where symbol c occurs. Therefore, before the last for loop starts, $V_A[c]$ is the landing position in F of the first c in L (the LF-mapping for the first occurrence of every alphabet symbol is known). Finally, a last for loop at step 3014 scans the column L and, whenever it encounters symbol L[i]=c, then at step 3016 it sets LF[i]=$V_A[c]$. This condition is correct when c is met for the first time; then $V_A[c]$ is incremented so that the next occurrence of c in L will map to the next position in F (given the contiguities in F of all rows starting with that symbol). So the algorithm keeps the invariant that LF[i]=$\Sigma_{x<c} n_x+k$; after that, k occurrences of c in L have been processed. At step 3018, an output of the final LF (LF-mapping array) is generated.

Figure 31:
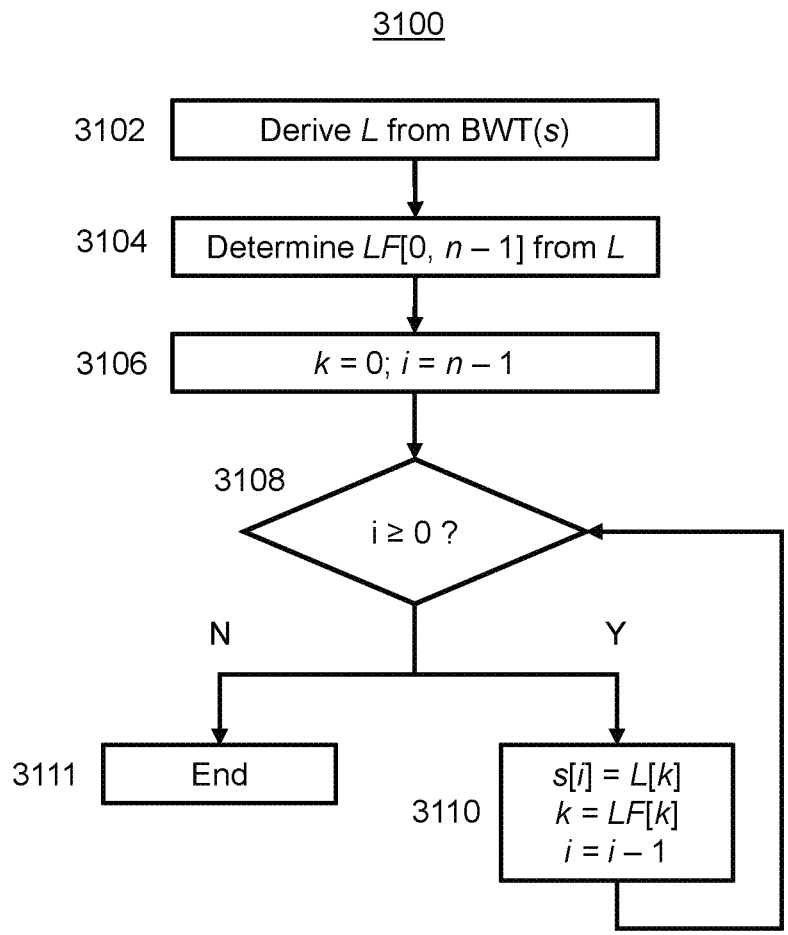
FIG. 31 shows a flowchart for reconstructing a string from a Burrows-Wheeler transform.

Given the LF-mapping and fundamental properties described above, S may be reconstructed backwards starting from the transformed output BWT(s)=(L', r). A method 3100 for reconstruction of the string S is shown in FIG. 31, according to an illustrative implementation. At step 3102, L is reconstructed from BWT(s) by inserting $ at position r of L'. At step 3104, the LF-mapping of L is determined. Step 3104 may be executed via method 3000 of FIG. 30. At step 3106, auxiliary variables k and i (a loop counter) are set. Variable k is initially set to zero, and loop counter i is initially set to n−1, the final position of the length of L, F, and s. At decision block 3108, method 3100 checks if loop counter i is greater than or equal to zero. If the condition is met (Y), an iteration proceeds via step 3110. Step 3110 involves picking the last symbol of S, namely S[n−1], which can be identified at L[0], given that the first row of M' is $S. Then, the method proceeds by moving one symbol at a time to the left in S, deploying the two properties above: the second property allows mapping of the current symbol occurring in L (initially L[0]) to its corresponding copy in F; then the first property allows finding of the symbol which precedes that copy in F by taking the symbol at the end of the same row (i.e., the one in L). This double step, which returns on L, allows a one symbol leftward movement in s. Repeating this process up to the beginning of S, this string may be reconstructed. When the condition of decision block 3108 is no longer met (N), method 3100 ends at step 3111, where the original string s is fully constructed.

As an example, refer to FIG. 16 where L[0]=S[n−1]="a", and execute the loop of method 3100 (repeating steps 3108 and 3110). LF[0] points to the first row starting with "a"—this is the row 1. So that copy of "a" is LF-mapped to F[1] (in fact, F[1]="a"), and the preceding symbol in S is L[1]="r". These two basic steps are repeated until the whole string S is reconstructed. Just continuing the previous running example, L[1]="r" is LF-mapped to the symbol in F at position LF[1]=10 (in fact, F[10]=r). L[1] and F[10] is the first occurrence of symbol "r" in both columns L and F, respectively. The algorithm then takes as preceding symbol of "r" in S the symbol L[10]="b". These steps are then repeated for each preceding symbol of the remainder of the string S.

Having noted the bijective correspondence between the rows of the rotated matrix M and the suffixes of string S, as well as the relationship between the last column L and the suffix array built on S, these relationships are at the core of the design of the FM-index, discussed above. The FM-index allows efficient sub-string search and space occupancy of size on the order of string size n. Accordingly, three basic search operations underlie the design of such a indexed search: count(P) returns the range of rows [first, last] in M which are prefixed by the string P, where the value (last−first+1) accounts for the number of pattern occurrences; locate(P) returns the list of all positions in string S where P occurs, where the list is either sorted or unsorted; and extract(i,j) returns the substring S[i,j] by accessing its compressed representation in the FM-index. For example, in FIG. 17 for the pattern P="ab", the indices first=2 and last=3 return a total of two pattern occurrences. These two rows correspond to the suffixes S[0,1] and S[7:] which are prefixed by pattern P.

As described above in relation to FIGS. 26-29, the retrieval of the rows first and last is not implemented via a binary search but it uses a search method which deploys the column L, the array C (which counts in C[c] the number of occurrences in s of all symbols smaller than c) and an additional data structure which supports efficiently the counting rank(c, k) which reports the number of occurrences of the symbol c in the string prefix L[0, k−1]. All data structures L, C, and rank can be stored compressed and still retrieve efficiently their entries: namely access L[i] or C[c], or answer rank(c, k).

Figure 32:
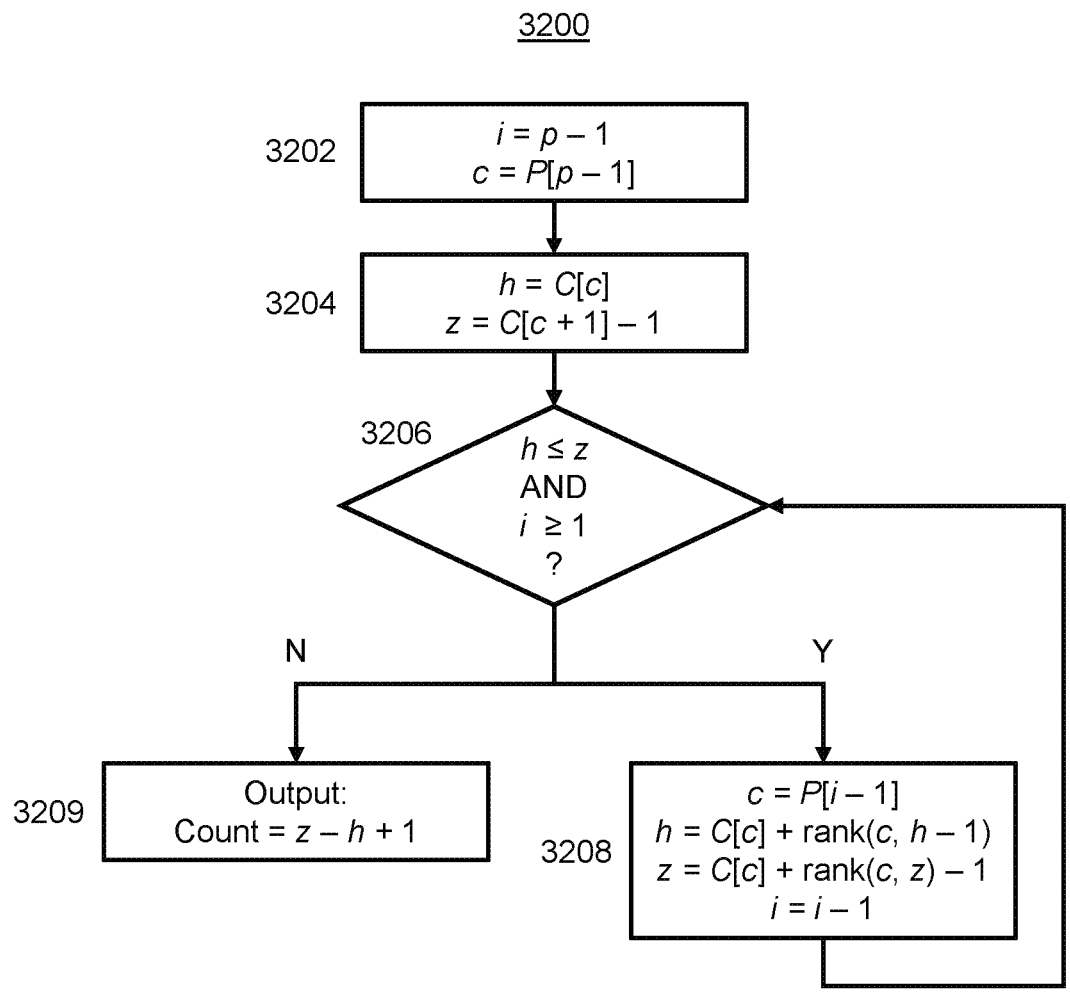
FIG. 32 shows a flowchart for a count operation.

FIG. 32 shows a method 3200 configured to implement count(P) using the above ensemble, according to an illustrative implementation. Step 3202 involves setting a loop counter i to equal p−1, indicative of the last position in pattern P. Variable symbol c is set equal to the last symbol in P, indicated by P[p−1]. At step 3204, a first index h is set equal to the counter entry for variable symbol c, indicated by C[c], where C is a counter array derived from a Burrows-Wheeler Transform of a sting of symbols. A last index z is set equal to one less than the counter entry at position c+1. First and last indices h and z delimit a range of values in a first column F of the matrix M' derived from the BWT. A decision block 3206 checks if the first index h is less than last index z and if loop counter i is greater than or equal to one. If both conditions are met (Y), then at step 3208, the variable symbol c is set to the preceding symbol of pattern P. A new first index h is set equal to the sum of the counter entry for c and the rank of the BWT computed at position h−1 with respect to symbol value c. A new las index z is set equal to one less than the sum of the counter entry for c and the rank of the BWT computed at position z with respect to symbol value c. Loop counter i incremented down by one, and the method returns to step 3204.

Each iteration steps 3204-3208 of method 3200 preserves the following invariant: at the $i^{th}$ phase, the parameter "h" points to the first row of the sorted rotated matrix M' prefixed by P[i, p−1], and the parameter "z" points to the last row of M' prefixed by P[i, p−1]. Initially, the invariant is true by construction: for first column F, F[C[c]] is the first row of M' starting with c, and F[C[c+1]−1] is the last row of M' starting with c. Returning to the example with P="ab" with respect to FIG. 17, the initial condition is C[b]=6 and C[b+1]=C[c]=8, and [6, 7] is the range of rows prefixed by b before that the backwards-search starts.

At each subsequent iteration, method 3200 has found the range of rows [h, z] prefixed by P[i, p−1]. Then the method involves determining the new range of rows [h, z] prefixed by P[i−1, p−1]=P[i−1] P[i, p−1] by proceeding as follows. First determine the first and last occurrence of the symbol c=P[i−1] in the substring L[h, z] by deploying the function rank properly queried. Specifically rank(c, h−1) counts how many occurrences of c precede position h in L, and rank(c, z) counts how many occurrences of c precede position z in L. These values are then used to compute the LF-mapping of those first/last occurrences of c. There exists the equality LF[i]=C[L[i]]+rank(L[i], i). This equality means that the computation of the LF-mapping can occur efficiently and succinctly provided that the data structure that implements rank(c, k) is stored compactly. Referring again to FIG. 17 and consider, as before, the pattern P="ab" and the range [6, 7] of rows in M' prefixed by P[2]="b". Now picking the previous pattern symbol P[1]="a", Algorithm 5 computes rank("a", 5)=1 and rank("a", 7)=3 because L[0, h−1] contains 1 occurrence of "a", and L[0, z] contains 3 occurrences of "a". So the algorithm computes the new range as: h=C["a" ]+rank("a", 5)=1+1=2, z=C["a" ]+rank("a", 7)−1=1+3-1=3, which is the contiguous range of rows prefixed by the pattern P="ab". After the final phase (i.e., i=0), first and last will delimit the rows of M' containing all the suffixes prefixed by P. If z<h, the pattern P does not occur in S.

Described in the following is the implementation of the location of pattern occurrences via procedure locate(P). For a fixed parameter μ, we sample the rows i of M' which correspond to suffixes that start at positions of the form pos(i)=jμ, for j=0, 1, 2, . . . . Each such pair (i, pos(i)) is stored explicitly in a data structure L that supports membership queries in constant time (on the row-component). Now, given a row index r, the value pos(r) can be derived immediately if r in L is a sampled row; otherwise, the algorithm determines j=LF$^t$(r), for t=1, 2, . . . , until j is a sampled row and is found in L. In this case, pos(r)=pos(j)+t. The sampling strategy ensures that a row in L is found in at most μ iterations, and the occ occurrences of the pattern P can be located via on the order of (μ×occ) queries to the rank data structure.

Notice that count(P) can be adapted to implement the last basic operation supported by FM-index: extract(i, j). Let r be the row of M' prefixed by the suffix S[j, n−1], and assume that the value of r is known. The algorithm sets S[j]=F[r] and then starts a cycle which sets s[j−1−t]=L[LF$^t$[r]], for t=0, 1, . . . , j−i−1. An idea underlying this cycle is that we repeatedly compute the LF-mapping (implemented via the rank data structure) of the current symbol, so jumping backwards in S starting from S[j−1]. The process stops after j−i−1 steps, when S[i] is reached. This approach is similar to the one taken in BWT-inversion; the difference relies in the fact that the array LF is not explicitly available, but its entries are generated step-by-step via rank operations. This approach guarantees still constant-time access to the LF-array, but succinct space storage if a compressed approach for rank is adopted.

In addition to the chemical methods for access, reading, rank, and search described in the foregoing, chemical methods for implementing an "if-then-else" operation are described herein. An "if-then-else" operation is a statement, expression, or construct that perform different computations or actions depending on whether a specified Boolean condition evaluates to true or false. Using this operation, conditional programs may be written. Each "if" operation tests the presence or absence of one or more identifiers, and, depending on its presence or absence, continues to either "then" or "else" branches. The operation may comprise multiple conditions and corresponding branches. An output may be produced from all the branches of the operation. This approach allows for all of the identifiers in a plurality of identifier libraries (e.g., of terabit scale) to be operated upon in parallel. For example, if a library encodes billions data objects, then complex functions that examine each object and produce an output can be designed as DNA-based programs and executed on the libraries in parallel.

Strategies to shift, copy, and move bits enable the rearrangement of a single identifier library into multiple input identifier libraries for the execution of a desired program. Physically, each if-then-else operation may take place in a reaction with an input library and two output libraries and may be multiplexed across all identifiers in those libraries. The output library of one operation may be channeled to the input of another through a fluidic transfer. The execution of each operation in DNA may be slow compared to conventional hardware, but unlike conventional hardware which is limited by RAM and processing power, the DNA platform described herein is capable of executing a program across a massive amount of input data objects simultaneously and with low power.

Figure 33:
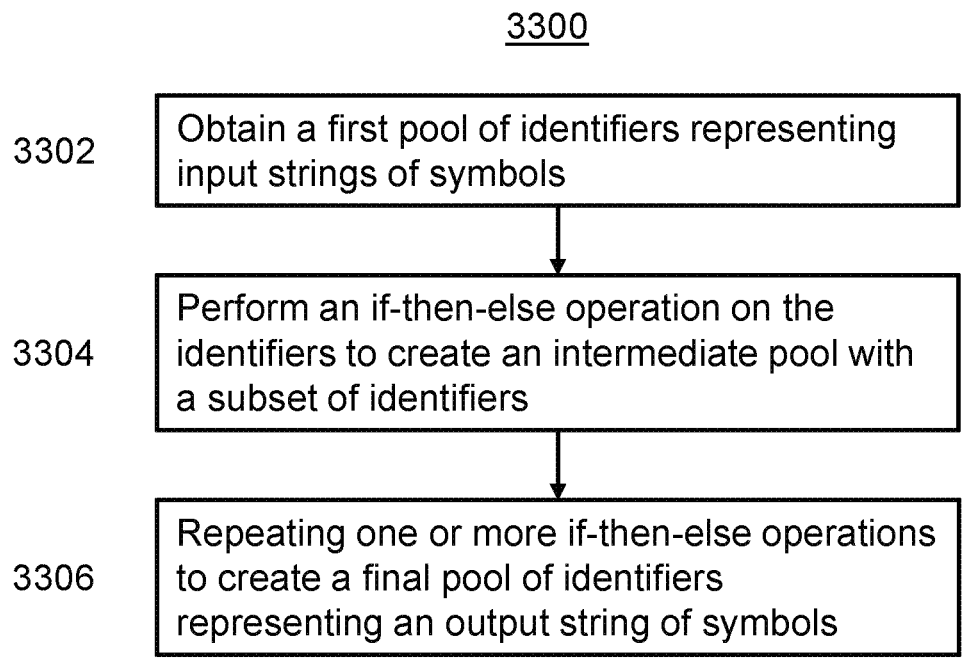
FIG. 33 shows a flowchart for an if-then-else operation.

FIG. 33 shows a flowchart describing a method 3300 for executing one or more if-then-else operations on a pool of identifiers. Step 3302 of method 3300 involves obtaining a first pool of identifiers representing one or more input strings of symbols. Step 3304 involves performing an if-then-else operation on the identifiers to create an intermediate pool with a subset of identifiers from the first pool of identifiers. Step 3306 involves repeating one or more if-then-else operations on the intermediate pool, creating a new intermediate pool after each if-then-else operation, until a final pool of identifiers is generated, the final pool representing an output string of symbols.

The pools have powder, liquid, or solid form. Each identifier in the pools of identifiers is a nucleic acid molecule comprising component nucleic acid molecules. At least a portion of the component nucleic acid molecules are capable of individually binding to one or more probes, such as PCR primers or affinity tagged oligonucleotides. Each identifier may comprise a distinct component from each of M layers, where each layer comprises a set of components.

The if-then-else operations of steps 3304 and 3306 target at least one component of the identifiers with a probe. The operation may involve accessing identifiers in a pool that includes a specific component. For example, the probes are PCR primers, and identifiers are accessed via PCR. As another example, the probes are affinity-tagged oligonucleotides, and identifiers are accessed via an affinity pull-down assay. Multiple if-then-else operations may be performed in parallel on one or more pools. For example, two operations are performed in parallel in two pools of identifiers.

Method 3300 may further involve splitting at least one of the first pool, intermediate pool, or final pool into at least two duplicate pools. This splitting may allow for parallelized if-then-else operations. In order to ensure a sufficient concentration of identifiers, the pool(s) may be replicated prior to splitting, for example, using PCR. Two or more pools (e.g., intermediate pools) may be combined to form a new pool (e.g., a new intermediate pool or a second pool) of identifiers.

As another application, a search for a bitstring of length n may be performed across unstructured data in DNA with a runtime that is equivalent to just one instance of a comparator circuit (on the order of log(n)). Whereas the equivalent search performed on conventional hardware would additionally account for the cost and time of migrating data into RAM. To further this application, consider searching a large data set for any pattern conceived after the data has been encoded, as is common on large archived data sets. For example, the pattern may be all pictures of a person of interest from a large data warehouse of images. After the archive is written, a function may be conceived that is capable of discovering a desired pattern from the data. Such functions can be, for example, constructed using machine learning algorithms. These pattern-discovery functions have Boolean circuit representations and may be implemented in DNA using if-then-else operations. The operation(s) may be applied to all data objects of a data set simultaneously as per the learnt model, and identify objects that fit the pattern of interest. Performing the same operation in conventional hardware would be costly and slow because of limited availability of RAM and processors. As learning algorithms improve, updated programs may be applied to archived data sets to discover new information of interest. Another example application is spatiotemporal signal processing where a convolution function (foundational in digital signal processing functions such as Fourier transform) may be applied to archived data across multiple small windows of time or space in search of a particular pattern. As another example, a hash function may be applied to the objects of a large dataset for security (e.g., authentication) or integrity (e.g. fixity checks) applications.

If input data describes a set of a objects, then the input data may be natively encoded in an identifier library such that each identifier represents a possible object in the set. In this encoding, chemical methods of "AND," "OR," and "NOT" operations between two identifier libraries implement the set operations of "INTERSECTION," "UNION," and "COMPLEMENT," as these operations are defined in the art, in constant runtime. Chemical methods for performing set inclusion (determining if one set is a subset of another) and equivalence may also be performed on the DNA platform. Together these operations and relations may be used to execute any functions in set algebra.

The DNA platform may also include support for machine learning (ML). Conceptual indexing with ML utilizes high dimensional vectors to organize and annotate data. The systems described herein may provide native and efficient storage and query for such data, fully enabling the power of ML models to capture relevant concepts and relationships in data. Operations on DNA such as permutation and sum, as they are known in the art, may be implemented as vector operations to discover, store, and query conceptual relationships efficiently. Identifier libraries may be used as a platform to build intelligent memory that integrates storage and structure natively into the storage medium. The DNA-based storage system natively supports the algorithms and data structures for the platform. A long-lifetime, ultra-low power memory bank may be configured to continually organize data into conceptual structures and enable semantically-rich querying and inference.

The foregoing is merely illustrative of the principles of the disclosure, and the apparatuses and methods can be practiced by other than the described implementations, which are presented for purposes of illustration and not of limitation. Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for obtaining a count of a particular symbol pattern of length $p_s$ in a message comprising a string of symbols of length $n_s$, each symbol being selected from a set of r symbol values, the method comprising:
   (a) obtaining a first pool of identifier nucleic acid molecules representative of a string of symbols L that is the last column of a Burrows-Wheeler Transform matrix of the message, the first pool having powder, liquid, or solid form, and each identifier nucleic acid molecule in the first pool comprising component nucleic acid molecules, at least a portion of which are configured to bind to one or more probes;
   (b) obtaining r second pools of identifier nucleic acid molecules, each of which corresponds to a string of counter symbols, $C_v$ for v=1, 2, ..., r, that is derived from L and represents a running count of a number of symbols in L with a corresponding symbol value $R_v$; and
   (c) obtaining the count of a particular symbol pattern of length $p_s$ in the message, by selectively accessing identifier nucleic acid molecules from the first pool and the r second pools.

2. The method of claim 1, wherein step (c) further comprises reconstructing a first column F of the Burrows-Wheeler Transform matrix.

3. The method of claim 2, wherein step (c) includes, using a series of probes, accessing the identifier nucleic acid molecules from the last counter symbol in each of the r second pools that represent the total number of occurrences of each corresponding symbol value $R_v$ in L; and using said total number of occurrence of each corresponding symbol value $R_v$ to reconstruct F.

4. The method of claim 2, wherein step (c) further includes determining a range of positions in F that have the p-th symbol value in the pattern.

5. The method of claim 4, wherein said range of positions in F is defined by a first position h and a last position z, inclusive of h and z.

6. The method of claim 4, wherein step (c) further includes, for each preceding symbol in the pattern after the p-th symbol:
   determining a first rank of the corresponding symbol value in L at a position immediately preceding the range and a second rank of the corresponding symbol value in L at a position at the end of the range, using a series of probes to access the identifier nucleic acid molecules from the first pool and the corresponding second pool; and
   using the first rank and the second rank to update the range to the range of positions in F that have instances of the corresponding symbol that precede the subsequent symbol in the pattern.

7. The method of claim 6, wherein the first rank rh−1 is of the respective preceding symbol value in the pattern, at position h−1 in L, and the second rank rz is of the respective preceding symbol value in the pattern, at position z in L.

8. The method of claim 7, wherein updating the range includes setting h to the position of the $(r_{h-1}+1)$-th instance of the respective preceding symbol value in the pattern, in F.

9. The method of claim 7, wherein updating the range includes setting z to the index of the $r_z$-th instance of the respective preceding symbol value in the pattern, in F.

10. The method of claim 6, wherein step (c) further includes setting the count of occurrences of the pattern in the message based on the final values of the first and second ranks.

11. The method of claim 10, wherein the count of occurrences is a difference between the final values of the first and second ranks.

12. The method of claim 10, wherein the count of occurrences is set to zero if the first and second ranks are equal to each other for the p-th symbol or for any preceding symbol.

13. The method of claim 1, wherein the first pool of identifier nucleic acid molecules is one of r first pools, each corresponding to a string of bits $L_v$ for v=1, 2, . . . , r, such that elements of $L_v$ have a bit-value of '1' for elements of L that match the symbol value $R_v$ and a bit-value of '0' otherwise, or vice versa.

14. The method of claim 13, wherein the first pool corresponding to $L_v$ is used to determine the first and second rank of a symbol value $R_v$ in the pattern.

15. The method of claim 1, further comprising obtaining a pool of identifier nucleic acid molecules, the SA pool, representative of a suffix array, SA, that is derived from the Burrows-Wheeler Transform of the message, each element of SA represented by a bit string of at least $\log_2(n)$ bits indicative of the position of the corresponding element of L in the message.

16. The method of claim 15, further comprising locating the occurrences of the pattern in the message, given that the count is greater than zero, by accessing identifier nucleic acid molecules in the SA pool that correspond to elements of the SA at positions given by the final range of positions in F.

17. The method of claim 16, further comprising obtaining a message pool of identifier nucleic acid molecules representative of the message.

18. The method of claim 17, further comprising extracting the context of a first location of the pattern by accessing the identifier nucleic acid molecules in the message pool corresponding to said first location and the neighborhood of positions surrounding the first location.

19. The method of claim 1, wherein step (c) includes:
(c.1) determining a first position h and a last position z, that define a range of the $p^{th}$ symbol value in the first column F, inclusive of h and z;
(c.2) using a series of probes to access the identifier nucleic acid molecules from a first pool and a second pool to calculate a rank rh−1 of the $(p-i)^{th}$ symbol value of the pattern, at position h−1 in L, where i=1;
(c.3) using a series of probes to access the identifier nucleic acid molecules from a first pool and a second pool to calculate a rank $r_z$ of the $(p-i)^{th}$ symbol value of the pattern, at position z in L;
(c.4) if $r_h$−1 is equal to $r_z$, setting the count of occurrences of the pattern in the message as zero; and
(c.5) otherwise, if $r_{h-1}$ is not equal to $r_z$,
(c.5.A) setting h to the index of the $(r_{h-1}+1)$th instance of the $(p-i)^{th}$ symbol value in F;
(c.5.B) setting z to the index of the $r_z^{th}$ instance of the $(p-i)^{th}$ symbol value in F;
(c.5.C) incrementing i by one;
(c.5.D) repeating steps (c.2), (c.3), (c.4), (c.5), (c.5.A), (c.5.B), and (c.5.C) a number of times until i=p−1; and
(c.5.E) calculating the count of occurrences of the pattern in the message as z−h+1.

20. The method of claim 19, wherein the first pool and the second pool in (c.2) correspond to the $(p-i)^{th}$ symbol value of the pattern.

21. The method of claim 19, wherein the first pool and the second pool in (c.3) correspond to the $(p-i)^{th}$ symbol value of the pattern.

* * * * *